US009200026B2

(12) United States Patent  
Liang et al.

(10) Patent No.: US 9,200,026 B2
(45) Date of Patent: *Dec. 1, 2015

(54) ANTIBACTERIAL AGENTS

(71) Applicant: MERCK SHARP & DOHME CORP., Rahway, NJ (US)

(72) Inventors: Chang-Hsing Liang, San Diego, CA (US); Jonathan Duffield, San Francisco, CA (US); Alex Romero, San Diego, CA (US); Yu-Hung Chiu, Del Mar, CA (US); Steve Sucheck, Maumee, CA (US); Kenneth Marby, San Diego, CA (US); Youe-Kong Shue, Carlsbad, CA (US); Yoshitaka Ichikawa, San Diego, CA (US); Chan-Kou Hwang, San Diego, CA (US); David Rabuka, Kensington, CA (US); Sulan Yao, San Diego, CA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/722,058

(22) Filed: Dec. 20, 2012

(65) Prior Publication Data

US 2013/0345410 A1 Dec. 26, 2013

Related U.S. Application Data

(63) Continuation of application No. 13/136,172, filed on Jul. 26, 2011, now Pat. No. 8,343,936, which is a continuation of application No. 12/430,736, filed on Apr. 27, 2009, now Pat. No. 8,012,943, which is a continuation of application No. 10/548,698, filed as application No. PCT/US2004/006645 on Mar. 5, 2004, now Pat. No. 7,601,695.

(60) Provisional application No. 60/468,242, filed on May 6, 2003, provisional application No. 60/453,601, filed on Mar. 10, 2003.

(51) Int. Cl.
*A61K 31/70* (2006.01)
*C07H 17/08* (2006.01)
*C07D 498/04* (2006.01)

(52) U.S. Cl.
CPC .............. *C07H 17/08* (2013.01); *C07D 498/04* (2013.01)

(58) Field of Classification Search
CPC ............................. C07H 17/08; C07D 498/04
USPC .......................................................... 536/7.4
See application file for complete search history.

(56) References Cited

U.S. PATENT DOCUMENTS

| | | | |
|---|---|---|---|
| 1,354,753 | A | 10/1920 | Howard |
| 3,843,787 | A | 10/1974 | Fabrizio |
| 4,312,866 | A | 1/1982 | Caruso |
| 4,331,803 | A | 5/1982 | Watanabe |
| 4,474,768 | A | 10/1984 | Bright |
| 4,742,049 | A | 5/1988 | Baker |
| 5,211,955 | A | 5/1993 | Legros |
| 5,444,051 | A | 8/1995 | Agouridas |
| 5,527,780 | A | 6/1996 | Agouridas |
| 5,543,400 | A | 8/1996 | Agouridas |
| 5,635,485 | A | 6/1997 | Agouridas |
| 5,656,607 | A | 8/1997 | Agouridas |
| 5,747,467 | A | 5/1998 | Agouridas |
| 5,760,233 | A | 6/1998 | Agouridas |
| 5,770,579 | A | 6/1998 | Agouridas |
| 5,834,428 | A | 11/1998 | Drucker |
| 5,985,844 | A | 11/1999 | Heck |
| 6,011,142 | A | 1/2000 | Bonnet |
| 6,020,521 | A | 2/2000 | Randolph |
| 6,028,181 | A | 2/2000 | Or |
| 6,096,714 | A | 8/2000 | Agouridas |
| 6,121,432 | A | 9/2000 | Bonnet |
| 6,270,768 | B1 | 8/2001 | OConnell |
| 6,395,300 | B1 | 5/2002 | Straub et al. |
| 6,395,710 | B1 | 5/2002 | Chu |
| 6,407,074 | B1 | 6/2002 | Bronk |
| 6,407,257 | B1 | 6/2002 | Agouridas et al. |
| 6,420,535 | B1 | 7/2002 | Phan |
| 6,437,106 | B1 | 8/2002 | Stoner |
| 6,440,941 | B1 | 8/2002 | Denis |
| 6,455,505 | B2 | 9/2002 | Agouridas |
| 6,515,116 | B2 | 2/2003 | Suh |

(Continued)

FOREIGN PATENT DOCUMENTS

| | | |
|---|---|---|
| CN | 1354753 | 6/2002 |
| CN | 101045063 | 10/2007 |

(Continued)

OTHER PUBLICATIONS

Baker, W.R. et al., 'Modification of macrolide antibiotics. Synthesis of 11-deoxy-11-(carboxyamino)-6-0-methylerythromycin A 11,12-(cyclic esters) via an intramolecular Michael reaction of O-carbamates with an alpha, beta-unsaturated ketone,' J. Org. Chem., 53:2340-2345, 1988.

(Continued)

*Primary Examiner* — Elli Peselev

(74) *Attorney, Agent, or Firm* — Brannon Sowers & Cracraft PC

(57) ABSTRACT

Described herein are novel macrolides, the preparation of novel macrolides, the use of novel macrolides for preventing, treating, or ameliorating various conditions, and the use of novel macrolides as antibacterial agents.

20 Claims, No Drawings

(56) References Cited

U.S. PATENT DOCUMENTS

| | | |
|---|---|---|
| 6,555,524 B2 | 4/2003 | Kaneko |
| 6,664,238 B1 | 12/2003 | Su |
| 6,777,393 B2 | 8/2004 | Bronk |
| 6,809,188 B1 | 10/2004 | Suh |
| 6,849,608 B2 | 2/2005 | Su |
| 6,890,907 B2 | 5/2005 | Speirs |
| 7,163,924 B2 | 1/2007 | Burger |
| 7,332,476 B2 | 2/2008 | Burger |
| 7,375,234 B2 | 5/2008 | Sharpless |
| 7,419,961 B2 | 9/2008 | Napoletano |
| 7,601,695 B2 | 10/2009 | Liang et al. |
| 8,247,394 B2 | 8/2012 | Fernandes |
| 8,791,080 B2 | 7/2014 | Fernandes |
| 8,796,232 B2 | 8/2014 | Fernandes |
| 2002/0028781 A1 | 3/2002 | Agouridas |
| 2002/0044967 A1 | 4/2002 | Yamashita |
| 2003/0143162 A1 | 7/2003 | Speirs |
| 2003/0176327 A1 | 9/2003 | Cassell |
| 2004/0009930 A1 | 1/2004 | Su |
| 2005/0009764 A1 | 1/2005 | Burger et al. |
| 2005/0014706 A1 | 1/2005 | Falzari |
| 2005/0022242 A1 | 1/2005 | Rosetti |
| 2005/0153905 A1 | 7/2005 | Burger |
| 2005/0209172 A1 | 9/2005 | Woo |
| 2005/0222427 A1 | 10/2005 | Sharpless |
| 2006/0100164 A1 | 5/2006 | Liang |
| 2006/0264385 A1 | 11/2006 | Wang |
| 2007/0015719 A1 | 1/2007 | Jenkins |
| 2007/0167382 A1 | 7/2007 | Finkelstein |
| 2007/0197518 A1 | 8/2007 | Johnson |
| 2007/0281894 A1 | 12/2007 | Gant |
| 2008/0113926 A1 | 5/2008 | Ivezic |
| 2008/0221048 A1 | 9/2008 | Woo |
| 2008/0227730 A1 | 9/2008 | Mutak |
| 2008/0241959 A1 | 10/2008 | Culic |
| 2008/0287376 A1 | 11/2008 | Das |
| 2009/0075916 A1 | 3/2009 | Upadhyay |
| 2009/0076253 A1 | 3/2009 | Kashimura |
| 2009/0087389 A1 | 4/2009 | Leonard |
| 2009/0156517 A1 | 6/2009 | Zhang |
| 2010/0216731 A1 | 8/2010 | Pereira |
| 2011/0195920 A1 | 8/2011 | Fernandes |
| 2012/0071429 A1 | 3/2012 | Duffield |
| 2012/0172323 A1 | 7/2012 | Fernandes |
| 2013/0018008 A1 | 1/2013 | Pereira |
| 2013/0053362 A1 | 2/2013 | Castro |
| 2013/0164351 A1 | 6/2013 | Fernandes |
| 2013/0172280 A1 | 7/2013 | Pereira |
| 2013/0345410 A1 | 12/2013 | Liang |
| 2014/0088062 A1 | 3/2014 | Pereira |

FOREIGN PATENT DOCUMENTS

| | | | |
|---|---|---|---|
| EP | 0248279 | A2 | 12/1987 |
| EP | 0680967 | A1 | 11/1995 |
| EP | 1024145 | A2 | 8/2000 |
| EP | 1167375 | | 1/2002 |
| GB | 891817 | | 3/1962 |
| JP | 2000507573 | | 6/2000 |
| JP | 2000351794 | | 12/2000 |
| JP | 2002514197 | | 5/2002 |
| JP | 2004502736 | | 1/2004 |
| JP | 2006528667 | | 12/2006 |
| JP | 2007536371 | | 12/2007 |
| JP | 2008519788 | | 6/2008 |
| JP | 2008534504 | | 8/2008 |
| JP | 2009502788 | | 1/2009 |
| WO | 9830574 | A1 | 7/1998 |
| WO | 9856800 | A1 | 12/1998 |
| WO | 9921866 | A1 | 5/1999 |
| WO | 9928311 | A1 | 6/1999 |
| WO | 0012521 | A1 | 3/2000 |
| WO | 0031099 | A1 | 6/2000 |
| WO | 0044761 | A2 | 8/2000 |
| WO | WO 00/44761 | * | 8/2000 |
| WO | 0062783 | A2 | 10/2000 |
| WO | WO 00/62783 | * | 10/2000 |
| WO | 0110878 | A1 | 2/2001 |
| WO | 0250092 | A1 | 6/2002 |
| WO | 03004509 | | 1/2003 |
| WO | 03004509 | A2 | 1/2003 |
| WO | 03072141 | A1 | 9/2003 |
| WO | 2004080391 | A2 | 9/2004 |
| WO | 2005105821 | | 11/2005 |
| WO | 2006087642 | | 8/2006 |
| WO | 2007008537 | | 1/2007 |
| WO | 2007059307 | A2 | 5/2007 |
| WO | 2007143507 | | 12/2007 |
| WO | 2009055557 | | 4/2009 |
| WO | 2009055557 | A1 | 4/2009 |
| WO | 2011008193 | | 1/2011 |
| WO | 2011112864 | A1 | 9/2011 |
| WO | 2011119604 | | 9/2011 |
| WO | 2011146829 | | 11/2011 |
| WO | 2013148891 | | 10/2013 |
| WO | 2014145210 | | 9/2014 |
| WO | 2014152326 | | 9/2014 |

OTHER PUBLICATIONS

Djokic, S. et al., 'Erythromycin Series. Part 11. Ring Expansion of Erythromycin A Oxime by the Beckmann Rearrangement.' J. Chem. Soc Perkin Trans 1., 1881-1890 (1986).

Phan, L.T. et al., 'Synthesis of 2-Fluoro-6-O-propargyl-11,12-carbamate Ketolides. A Novel Class of Antibiotics,' Org. Ltrs., 2:2951-2954 (2000).

Or et al., 'Design, Synthesis, and Antimicrobial Activity of 6-0-Substituted Ketolides Active Against Resistant Respiratory Tract Pathogens', J. Med. Chem., 43:1045-49 (2000).

Champney et al., 'Structure-Activity Relationships for Six Ketolide Antibiotics', Current Microbiology, 42:203-10 (2001).

Denis et al., Beta-Keto-Ester Chemistry and Ketolides. Snythesis and antibacterial Activity of 2-Halogeno, 2-Methyl and 2,3 Enol-Ether Ketolides, Bioorganic & Medicinal Chemistry Letters, 10:2019-22 (2000).

Torne et al. 'Peptidotriazoles on Solid Phase: [1,2,3]-Triazoles by Regiospecific Copper(I)-Catalyzed 1,3-Dipolar Cycloadditions of Terminal Alkynes to Azides', J. Org. Chem., 67:3057-64 (2002).

LeMahieu, R. A., Carson, M., and Kierstead, R. W., 'Glycoside Cleavage Reactions on erythromycin A. Preparation of Erythronolide A,' Journal of Medicinal Chemistry, vol. 17, No. 9, 1974, 953-956.

Birkenmeyer, R. D., Kroll, S. J., Lewis, C., Stern, K. F., and Zurenko, G. E., 'Synthesis and Antibacterial Activity of Clindamycin Analogues: Pirlimycin, a Potent Antibacterial Agent', Journal of Medicinal Chemistry, vol. 27, No. 2, 1984, 216-223.

Vince, R., Almquist, R. G., Ritter, C. L., and Daluge, S., Antimicrobial Agents and Chemotherapy, vol. 8, No. 4, 1975, 439-443.

Celebuski, J.E. et al., 'Chemical Modification of Erythromycin: Novel Reaction Observed by Treatment with Metalloporphyrins', vol. 35, No. 23, pp. 3837-3850, 1994, Elsevier Science Ltd.

Morimoto S. et al., 'Chemical Modification of Erythromycins VII. Molecular Rearrangement Observed During Chemical Modification Study of the Desosamine Unit of Erythromycins', Heterocycles, Elsevier Science Publishers, vol. 31, No. 2, Jan. 1, 1990, pp. 305-319.

Hill, D.R. et al., 'Novel Macrolides via meso-Tetraarylmetalloporphyrin Assisted Oxidation', Tetrahedron Letters, vol. 37, No. 6, pp. 787-790, 1996, Elsevier Science Ltd.

Rostovtsev, V.V. et al., 'A Stepwise Huisgen Cycloaddition Process: Copper(I)=Catalyzed Regioselective 'Ligation' of Azides and Terminal Alkynes,' Angew. Chem. Int. Ed., 41: 2596-2599 (2002).

Ma et al., Curr. Med. Chem., "Anti-Infective Agents," vol. 1, 2002, pp. 15-34.

Holzer, G., et al., "Ka1,2 and KB1,3 X-Ray Emission Lines of the 3d Transition Metals", Dec. 1997, Physical Review, vol. 56, No. 6, pp. 4554-4568.

Berge, Stephen M., et al., "Pharmaceutical Salts", 1977, Journal of Pharmaceutical Sciences, vol. 66, No. 1, pp. 1-19.

(56) References Cited

OTHER PUBLICATIONS

Bermudez, Luiz E., et al., "Telithromycin is Active Against *Mycobacterium avium* in Mice Despite Lacking Significant Activity in Standard In Vitro and Macrophage Assays and Is Associated with Low Frequency of Resistance During Treatment", 2001, Antimicrobal Agents and Chemotherapy, vol. 45, No. 8, pp. 2210-2214.

Cynamon, M. H., et al., "Activity of ABT-773 Against *Mycobacterium avium* Complex in the Beige Mouse Model", 2000, Antimicrobal Agents and Chemotherapy, vol. 44, No. 10, pp. 2895-2896.

Patel, Ramesh N., "Stereoselective Biocatalysis", 2000, Bristol-Myers Squibb Research Institute; pp. 775-797.

Bebear, C.M., et al., In vitro activity of trovafloxacin compared to those of five antimicrobials against mycoplasmas including Mycoplasma hominis and Ureaplasma urealyticum fluoroquinolone-resistant isolates that have been genetically characterized, Antimicrob Agents Chemother 44:2557-2560 (2000).

Laine, Loren, et al., "Prospective comparison of H&E, Giemsa and Genta stains for the diagnosis of Helicobacter pylori," 1997, Gastrointestinal Endoscopy, vol. 45, No. 6, pp. 463-467.

Lee, Adrian, et al., "A standard mouse model of Helicobacter pylori infection: introducing the Sydney Strain," 1997, Gastroenterology, vol. 112, pp. 1386-1397.

Feder, P. I., et al., 1991. Statistical Analysis of Dose-Response Experiments by Maximum Likelihood Analysis and Iteratively Reweighted Nonlinear Least Squares Regression Techniques, 1991, Drug Information Journal, vol. 28, pp. 323-334.

Inglesby, Thomas V., et al., "Anthrax as a Biological Weapon, 2002", 2002, Journal of the American Medical Association, vol. 287, No. 17, pp. 2236-2252.

Nilius et al.: 'Ketolides: the future of the macrolides?' Current Opinion in Pharmacology, [Online] vol. 2, Jan. 14, 2002, pp. 1-8 Retrieved from the Internet: <URL:http://www.sciencedirect.com/science/article/pii/S1471489202001984>.

Caira MR, "Crystalline polymorphism of orgainic compounds," Design of Organic Solids, Topics in Current Chemistry, Springer Berlin Heidelberg, 1998, p. 163-208.

Pathak et al., "Enzymatic Protecting Group Techniques in Organic Synthesis," Stereosel, Biocatal., 2000; pp. 775-797.

Baker, William R., et al. "Modification of macrolide antibiotics. Synthesis of 11-deoxy-11-(carboxyamino)-6-O-methylerythromycin A 11, 12-(cyclic esters) via an intramolecular Michael reaction of O-carbamates with an. alpha.,. beta.-unsaturated ketone." The Journal of Organic Chemistry 53.10 (1988): 2340-2345.

Barcia-Macay, Maritza, et al., 'Pharmacodynamic Evaluation of the Intracellular Activities of Antibiotics Against *Staphylococcus aureus* in a Model of THP-1 Macrophages', 2006, Antimicrobial Agents and Chemotherapy. vol. 50, No. 3, pp. 841-851.

Bermudez, Luiz E., et al., "EDP-420, a Bicyclolide (Bridged Bicyclic Macrolide), Is Active Against *Mcyobacterium avium*", 2007, Antimicrobal Agents and Chemotherapy, vol. 51, No. 5, pp. 1666-1670.

Crone, Julia, et al., "Evaluation of a monoclonal antibody-based test for detection of Helicobacter pylori-Specific Antigen in stool samples from mice," Jul. 2004, Clinical and Diagnostic Laboratory Immunology, vol. 11, No. 4, pp. 799, 800.

Drusano, G. L., et al., "Is 60 Days of Ciprofloxacin Adminstration Necessary for Postexposure Prophylaxis for Bacillus Anthracis?", 2008, Antimicrobial Agents and Chemotherapy. vol. 52, No. 11, pp. 3973-3979.

Duffy, L., et al., Fluoroquinolone resistance in Ureaplasma parvum in the United States, J Clin Microbiol 44:1590-1591 (2006).

Jensen, J.S., et al., Azithromycin Treatment Failure in Mycoplasma genitaliumPositive Patients with Nongonococcal Urethritis Is Associated with Induced Macrolide Resistance, Clin Infect Dis 47:1546-53 (2008).

Jones et al.: 'MIC Quality Control Guidelines and Disk Diffusion Test Optimization for CEM-101, a Novel Fluoroketolide' Journal of Clinical Microbiology vol. 48, No. 4, Dec. 30, 2009, pp. 1470-1473.

Katz, Leonard, and Gary W. Ashley. "Translation and protein synthesis: macrolides." Chemical reviews 105.2 (2005): 499-528.

Lemaire, Sandrine, et al., "Cellular Accumulation and Pharmacodynamic Evaluation of the Intracellular Activity of CEM-101, a Novel Fluoroketolide, Against *Staphylococcus aureus, Listeria monocytogenes* and *Legionella pneumophila* in Human THP-1 Macrophages", 2009, Antimicrobial Agents and Chemotherapy. vol. 53, No. 9, pp. 3734-3743.

Li, X., et al., Emerging macrolide resistance in Mycoplasma pneumoniae in children: detection and characterization of resistant isolates, Pediatr Infect Dis J, 28:693-696 (2009).

Liang C. H. et al., 'Synthesis and biological activity of new 5-0-sugar modified ketolide and 2-fluoro-ketolide antibiotics,' Bioorganic & Medicinal Chemistry Letters, Pergamon, Elsevier Science, GB, vol. 15, No. 5, Mar. 1, 2005, pp. 1307-1310.

Physicians' Desk Reference, p. 2905, (2007).

Plata, Daniel J., et al. "The synthesis of ketolide antibiotic ABT-773 (cethromycin)." Tetrahedron 60.45 (2004): 10171-10180.

Romero et al., 'An efficient entry to new sugar modified ketolide antibiotics' Tetrahedron Letters, vol. 46, 2005, pp. 1483-1487.

Vennerstrom, Jonathan L., et al., "Identification of an Antimalarial Synthetic Trioxolane Drug Development Candidate", 2004, Letters to Nature, vol. 430, pp. 900-904.

Waites, K.B., et al., Mycoplasmas and ureaplasmas as neonatal pathogens, Clin Microbiol Rev 18:757-89 (2005).

Zuckerman, "Macrolides and ketolides: azithromycin, clarithromycin, telithromycin", Infectious Disease Clinics of North America, vol. 18, (2004), pp. 621-649.

PCT Search Report and Written Opinion for PCT/US2011/037330 completed Aug. 26, 2011.

PCT International Search Report and Written Opinion for PCT/US2011/029424, mailed May 25, 2011.

Threlfall, Terence L. "Analysis of organic polymorphs. A review." Analyst 120.10 (1995): 2435-2460.

Petit, Samuel, and Gérard Coquerel. "The amorphous state." Polymorphism: In the Pharmaceutical Industry 10 (2006): 1.

Organic Compounds Crystal Manufacture Handbook—Principles and Knowhow, 2008, pp. 57 to 84.

Hancock, Bruno C., Sheri L. Shamblin, and George Zografi. "Molecular mobility of amorphous pharmaceutical solids below their glass transition temperatures." Pharmaceutical research 12.6 (1995): 799-806.

Ashizawa, Kazuhide, "Physico-Chemical Studies on the molecular Details of Drug Crystals," Phar Tech Japan, 2002, vol. 18, No. 10. pp. 81-96.

PCT Search Report and Written Opinion prepared for PCT/US2009/061978 mailed Dec. 9, 2009.

European Search Report for EP 09 82 2827, dated Mar. 21, 2012.

International Search Report for PCT/US2009/061977, dated Dec. 23, 2009, (3 pages).

PCT Search Report/Written Opinion prepared for PCT/US2010/048540, mailed Oct. 21, 2010.

Byrn, S., Pfeiffer, R., Ganey, M., Hoiberg, C., & Poochikian, G. (1995). Pharmaceutical solids: a strategic approach to regulatory considerations. Pharmaceutical research, 12(7), 945-954.

Sumerkan, B., Aygen, B., Doganay, M., & Sehmen, E. (1996). Antimicrobial susceptibility of Bacillus anthracis against macrolides. Salisbury Med Bull Supplement, 87, 138.

Maurin, M., Mersali, N. F., & Raoult, D. (2000). Bactericidal activities of antibiotics against intracellular Francisella tularensis. Antimicrobial agents and chemotherapy, 44(12), 3428-3431.

Luna, V. A., King, D. S., Gulledge, J., Cannons, A. C., Amuso, P. T., & Cattani, J. (2007). Susceptibility of Bacillus anthracis, Bacillus cereus, Bacillus mycoides, Bacillus pseudomycoides and Bacillus thuringiensis to 24 antimicrobials using Sensititre® automated microbroth dilution and Etest® agar gradient diffusion methods. Journal of antimicrobial chemotherapy, 60(3), 555-567.

Barthel, D., Schlitzer, M., & Pradel, G. (2008). Telithromycin and quinupristin-dalfopristin induce delayed death in Plasmodium falciparum. Antimicrobial agents and chemotherapy, 52(2), 774-777.

Still, J. G., et al. "Single Oral Dose Pharmacokinetics and Safety of CEM-101 in Healthy Subjects." 46th Annual Meeting. Idsa, 2008.

(56) References Cited

OTHER PUBLICATIONS

Lee, Joo Hyun, and Myung Gull Lee. "Dose-dependent pharmacokinetics of telithromycin after intravenous and oral administration to rats: contribution of intestinal first-pass effect to low bioavailability." J. Pharm. Pharm. Sci 10 (2007): 37-50.
Chen, M., Muri, E. M., Jacob, T. M., & Williamson, J. S. (2003). Synthesis and bioactivity of erythromycin derivatives. Medicinal chemistry research, 12(3), 111-129.
Kerdesky, F. A., Premchandran, R., Wayne, G. S., Chang, S. J., Pease, J. P., Bhagavatula, L., . . . & King, S. A. (2002). Synthesis of 2'-O-Benzoyl-3-keto-6-O-propargyl-11, 12-carbamoyl Erythromycin A. Organic process research & development, 6(6), 869-875.
Zhu, Z. J., Krasnykh, O., Pan, D., Petukhova, V., Yu, G., Liu, Y., . . . & Franzblau, S. G. (2008). Structure-activity relationships of macrolides against *Mycobacterium tuberculosis*. Tuberculosis, 88, S49-S63.
Putnam S. D. et al, Antimicrobial Characterization of Solithromycin (Cem-101), A Novel Fluroroketolide: Activity Against *Staphlococci* and *Enterococci*. International Journal of Antimicrobial Agents, vol. 37, No. 1, 2011, pp. 39-45.
Written Opinion, Singapore Application No. 11201405895U; Intellectual Property Office of Singapore; Mar. 31, 2015, 6 pages.
International Search Report Written Opinion for PCT/US2008/080936 completed Dec. 8, 2008.
Database WPI Week 200822 Thomson Scientific, London, GB; AN 2008-D02982.
Zimmermann, Torsten, et al. "Comparative tolerability of intravenous azithromycin, clarithromycin and erythromycin in healthy volunteers." Clinical Drug Investigation 21.8 (2001): 527-536.
Luke, D. R., and G. Foulds. "Toleration of intravenous azithromycin." The Annals of pharmacotherapy 31.9 (1997): abstract only.
Cannon, John B., N. Adeyinka Williams, and Karen J. Papp. "Reduction of pain on intravenous infusion with bile salt formulations for a macrolide antibiotic." International journal of pharmaceutics 114.1 (1995): abstract only.
Lu, Yan, YanJiao Wang, and Xing Tang. "Formulation and thermal sterile stability of a less painful intravenous clarithromycin emulsion containing vitamin E." International journal of pharmaceutics 346.1 (2008): abstract only.
Llano-Sotelo, B., D. Klepacki, and A. S. Mankin. 2008. Binding and action of CEM-10, a new macrolide/ketolide in development for treating infections with macrolide-resistant and macrolide-susceptible bacteria. 48th Annu. Intersci. Conf. Antimicrob. Agents Chemother./46th Infect. Dis. Soc. Am. Ann. Meet., abstr. F1-3983.
International Search Report for PCT/US2015/015353, dated May 14, 2015, (8 pages).
Ferris, C. F., Lu, S. F., Messenger, T., Guillon, C. D., Heindel, N., Miller, M., . . . & Simon, N. G. (2006). Orally active vasopressin V1a receptor antagonist, SRX251, selectively blocks aggressive behavior. Pharmacology Biochemistry and Behavior, 83(2), 169-174.
Amsden, G. W. "Anti-inflammatory effects of macrolides an underappreciated benefit in the treatment of community-acquired respiratory tract infections and chronic inflammatory pulmonary conditions?." Journal of Antimicrobial Chemotherapy 55.1 (2005): 10-21.

* cited by examiner

ANTIBACTERIAL AGENTS

RELATED APPLICATIONS

This application is a continuation application under 35 U.S.C. §120 of U.S. application Ser. No. 13/136,172, filed Jul. 26, 2011, now U.S. Pat. No. 8,343,936, which is a continuation application of U.S. application Ser. No. 12/430,736, filed Apr. 27, 2009, now U.S. Pat. No. 8,012,943, which is a continuation application under 35 U.S.C. §120 of U.S. application Ser. No. 10/548,698, filed Sep. 9, 2005, now U.S. Pat. No. 7,601,695, which is a national stage application under 35 U.S.C. §371 of PCT International Application Serial No. PCT/US2004/006645, filed Mar. 5, 2004, which claims priority to U.S. provisional applications, NOVEL ANTIBACTERIAL AGENTS, Provisional Patent Application Ser. No. 60/468,242, filed May 6, 2003, and MACROLIDES AND PROCESSES FOR THEIR PREPARATION, Provisional Patent Application Ser. No. 60/453,601, filed Mar. 10, 2003, the disclosures of each which are incorporated herein in their entirety by reference.

These compounds, including derivatives of erythromycin A, are used and exhibit desirable activity against a number of Gram-positive pathogens. It is also well known that the widespread use of antibiotics over the past 70 years has resulted in the development of a host of antibiotic-resistant pathogens. Numerous examples of resistant infections have been documented in both the hospital and community settings. The present clinically used macrolide antibiotic compounds may be ineffective against these emerging resistant mutants. Therefore, it is of critical importance to develop and provide new drugs with broad-spectrum activity, particularly against drug-resistant strains.

Erythromycin A is a 14-membered macrolactone with good activity against many Gram-positive bacteria. Resistance to this class of antibiotics has been observed however, occurring by one of three mechanisms: (1) inactivation of the drug by chemical modification, (2) target modification such as ribosomal methylation (known as $MLS_B$) or (3) by macrolide efflux. Furthermore Erythromycin A loses activity in acidic media and the decomposition products can give rise to gastric intolerance in many patients.

A second generation of macrolides, also natural products, contain a 16-membered ring e.g. spiramycin, first described in 1956 (G.B. Pat. No. 758,726). The 16-membered macrolides are also acid susceptible. Clarithromycin (U.S. Pat. No. 4,331,803) and azithromycin (U.S. Pat. No. 4,474,768) exemplify a third generation of macrolides. They are semi-synthetic derivatives of Erythromycin A, which overcome the problem of acid instability by preventing the formation of a 6,9-hemiketal by methylation of the 6-hydroxyl in the case of Clarithromycin and by the conversion of the 9-ketone to a tertiary amine in the case of Azithromycin.

Recently, a new class of macrolide compounds has been disclosed, namely, ketolides. Representative examples include telithromycin (U.S. Pat. No. 5,635,485) and ABT-773 (U.S. Pat. No. 6,028,181), which are designed particularly to combat respiratory tract pathogens that have acquired resistance to macrolides. The ketolides are semi-synthetic derivatives of the 14-membered macrolide erythromycin A. The preparation of these ketolides is disclosed in *J. Med. Chem.*, 2000, 43, P. 1045. *Current Microbiology*, 2001, 42, P. 203. *Bioorganic & Medicinal Chemistry Letters*, 2000, 10, P. 2019. U.S. Pat. No. 6,420,535 and WO patent No. 99/21866. Ketolides are acid-stable and highly potent against most Gram-positive bacteria and do not induce $MLS_B$ resistance.

However, bacterial strains resistant to existing macrolides are being continually isolated and so there is an urgent need to identify new derivatives with improved activity against both Gram-positive and Gram-negative organisms and with superior resistance profiles.

SUMMARY OF THE INVENTION

This invention relates to novel functionalized macrolides, to methods of preparing novel functionalized macrolides, to the use of such novel functionalized macrolides for preventing, treating, or ameliorating various conditions, and to the use of such novel functionalized macrolides as antibacterial agents.

The present invention is directed to compounds represented by Structural Formula 1 and 2 and their pharmaceutically acceptable salts, solvates, esters, hydrates and prodrugs thereof, and methods of making, methods of using, and pharmaceutical compositions having compounds represented by Structural Formula 1 and Formula 2 and pharmaceutically acceptable salts thereof, wherein:

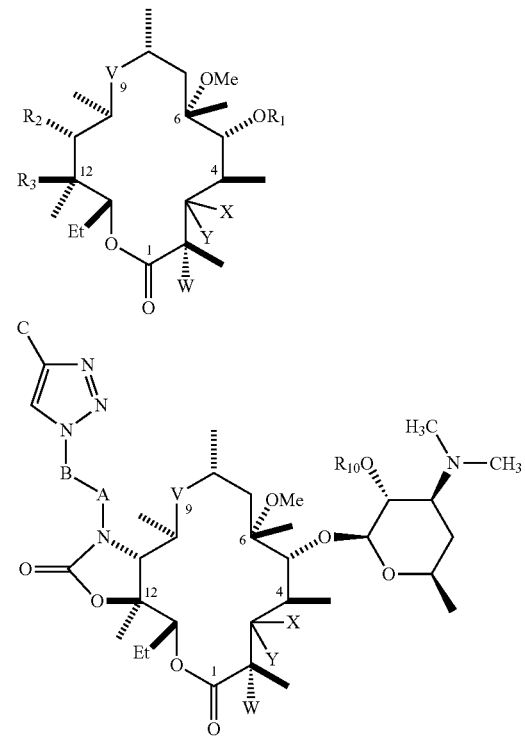

$R_1$ is selected from H, cyclic and acyclic alkyl, cyclic and acyclic alkyl-hydroxyamine, aryl, aryl-hydroxyamine, cyclic and acyclic acyl, cyclic and acyclic acyl-hydroxyamine, heteroalkyl, heteroalkyl-hydroxyamine, heteroaryl, heteroaryl-hydroxyamine, acylaryl, acylaryl-hydroxyamine, acylheteroaryl, acylheteroaryl-hydroxyamine, alkylaryl, alkylaryl-hydroxyamine, alkylheteroaryl, alkylheteroaryl-hydroxyamine, sulfonylalkyl, sulfonylalkyl-hydroxyamine, acylalkoxylsulfonylalkyl, acylalkoxylsulfonylalkyl-hydroxyamine;

or $R_1$ can be —C(O)—$NR_4R_5$, where $R_4$ and $R_5$ can be independently or taken together as hydrogen, hydroxy, alkyl, aralkyl, alkylaryl, alkoxy, heteroalkyl, aryl, heteroaryl, dimethylaminoalkyl, acyl, sulfonyl, urea or carbamate and acceptable salts thereof;

or $R_1$ can also be a monosaccharide (including amino sugars and their derivatives, particularly, a mycaminose derivatized at the C-4' position or a 4-deoxy-3-amino-glucose derivatized at the C-6' position), a disaccharide (including, a mycaminose derivatized at the C-4' position with another sugar or a 4-deoxy-3-amino-glucose derivatized at the C-6' position with another sugar), a trisaccharide (including aminosugars and halosugars), chloramphenicol, clindamycin or their analogs; provided that $R_1$ can not be desosamine;

$R_2$ and $R_3$ are each independently OH, or $R_2$ and $R_3$ are taken together are as follows:

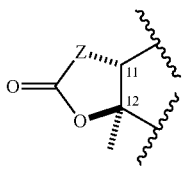

where Z is O, or $-N(R_6)$; where $R_6$ is hydrogen, hydroxy, alkyl, aralkyl, alkylaryl, alkoxy, heteroalkyl, aryl, heteroaryl, dimethylaminoalkyl, acyl, or sulfonyl, ureyl or carbamoyl and pharmaceutically acceptable salts thereof;

X is H;

Y is $OR_7$; where $R_7$ is a monosaccharide or disaccharide (including aminosugars or halosugars), alkyl, aryl, heteroaryl, acyl (particularly, 4-nitrophenylacetyl and 2-pyridylacetyl), or $-C(O)-NR_8R_9$, where $R_8$ and $R_9$ can be independently or taken together as hydrogen, hydroxy, alkyl, aralkyl, alkylaryl, heteroalkyl, aryl, heteroaryl, alkoxy, dimethylaminoalkyl, acyl, sulfonyl, ureyl or carbamyl and pharmaceutically acceptable salts thereof;

Or X and Y taken together are O;

V is $-C(O)-$, $-C(=NR_{11})-$, $-C(NR_{12},R_{13})-$, or $-N(R_{14})CH_2-$, wherein the first dash of each of the foregoing V groups is attached to the C-10 carbon of the compounds of Formulae 1 and 2 and the last dash of each group is attached to the C-8 carbon of the compounds of Formulae 1 and 2 and $R_{11}$ is hydroxy or alkoxy, $R_{12}$ and $R_{13}$ can be independently or taken together as hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof and $R_{14}$ is hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof;

W is H, F, Cl, Br, I, or OH;

A is $-CH_2-$, $-C(O)-$, $-C(O)O-$, $-C(O)NH-$, $-S(O)_2-$, $-S(O)_2NH-$, $-C(O)NHS(O)_2-$;

B is $-(CH_2)_n-$ where n is an integer ranging from 0-10, or B is an unsaturated carbon chain of 2-10 carbons, which may contain any alkenyl or alkynyl group; and C is hydrogen, hydroxy, alkyl, aralkyl, alkylaryl, alkoxy, heteroalkyl, aryl, heteroaryl, aminoaryl, alkylaminoaryl, acyl, acyloxy, sulfonyl, ureyl or carbamoyl and pharmaceutically acceptable salts thereof; wherein $R_{10}$ is hydrogen or acyl.

In another aspect, the present invention includes methods for removing certain moieties, such as monosaccharide or disaccharide moieties, from macrolide compounds, and to the further functionalization of altered macrolide compounds.

In yet another aspect, the present invention provides methods for removing a sugar building block, or a substituted sugar building block, from a macrolide compound having a sugar building block, or a substituted sugar building block as a substituent.

In yet another aspect, the present invention includes methods for synthesizing compounds of Formula 1 and Formula 2, their pharmaceutically acceptable salts, solvates, hydrates, esters or prodrugs thereof, wherein:

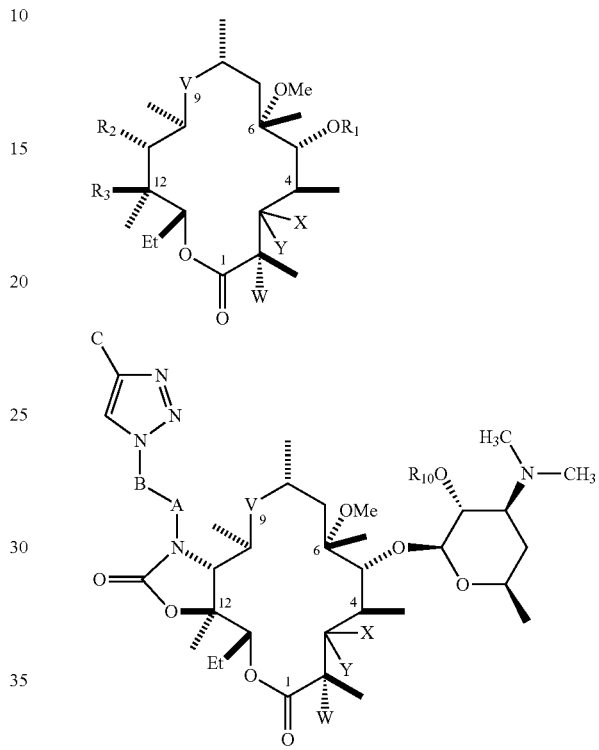

$R_1$ is selected from H, cyclic and acyclic alkyl, cyclic and acyclic alkyl-hydroxyamine, aryl, aryl-hydroxyamine, cyclic and acyclic acyl, cyclic and acyclic acyl-hydroxyamine, heteroalkyl, heteroalkyl-hydroxyamine, heteroaryl, heteroaryl-hydroxyamine, acylaryl, acylaryl-hydroxyamine, acylheteroaryl, acylheteroaryl-hydroxyamine, alkylaryl, alkylaryl-hydroxyamine, alkylheteroaryl, alkylheteroaryl-hydroxyamine, sulfonylalkyl, sulfonylalkyl-hydroxyamine, acylalkoxylsulfonylalkyl, acylalkoxylsulfonylalkyl-hydroxyamine;

or $R_1$ can be $-C(O)-NR_4R_5$, where $R_4$ and $R_5$ can be independently or taken together as hydrogen, hydroxy, alkyl, aralkyl, alkylaryl, alkoxy, heteroalkyl, aryl, heteroaryl, dimethylaminoalkyl, acyl, sulfonyl, urea or carbamate and acceptable salts thereof;

or $R_1$ can also be a monosaccharide (including amino sugars and their derivatives, particularly, a mycaminose derivatized at the C-4' position or a 4-deoxy-3-amino-glucose derivatized at the C-6' position), a disaccharide (including, a mycaminose derivatized at the C-4' position with another sugar or a 4-deoxy-3-amino-glucose derivatized at the C-6' position with another sugar), a trisaccharide (including aminosugars and halosugars), chloramphenicol, clindamycin or their analogs; provided that $R_1$ can not be desosamine;

$R_2$ and $R_3$ are each independently OH, or $R_2$ and $R_3$ are taken together as follows:

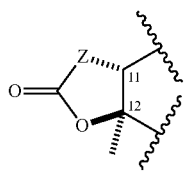

where Z is O, or —N(R$_6$); where R$_6$ is hydrogen, hydroxy, alkyl, aralkyl, alkylaryl, alkoxy, heteroalkyl, aryl, heteroaryl, dimethylaminoalkyl, acyl, or sulfonyl, ureyl or carbamoyl and pharmaceutically acceptable salts thereof.

X is H;

Y is OR$_7$; where R$_7$ is a monosaccharide or disaccharide (including aminosugars or halosugars), alkyl, aryl, heteroaryl, acyl (particularly, 4-nitrophenylacetyl and 2-pyridylacetyl), or —C(O)—NR$_8$R$_9$, where R$_8$ and R$_9$ can be independently or taken together as hydrogen, hydroxy, alkyl, aralkyl, alkylaryl, heteroalkyl, aryl, heteroaryl, alkoxy, dimethylaminoalkyl, acyl, sulfonyl, ureyl or carbamyl and pharmaceutically acceptable salts thereof, or X and Y taken together are O;

V is —C(O)—, —C(=NR$_{11}$)—, —C(NR$_{12}$,R$_{13}$)—, or —N(R$_{14}$)CH$_2$—, wherein the first dash of each of the foregoing V groups is attached to the C-10 carbon of the compounds of Formulae 1 and 2 and the last dash of each group is attached to the C-8 carbon of the compounds of Formulae 1 and 2 and R$_{11}$ is hydroxy or alkoxy, R$_{12}$ and R$_{13}$ can be independently or taken together as hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof and R$_{14}$ is hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof;

W is H, F, Cl, Br, I, or OH;

A is —CH$_2$—, —C(O)—, —C(O)O—, —C(O)NH—, —S(O)$_2$—, —S(O)$_2$NH—, —C(O)NHS(O)$_2$—;

B is —(CH$_2$)$_n$— where n is an integer ranging from 0-10, or B is an unsaturated carbon chain of 2-10 carbons, which may contain any alkenyl or alkynyl group; and C is hydrogen, hydroxy, alkyl, aralkyl, alkylaryl, alkoxy, heteroalkyl, aryl, heteroaryl, aminoaryl, alkylaminoaryl, acyl, acyloxy, sulfonyl, ureyl or carbamoyl and pharmaceutically acceptable salts thereof; wherein R$_{10}$ is hydrogen or acyl.

In yet another aspect, the present invention provides pharmaceutical compositions for the treatment of disorder(s) selected from the group consisting of a viral infection, bacterial infection, a protozoal infection, or a disorder related to a bacterial infection or protozoal infection in a mammal, fish or bird which comprises a therapeutically effective amount of a compound of Formula 1 and Formula 2, their pharmaceutically acceptable salts, hydrates, solvates, esters and prodrugs thereof and a pharmaceutically acceptable carrier, wherein:

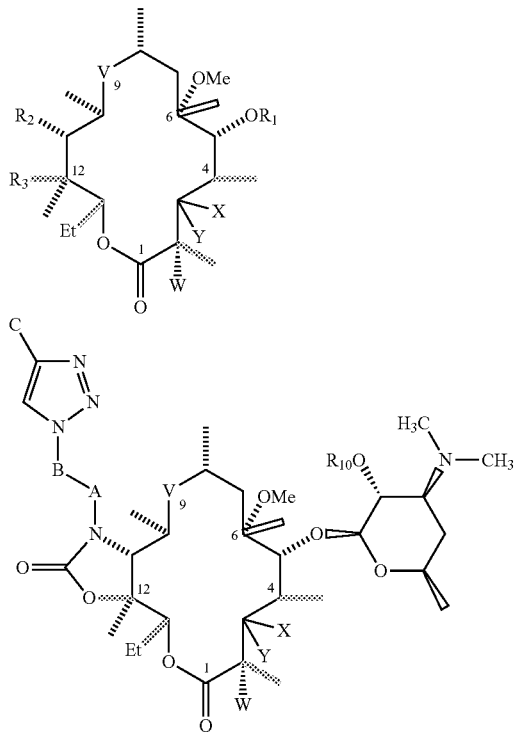

R$_1$ is selected from H, cyclic and acyclic alkyl, cyclic and acyclic alkyl-hydroxyamine, aryl, aryl-hydroxyamine, cyclic and acyclic acyl, cyclic and acyclic acyl-hydroxyamine, heteroalkyl, heteroalkyl-hydroxyamine, heteroaryl, heteroaryl-hydroxyamine, acylaryl, acylaryl-hydroxyamine, acylheteroaryl, acylheteroaryl-hydroxyamine, alkylaryl, alkylaryl-hydroxyamine, alkylheteroaryl, alkylheteroaryl-hydroxyamine, sulfonylalkyl, sulfonylalkyl-hydroxyamine, acylalkoxylsulfonylalkyl, acylalkoxylsulfonylalkyl-hydroxyamine;

or R$_1$ can be —C(O)—NR$_4$R$_5$, where R$_4$ and R$_5$ can be independently or taken together as hydrogen, hydroxy, alkyl, aralkyl, alkylaryl, alkoxy, heteroalkyl, aryl, heteroaryl, dimethylaminoalkyl, acyl, sulfonyl, urea or carbamate and acceptable salts thereof;

or R$_1$ can also be a monosaccharide (including amino sugars and their derivatives, particularly, a mycaminose derivatized at the C-4' position or a 4-deoxy-3-amino-glucose derivatized at the C-6' position), a disaccharide (including, a mycaminose derivatized at the C-4' position with another sugar or a 4-deoxy-3-amino-glucose derivatized at the C-6' position with another sugar), a trisaccharide (including aminosugars and halosugars), chloramphenicol, clindamycin or their analogs; provided that R$_1$ can not be desosamine;

R$_2$ and R$_3$ are each independently OH, or R$_2$ and R$_3$ are taken together as follows:

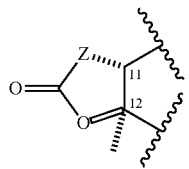

where Z is O, or —N(R₆); where R₆ is hydrogen, hydroxy, alkyl, aralkyl, alkylaryl, alkoxy, heteroalkyl, aryl, heteroaryl, dimethylaminoalkyl, acyl, or sulfonyl, ureyl or carbamoyl and pharmaceutically acceptable salts thereof;

wherein X is H;

Y is OR₇; where R₇ is a monosaccharide or disaccharide (including aminosugars or halosugars), alkyl, aryl, heteroaryl, acyl (particularly, 4-nitrophenylacetyl and 2-pyridylacetyl), or —C(O)—NR₈R₉, where R₈ and R₉ can be independently or taken together as hydrogen, hydroxy, alkyl, aralkyl, alkylaryl, heteroalkyl, aryl, heteroaryl, alkoxy, dimethylaminoalkyl, acyl, sulfonyl, ureyl or carbamyl and pharmaceutically acceptable salts thereof, or X and Y taken together are O;

V is —C(O)—, —C(=NR₁₁)—, —C(NR₁₂,R₁₃)—, or —N(R₁₄)CH₂—, wherein the first dash of each of the foregoing V groups is attached to the C-10 carbon of the compounds of Formulae 1 and 2 and the last dash of each group is attached to the C-8 carbon of the compounds of Formulae 1 and 2 and R₁₁ is hydroxy or alkoxy, R₁₂ and R₁₃ can be independently or taken together as hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof and R₁₄ is hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof;

W is H, F, Cl, Br, I, or OH;

A is —CH₂—, —C(O)—, —C(O)O—, —C(O)NH—, —S(O)₂—, —S(O)₂NH—, —C(O)NHS(O)₂—;

B is —(CH₂)ₙ— where n is an integer ranging from 0-10, or B is an unsaturated carbon chain of 2-10 carbons, which may contain any alkenyl or alkynyl group; and C is hydrogen, hydroxy, alkyl, aralkyl, alkylaryl, alkoxy, heteroalkyl, aryl, heteroaryl, aminoaryl, alkylaminoaryl, acyl, acyloxy, sulfonyl, ureyl or carbamoyl and pharmaceutically acceptable salts thereof; wherein R₁₀ is hydrogen or acyl.

In yet another aspect, the present invention provides a method of treating a disorder selected from the group consisting of a viral infection or bacterial infection, a protozoal infection, or disorder related to a bacterial infection or protozoal infection in a mammal, fish or bird which comprises administering through any route of administration, to said mammal, fish, or bird a therapeutically effective amount of a compound of Formula 1 and Formula 2, their pharmaceutically acceptable salts, hydrates, solvates, esters and prodrugs thereof and a pharmaceutically acceptable carrier, wherein:

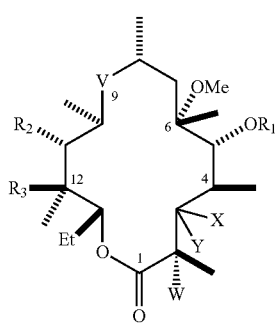

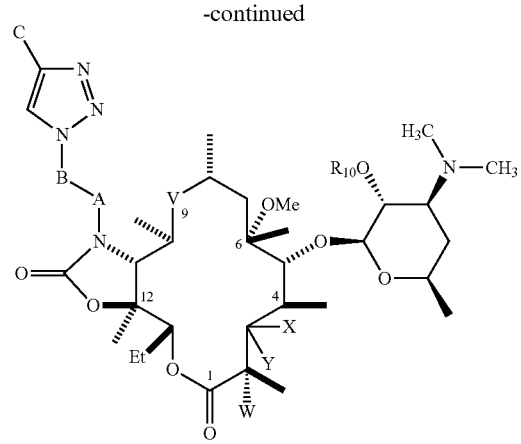

R₁ is selected from H, cyclic and acyclic alkyl, cyclic and acyclic alkyl-hydroxyamine, aryl, aryl-hydroxyamine, cyclic and acyclic acyl, cyclic and acyclic acyl-hydroxyamine, heteroalkyl, heteroalkyl-hydroxyamine, heteroaryl, heteroaryl-hydroxyamine, acylaryl, acylaryl-hydroxyamine, acylheteroaryl, acylheteroaryl-hydroxyamine, alkylaryl, alkylaryl-hydroxyamine, alkylheteroaryl, alkylheteroaryl-hydroxyamine, sulfonylalkyl, sulfonylalkyl-hydroxyamine, acylalkoxylsulfonylalkyl, acylalkoxylsulfonylalkyl-hydroxyamine;

or R₁ can be —C(O)—NR₄R₅, where R₄ and R₅ can be independently or taken together as hydrogen, hydroxy, alkyl, aralkyl, alkylaryl, alkoxy, heteroalkyl, aryl, heteroaryl, dimethylaminoalkyl, acyl, sulfonyl, urea or carbamate and acceptable salts thereof;

or R₁ can also be a monosaccharide (including amino sugars and their derivatives, particularly, a mycaminose derivatized at the C-4' position or a 4-deoxy-3-amino-glucose derivatized at the C-6' position), a disaccharide (including, a mycaminose derivatized at the C-4' position with another sugar or a 4-deoxy-3-amino-glucose derivatized at the C-6' position with another sugar), a trisaccharide (including aminosugars and halosugars), chloramphenicol, clindamycin or their analogs; provided that R₁ can not be desosamine;

R₂ and R₃ are each independently OH, or R₂ and R₃ are taken together as follows:

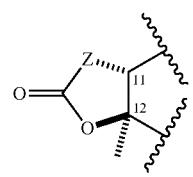

where Z is O, or —N(R₆); where R₆ is hydrogen, hydroxy, alkyl, aralkyl, alkylaryl, alkoxy, heteroalkyl, aryl, heteroaryl, dimethylaminoalkyl, acyl, or sulfonyl, ureyl or carbamoyl and pharmaceutically acceptable salts thereof;

X is H;

Y is OR₇; where R₇ is a monosaccharide or disaccharide (including aminosugars or halosugars), alkyl, aryl, heteroaryl, acyl (particularly, 4-nitrophenylacetyl and 2-pyridylacetyl), or —C(O)—NR₈R₉, where R₈ and R₉ can be independently or taken together as hydrogen, hydroxy, alkyl, aralkyl, alkylaryl, heteroalkyl, aryl, heteroaryl, alkoxy, dimethylaminoalkyl, acyl, sulfonyl, ureyl or carbamyl and pharmaceutically acceptable salts thereof, or X and Y taken together are O;

V is —C(O)—, —C(=NR$_{11}$)—, —C(NR$_{12}$,R$_{13}$)—, or —N(R$_{14}$)CH$_2$—, wherein the first dash of each of the foregoing V groups is attached to the C-10 carbon of the compounds of Formulae 1 and 2 and the last dash of each group is attached to the C-8 carbon of the compounds of Formulae 1 and 2 and R$_{11}$ is hydroxy or alkoxy, R$_{12}$ and R$_{13}$ can be independently or taken together as hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof and R$_{14}$ is hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof;

W is H, F, Cl, Br, I, or OH;

A is —CH$_2$—, —C(O)—, —C(O)O—, —C(O)NH—, —S(O)$_2$—, —S(O)$_2$NH—, —C(O)NHS(O)$_2$—;

B is —(CH$_2$)$_n$— where n is an integer ranging from 0-10, or B is an unsaturated carbon chain of 2-10 carbons, which may contain any alkenyl or alkynyl group; and C is hydrogen, hydroxy, alkyl, aralkyl, alkylaryl, alkoxy, heteroalkyl, aryl, heteroaryl, aminoaryl, alkylaminoaryl, acyl, acyloxy, sulfonyl, ureyl or carbamoyl and pharmaceutically acceptable salts thereof; wherein R$_{10}$ is hydrogen or acyl.

In yet another aspect, the present invention provides a disinfectant having the structure of Formula 1 and Formula 2 or their acceptable salts, hydrates or solvates thereof, wherein:

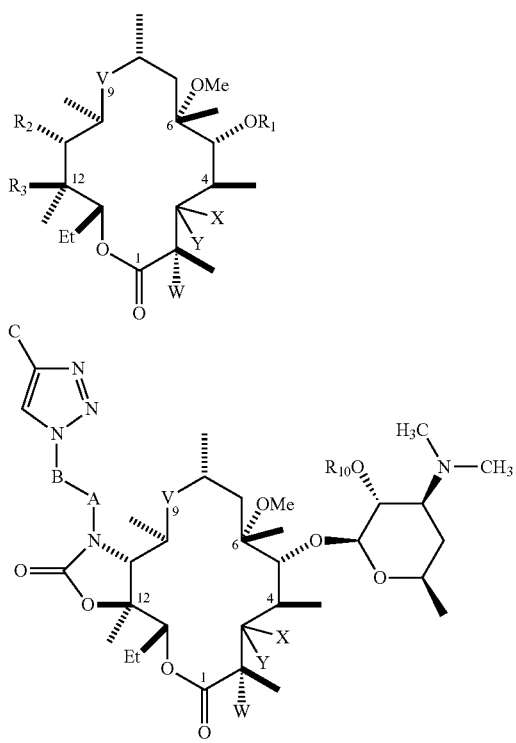

R$_1$ is selected from H, cyclic and acyclic alkyl, cyclic and acyclic alkyl-hydroxyamine, aryl, aryl-hydroxyamine, cyclic and acyclic acyl, cyclic and acyclic acyl-hydroxyamine, heteroalkyl, heteroalkyl-hydroxyamine, heteroaryl, heteroaryl-hydroxyamine, acylaryl, acylaryl-hydroxyamine, acylheteroaryl, acylheteroaryl-hydroxyamine, alkylaryl, alkylaryl-hydroxyamine, alkylheteroaryl, alkylheteroaryl-hydroxyamine, sulfonylalkyl, sulfonylalkyl-hydroxyamine, acylalkoxylsulfonylalkyl, acylalkoxylsulfonylalkyl-hydroxyamine;

or R$_1$ can be —C(O)—NR$_4$R$_5$, where R$_4$ and R$_5$ can be independently or taken together as hydrogen, hydroxy, alkyl, aralkyl, alkylaryl, alkoxy, heteroalkyl, aryl, heteroaryl, dimethylaminoalkyl, acyl, sulfonyl, urea or carbamate and acceptable salts thereof;

or R$_1$ can also be a monosaccharide (including amino sugars and their derivatives, particularly, a mycaminose derivatized at the C-4' position or a 4-deoxy-3-amino-glucose derivatized at the C-6' position), a disaccharide (including, a mycaminose derivatized at the C-4' position with another sugar or a 4-deoxy-3-amino-glucose derivatized at the C-6' position with another sugar), a trisaccharide (including aminosugars and halosugars), chloramphenicol, clindamycin or their analogs; provided that R$_1$ can not be desosamine;

R$_2$ and R$_3$ are each independently OH, or R$_2$ and R$_3$ are taken together as follows:

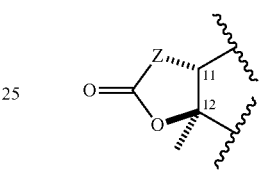

where Z is O, or —N(R$_6$); where R$_6$ is hydrogen, hydroxy, alkyl, aralkyl, alkylaryl, alkoxy, heteroalkyl, aryl, heteroaryl, dimethylaminoalkyl, acyl, or sulfonyl, ureyl or carbamoyl and pharmaceutically acceptable salts thereof;

X is H;

Y is OR$_7$; where R$_7$ is a monosaccharide or disaccharide (including aminosugars or halosugars), alkyl, aryl, heteroaryl, acyl (particularly, 4-nitrophenylacetyl and 2-pyridylacetyl), or —C(O)—NR$_8$R$_9$, where R$_8$ and R$_9$ can be independently or taken together as hydrogen, hydroxy, alkyl, aralkyl, alkylaryl, heteroalkyl, aryl, heteroaryl, alkoxy, dimethylaminoalkyl, acyl, sulfonyl, ureyl or carbamyl and pharmaceutically acceptable salts thereof, or X and Y taken together are O;

V is —C(O)—, —C(=NR$_{11}$)—, —C(NR$_{12}$,R$_{13}$)—, or —N(R$_{14}$)CH$_2$—, wherein the first dash of each of the foregoing V groups is attached to the C-10 carbon of the compounds of Formulae 1 and 2 and the last dash of each group is attached to the C-8 carbon of the compounds of Formulae 1 and 2 and R$_{11}$ is hydroxy or alkoxy, R$_{12}$ and R$_{13}$ can be independently or taken together as hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof and R$_{14}$ is hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof;

W is H, F, Cl, Br, I, or OH;

A is —CH$_2$—, —C(O)—, —C(O)O—, —C(O)NH—, —S(O)$_2$—, —S(O)$_2$NH—, —C(O)NHS(O)$_2$—;

B is —(CH$_2$)$_n$— where n is an integer ranging from 0-10, or B is an unsaturated carbon chain of 2-10 carbons, which may contain any alkenyl or alkynyl group; and C is hydrogen, hydroxy, alkyl, aralkyl, alkylaryl, alkoxy, heteroalkyl, aryl, heteroaryl, aminoaryl, alkylaminoaryl, acyl, acyloxy, sulfonyl, ureyl or carbamoyl and pharmaceutically acceptable salts thereof; wherein R$_{10}$ is hydrogen or acyl.

In yet another aspect, the present invention provides a pharmaceutical composition for the treatment of cancer, in particular non-small cell lung cancer, in a mammal, in particular a human, which comprises a therapeutically effective amount of a compound of Formula 1 and Formula 2, or their pharmaceutically acceptable salts, hydrates, solvates, esters and prodrugs thereof, and their pharmaceutically acceptable carriers, wherein:

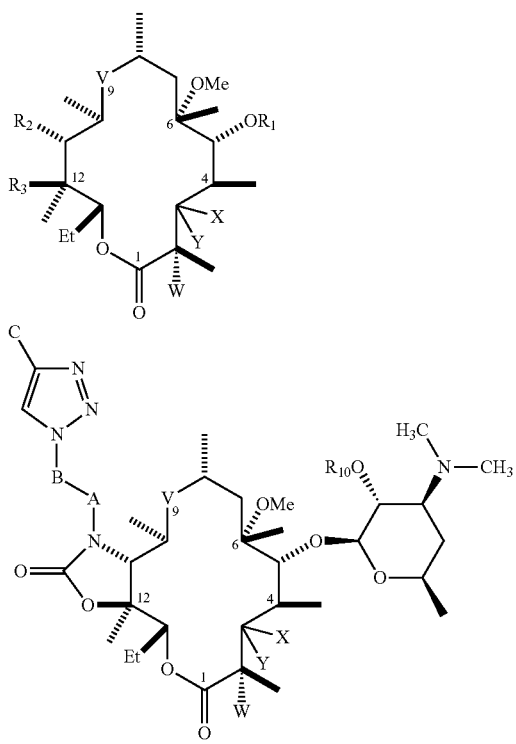

$R_1$ is selected from H, cyclic and acyclic alkyl, cyclic and acyclic alkyl-hydroxyamine, aryl, aryl-hydroxyamine, cyclic and acyclic acyl, cyclic and acyclic acyl-hydroxyamine, heteroalkyl, heteroalkyl-hydroxyamine, heteroaryl, heteroaryl-hydroxyamine, acylaryl, acylaryl-hydroxyamine, acylheteroaryl, acylheteroaryl-hydroxyamine, alkylaryl, alkylaryl-hydroxyamine, alkyheteroaryl, alkylheteroaryl-hydroxyamine, sulfonylalkyl, sulfonylalkyl-hydroxyamine, acylalkoxylsulfonylalkyl, acylalkoxylsulfonylalkyl-hydroxyamine;

or $R_1$ can be —C(O)—$NR_4R_5$, where $R_4$ and $R_5$ can be independently or taken together as hydrogen, hydroxy, alkyl, aralkyl, alkylaryl, alkoxy, heteroalkyl, aryl, heteroaryl, dimethylaminoalkyl, acyl, sulfonyl, urea or carbamate and acceptable salts thereof;

or $R_1$ can also be a monosaccharide (including amino sugars and their derivatives, particularly, a mycaminose derivatized at the C-4' position or a 4-deoxy-3-amino-glucose derivatized at the C-6' position), a disaccharide (including, a mycaminose derivatized at the C-4' position with another sugar or a 4-deoxy-3-amino-glucose derivatized at the C-6' position with another sugar), a trisaccharide (including aminosugars and halosugars), chloramphenicol, clindamycin or their analogs; provided that $R_1$ can not be desosamine;

$R_2$ and $R_3$ are each independently OH, or $R_2$ and $R_3$ are taken together as follows:

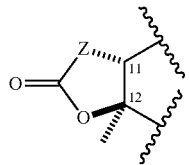

where Z is O, or —N($R_6$); where $R_6$ is hydrogen, hydroxy, alkyl, aralkyl, alkylaryl, alkoxy, heteroalkyl, aryl, heteroaryl, dimethylaminoalkyl, acyl, or sulfonyl, ureyl or carbamoyl and pharmaceutically acceptable salts thereof;

X is H;

Y is $OR_7$; where $R_7$ is a monosaccharide or disaccharide (including aminosugars or halosugars), alkyl, aryl, heteroaryl, acyl (particularly, 4-nitrophenylacetyl and 2-pyridylacetyl), or —C(O)—$NR_8R_9$, where $R_8$ and $R_9$ can be independently or taken together as hydrogen, hydroxy, alkyl, aralkyl, alkylaryl, heteroalkyl, aryl, heteroaryl, alkoxy, dimethylaminoalkyl, acyl, sulfonyl, ureyl or carbamyl and pharmaceutically acceptable salts thereof, or X and Y taken together are O;

V is —C(O)—, —C(=$NR_{11}$)—, —C($NR_{12}$,$R_{13}$)—, or —N($R_{14}$)$CH_2$—, wherein the first dash of each of the foregoing V groups is attached to the C-10 carbon of the compounds of Formulae 1 and 2 and the last dash of each group is attached to the C-8 carbon of the compounds of Formulae 1 and 2 and $R_{11}$ is hydroxy or alkoxy, $R_{12}$ and $R_{13}$ can be independently or taken together as hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof and $R_{14}$ is hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof;

W is H, F, Cl, Br, I, or OH;

A is —$CH_2$—, —C(O)—, —C(O)O—, —C(O)NH—, —S(O)$_2$—, —S(O)$_2$NH—, —C(O)NHS(O)$_2$—;

B is —(CH$_2$)$_n$— where n is an integer ranging from 0-10, or B is an unsaturated carbon chain of 2-10 carbons, which may contain any alkenyl or alkynyl group; and C is hydrogen, hydroxy, alkyl, aralkyl, alkylaryl, alkoxy, heteroalkyl, aryl, heteroaryl, aminoaryl, alkylaminoaryl, acyl, acyloxy, sulfonyl, ureyl or carbamoyl and pharmaceutically acceptable salts thereof; wherein $R_{10}$ is hydrogen or acyl.

In yet another aspect, the present invention provides a method of treating cancer, in particular non-small cell lung cancer in a mammal, in particular a human, which comprises administering to said mammal a therapeutically effective amount of a compound of Formula 1 and Formula 2, or their pharmaceutically acceptable salts, hydrates, solvates, esters and prodrugs thereof, and pharmaceutically acceptable carriers, wherein:

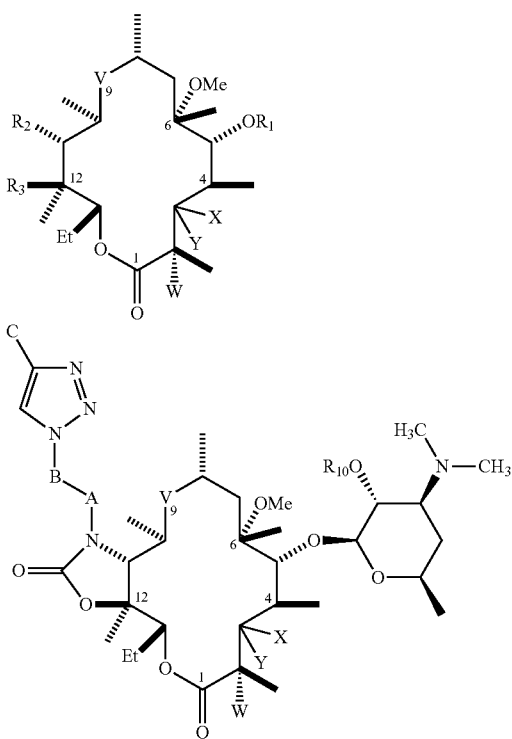

$R_1$ is selected from H, cyclic and acyclic alkyl, cyclic and acyclic alkyl-hydroxyamine, aryl, aryl-hydroxyamine, cyclic and acyclic acyl, cyclic and acyclic acyl-hydroxyamine, heteroalkyl, heteroalkyl-hydroxyamine, heteroaryl, heteroaryl-hydroxyamine, acylaryl, acylaryl-hydroxyamine, acylheteroaryl, acylheteroaryl-hydroxyamine, alkylaryl, alkylaryl-hydroxyamine, alkylheteroaryl, alkylheteroaryl-hydroxyamine, sulfonylalkyl, sulfonylalkyl-hydroxyamine, acylalkoxylsulfonylalkyl, acylalkoxylsulfonylalkyl-hydroxyamine;

or $R_1$ can be —C(O)—$NR_4R_5$, where $R_4$ and $R_5$ can be independently or taken together as hydrogen, hydroxy, alkyl, aralkyl, alkylaryl, alkoxy, heteroalkyl, aryl, heteroaryl, dimethylaminoalkyl, acyl, sulfonyl, urea or carbamate and acceptable salts thereof;

or $R_1$ can also be a monosaccharide (including amino sugars and their derivatives, particularly, a mycaminose derivatized at the C-4' position or a 4-deoxy-3-amino-glucose derivatized at the C-6' position), a disaccharide (including, a mycaminose derivatized at the C-4' position with another sugar or a 4-deoxy-3-amino-glucose derivatized at the C-6' position with another sugar), a trisaccharide (including aminosugars and halosugars), chloramphenicol, clindamycin or their analogs; provided that $R_1$ can not be desosamine;

$R_2$ and $R_3$ are each independently OH, or $R_2$ and $R_3$ are taken together as follows:

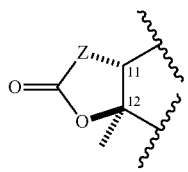

where Z is O, or —N($R_6$); where $R_6$ is hydrogen, hydroxy, alkyl, aralkyl, alkylaryl, alkoxy, heteroalkyl, aryl, heteroaryl, dimethylaminoalkyl, acyl, or sulfonyl, ureyl or carbamoyl and pharmaceutically acceptable salts thereof;

X is H;

Y is $OR_7$; where $R_7$ is a monosaccharide or disaccharide (including aminosugars or halosugars), alkyl, aryl, heteroaryl, acyl (particularly, 4-nitrophenylacetyl and 2-pyridylacetyl), or —C(O)—$NR_8R_9$, where $R_8$ and $R_9$ can be independently or taken together as hydrogen, hydroxy, alkyl, aralkyl, alkylaryl, heteroalkyl, aryl, heteroaryl, alkoxy, dimethylaminoalkyl, acyl, sulfonyl, ureyl or carbamyl and pharmaceutically acceptable salts thereof, or X and Y taken together are O;

V is —C(O)—, —C(=$NR_{11}$)—, —C($NR_{12},R_{13}$)—, or —N($R_{14}$)$CH_2$—, wherein the first dash of each of the foregoing V groups is attached to the C-10 carbon of the compounds of Formulae 1 and 2 and the last dash of each group is attached to the C-8 carbon of the compounds of Formulae 1 and 2 and $R_{11}$ is hydroxy or alkoxy, $R_{12}$ and $R_{13}$ can be independently or taken together as hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof and $R_{14}$ is hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof;

W is H, F, Cl, Br, I, or OH;

A is —$CH_2$—, —C(O)—, —C(O)O—, —C(O)NH—, —S(O)$_2$—, —S(O)$_2$NH—, —C(O)NHS(O)$_2$—;

B is —(CH$_2$)$_n$— where n is an integer ranging from 0-10, or B is an unsaturated carbon chain of 2-10 carbons, which may contain any alkenyl or alkynyl group; and C is hydrogen, hydroxy, alkyl, aralkyl, alkylaryl, alkoxy, heteroalkyl, aryl, heteroaryl, aminoaryl, alkylaminoaryl, acyl, acyloxy, sulfonyl, ureyl or carbamoyl and pharmaceutically acceptable salts thereof; wherein $R_{10}$ is hydrogen or acyl.

In yet another aspect, the present invention provides a method for preventing, inhibiting, or stopping the growth of bacteria, for example, on or in a surface, which comprises applying to a surface an effective amount of an antibacterial agent having the structure of Formula 1 and Formula 2 or their acceptable salts, hydrates or solvates thereof, wherein:

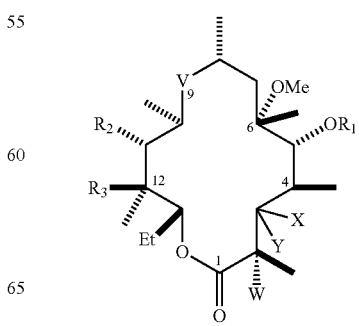

-continued

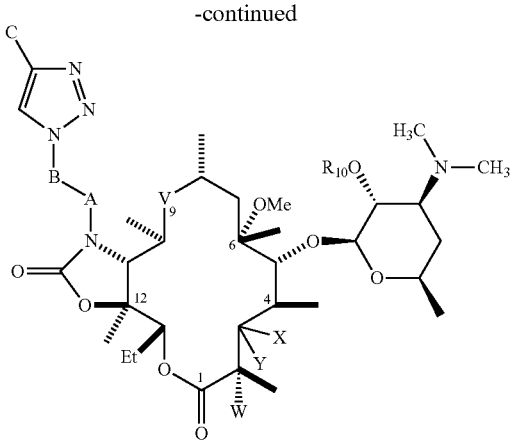

R$_1$ is selected from H, cyclic and acyclic alkyl, cyclic and acyclic alkyl-hydroxyamine, aryl, aryl-hydroxyamine, cyclic and acyclic acyl, cyclic and acyclic acyl-hydroxyamine, heteroalkyl, heteroalkyl-hydroxyamine, heteroaryl, heteroaryl-hydroxyamine, acylaryl, acylaryl-hydroxyamine, acylheteroaryl, acylheteroaryl-hydroxyamine, alkylaryl, alkylaryl-hydroxyamine, alkylheteroaryl, alkylheteroaryl-hydroxyamine, sulfonylalkyl, sulfonylalkyl-hydroxyamine, acylalkoxylsulfonylalkyl, acylalkoxylsulfonylalkyl-hydroxyamine;

or R$_1$ can be —C(O)—NR$_4$R$_5$, where R$_4$ and R$_5$ can be independently or taken together as hydrogen, hydroxy, alkyl, aralkyl, alkylaryl, alkoxy, heteroalkyl, aryl, heteroaryl, dimethylaminoalkyl, acyl, sulfonyl, urea or carbamate and acceptable salts thereof;

or R$_1$ can also be a monosaccharide (including amino sugars and their derivatives, particularly, a mycaminose derivatized at the C-4' position or a 4-deoxy-3-amino-glucose derivatized at the C-6' position), a disaccharide (including, a mycaminose derivatized at the C-4' position with another sugar or a 4-deoxy-3-amino-glucose derivatized at the C-6' position with another sugar), a trisaccharide (including aminosugars and halosugars), chloramphenicol, clindamycin or their analogs; provided that R$_1$ can not be desosamine;

R$_2$ and R$_3$ are each independently OH, or R$_2$ and R$_3$ are taken together as follows:

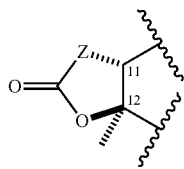

where Z is O, or —N(R$_6$); where R$_6$ is hydrogen, hydroxy, alkyl, aralkyl, alkylaryl, alkoxy, heteroalkyl, aryl, heteroaryl, dimethylaminoalkyl, acyl, or sulfonyl, ureyl or carbamoyl and pharmaceutically acceptable salts thereof;

X is H;

Y is OR$_7$; where R$_7$ is a monosaccharide or disaccharide (including aminosugars or halosugars), alkyl, aryl, heteroaryl, acyl (particularly, 4-nitrophenylacetyl and 2-pyridylacetyl), or —C(O)—NR$_8$R$_9$, where R$_8$ and R$_9$ can be independently or taken together as hydrogen, hydroxy, alkyl, aralkyl, alkylaryl, heteroalkyl, aryl, heteroaryl, alkoxy, dimethylaminoalkyl, acyl, sulfonyl, ureyl or carbamyl and pharmaceutically acceptable salts thereof, or X and Y taken together are O;

V is —C(O)—, —C(=NR$_{11}$)—, —C(NR$_{12}$R$_{13}$)—, or —N(R$_{14}$)CH$_2$—, wherein the first dash of each of the foregoing V groups is attached to the C-10 carbon of the compounds of Formulae 1 and 2 and the last dash of each group is attached to the C-8 carbon of the compounds of Formulae 1 and 2 and R$_{11}$ is hydroxy or alkoxy, R$_{12}$ and R$_{13}$ can be independently or taken together as hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof and R$_{14}$ is hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof;

W is H, F, Cl, Br, I, or OH;

A is —CH$_2$—, —C(O)—, —C(O)O—, —C(O)NH—, —S(O)$_2$—, —S(O)$_2$NH—, —C(O)NHS(O)$_2$—;

B is —(CH$_2$)$_n$— where n is an integer ranging from 0-10, or B is an unsaturated carbon chain of 2-10 carbons, which may contain any alkenyl or alkynyl group; and C is hydrogen, hydroxy, alkyl, aralkyl, alkylaryl, alkoxy, heteroalkyl, aryl, heteroaryl, aminoaryl, alkylaminoaryl, acyl, acyloxy, sulfonyl, ureyl or carbamoyl and pharmaceutically acceptable salts thereof; wherein R$_{10}$ is hydrogen or acyl.

DETAILED DESCRIPTION OF THE INVENTION

All documents including patent, publications and patent applications referred to herein are hereby incorporated by reference in their entireties. The compounds of the present invention may be prepared, for example, according to the schemes and examples provided below. Unless otherwise indicated, the substituents of the compounds in the schemes are defined as described below.

The present invention provides novel classes of aglycones and, particularly, macrolide compounds of Formula 1 to which are introduced a variety of monosaccharide or oligosaccharide building blocks at 5-OH sites, rendering potential pharmaceutical agents for preventing or treating antibacterial infections and antibiotic drug resistance.

The present invention also provides novel classes of macrolide antibiotics with the Formula 2 bearing a 1,2,3 triazole ring linked via a spacer to 11,12 carbamate around a 14-membered macrolide core rendering potential pharmaceutical agents for preventing or treating bacterial infections and antibiotic drug resistance.

A compound of Formula 1 and Formula 2 includes compounds having the following structures or their pharmaceutically acceptable salts, esters or prodrugs thereof, and optionally including a pharmaceutically acceptable carrier:

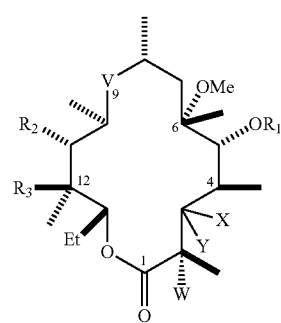

-continued

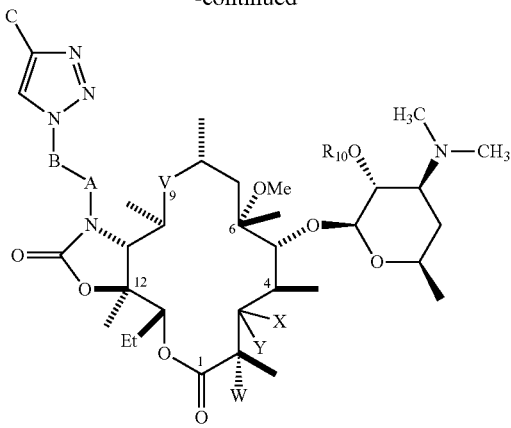

wherein R₁ is selected from H, cyclic and acyclic alkyl, cyclic and acyclic alkyl-hydroxyamine, aryl, aryl-hydroxyamine, cyclic and acyclic acyl, cyclic and acyclic acyl-hydroxyamine, heteroalkyl, heteroalkyl-hydroxyamine, heteroaryl, heteroaryl-hydroxyamine, acylaryl, acylaryl-hydroxyamine, acylheteroaryl, acylheteroaryl-hydroxyamine, alkylaryl, alkylaryl-hydroxyamine, alkylheteroaryl, alkylheteroaryl-hydroxyamine, sulfonylalkyl, sulfonylalkyl-hydroxyamine, acylalkoxylsulfonylalkyl, acylalkoxylsulfonylalkyl-hydroxyamine;

or R₁ can be —C(O)—NR₄R₅, where R₄ and R₅ can be independently or taken together as hydrogen, hydroxy, alkyl, aralkyl, alkylaryl, alkoxy, heteroalkyl, aryl, heteroaryl, dimethylaminoalkyl, acyl, sulfonyl, urea or carbamate and acceptable salts thereof;

or R₁ can also be a monosaccharide (including amino sugars and their derivatives, particularly, a mycaminose derivatized at the C-4' position or a 4-deoxy-3-amino-glucose derivatized at the C-6' position), a disaccharide (including, a mycaminose derivatized at the C-4' position with another sugar or a 4-deoxy-3-amino-glucose derivatized at the C-6' position with another sugar), a trisaccharide (including aminosugars and halosugars), chloramphenicol, clindamycin or their analogs; provided that R₁ can not be desosamine;

R₂ and R₃ are each independently OH, or R₂ and R₃ are taken together as follows:

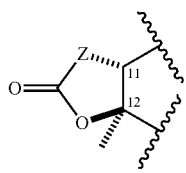

where Z is O, or —N(R₆); where R₆ is hydrogen, hydroxy, alkyl, aralkyl, alkylaryl, alkoxy, heteroalkyl, aryl, heteroaryl, dimethylaminoalkyl, acyl, or sulfonyl, ureyl or carbamoyl and pharmaceutically acceptable salts thereof;

X is H;

Y is OR₇; where R₇ is a monosaccharide or disaccharide (including aminosugars or halosugars), alkyl, aryl, heteroaryl, acyl (particularly, 4-nitrophenylacetyl and 2-pyridylacetyl), or —C(O)—NR₈R₉, where R₈ and R₉ can be independently or taken together as hydrogen, hydroxy, alkyl, aralkyl, alkylaryl, heteroalkyl, aryl, heteroaryl, alkoxy, dimethylaminoalkyl, acyl, sulfonyl, ureyl or carbamyl and pharmaceutically acceptable salts thereof, or X and Y taken together are O;

V is —C(O)—, —C(=NR₁₁)—, —C(NR₁₂R₁₃)—, or —N(R₁₄)CH₂—, wherein the first dash of each of the foregoing V groups is attached to the C-10 carbon of the compounds of Formulae 1 and 2 and the last dash of each group is attached to the C-8 carbon of the compounds of Formulae 1 and 2 and R₁₁ is hydroxy or alkoxy, R₁₂ and R₁₃ can be independently or taken together as hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof and R₁₄ is hydrogen, hydroxy, alkyl, aralkyl, alkylaryl, alkoxy, heteroalkyl, aryl, heteroaryl, dimethylaminoalkyl, acyl, sulfonyl, ureyl or carbamoyl and pharmaceutically acceptable salts thereof;

W is H, F, Cl, Br, I, or OH;

A is —CH₂—, —C(O)—, —C(O)O—, —C(O)NH—, —S(O)₂—, —S(O)₂NH—, —C(O)NHS(O)₂—;

B is —(CH₂)ₙ— where n is an integer ranging from 0-10, or B is an unsaturated carbon chain of 2-10 carbons, which may contain any alkenyl or alkynyl group; and C is hydrogen, hydroxy, alkyl, aralkyl, alkylaryl, alkoxy, heteroalkyl, aryl, heteroaryl, aminoaryl, alkylaminoaryl, acyl, acyloxy, sulfonyl, ureyl or carbamoyl and pharmaceutically acceptable salts thereof; wherein R₁₀ is hydrogen or acyl.

DEFINITIONS

The compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 Recommendations for Section E, Fundamental Stereochemistry, Pure Appl. Chem. (1976) 45, 13-30.

The term "treating" as used herein, unless otherwise indicated, means reversing, alleviating, inhibiting the progress of, or preventing the disorder or condition to which such term applies, or one or more symptoms of such disorder or condition. The term "treatment" as used herein, refers to the act of treating, as "treating" is defined immediately above.

The compositions containing the compound(s) of the invention can be administered for prophylactic and/or therapeutic treatments. In therapeutic applications, the compositions are administered to a patient already suffering from an infection, as described above, in an amount sufficient to cure or at least partially arrest the infection and/or its symptoms. An amount adequate to accomplish this is defined as "therapeutically effective amount or dose." Amounts effective for this use will depend on the severity and course of the infection, previous therapy, the patient's health status and response to the drugs, and the judgment of the treating physician. In prophylactic applications, compositions containing the compounds of the invention are administered to a patient susceptible to or otherwise at risk of a particular infection. Such an amount is defined to be a "prophylactically effective amount or dose." In this use, the precise amounts again depend on the patient's state of health, weight, and the like.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In general, a suitable effective dose of the compound of the invention will be in the range of 0.1 to 5000 milligram (mg) per recipient per day, preferably in the range of 1 to 1000 mg per day, more preferably in the range of 10 to 200 mg per day. The desired dosage is preferably presented in one, two, three, four or more subdoses administered at appropriate intervals throughout the day. These subdoses can be administered as unit dosage forms, for example, containing 5 to 1000 mg, preferably 10 to 100 mg of active ingredient per unit dosage form. Preferably, the compounds of the invention will be administered in amounts of between about 1.0 mg/kg to 250 mg/kg of patient body weight, between about one to four times per day.

The term "carbon chain" means a plurality of carbon atoms covalently bonded to one another. The chain may be alkyl, alkenyl, alkynyl, heteroalkyl, heteroalkenyl, or heteroalkynyl, aromatic, conjugated, branched, unbranched, substituted, cyclic, or combinations thereof. If part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining chain length. As noted above, the carbon chain may also contain one or more heteroatoms, i.e., atoms other than carbon. If the chain contains heteroatoms as part of the backbone, those atoms are not calculated as part of the carbon chain length.

A "pharmacological composition" or "pharmaceutical composition" refers to a mixture of one or more of the compounds described herein, or physiologically acceptable salts thereof, with other chemical components, such as physiologically acceptable carriers and/or excipients. The purpose of a pharmacological composition is to facilitate administration of a compound to an organism.

"Pharmaceutically acceptable salts" of the compounds of the invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, gluconic, lactic, salicylic, succinic, toluene-p-sulfonic, tartaric, acetic, citric, methanesulfonic, formic, benzoic, malonic, naphthalene-2-sulfonic, benzenesulfonic, 1,2 ethanesulfonic acid (edisylate), galactosyl-d-gluconic acid, and the like. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—$(C_1-C_4$ alkyl$)_4^+$ salts, and the like. Illustrative examples of some of these include sodium hydroxide, potassium hydroxide, choline hydroxide, sodium carbonate, and the like.

A "physiologically acceptable carrier" refers to a carrier or diluent that does not cause significant irritation to an organism and does not abrogate the biological activity and properties of the administered compound.

An "excipient" refers to an inert substance added to a pharmacological composition to further facilitate administration of a compound. Examples of excipients include but are not limited to calcium carbonate, calcium phosphate, various sugars and types of starch, cellulose derivatives, gelatin, vegetable oils and polyethylene glycols.

The term "alkyl," alone or in combination, refers to an optionally substituted straight-chain, optionally substituted branched-chain, or optionally substituted cyclic alkyl radical having from 1 to about 30 carbons, more preferably 1 to 12 carbons. Examples of alkyl radicals include methyl, ethyl, n-propyl, isopropyl, n-butyl, isobutyl, sec-butyl, tert-butyl, tert-amyl, pentyl, hexyl, heptyl, octyl and the like. The term "cycloalkyl" embraces cyclic configurations, is subsumed within the definition of alkyl and specifically refers to a monocyclic, bicyclic, tricyclic, and higher multicyclic alkyl radicals wherein each cyclic moiety has from 3 to about 8 carbon atoms. Examples of cycloalkyl radicals include cyclopropyl, cyclobutyl, cyclopentyl, cyclohexyl and the like. A "lower alkyl" is a shorter alkyl, e.g., one containing from 1 to about 6 carbon atoms.

The term "alkenyl," alone or in combination, refers to an optionally substituted straight-chain, optionally substituted branched-chain, or optionally substituted cyclic alkenyl hydrocarbon radical having one or more carbon-carbon double-bonds and having from 2 to about 30 carbon atoms, more preferably 2 to about 18 carbons. Examples of alkenyl radicals include ethenyl, propenyl, butenyl, 1,4-butadienyl and the like. The term can also embrace cyclic alkenyl structures. A "lower alkenyl" refers to an alkenyl having from 2 to about 6 carbons.

The term "alkynyl," alone or in combination, refers to an optionally substituted straight-chain, optionally substituted branched-chain, or cyclic alkynyl hydrocarbon radical having one or more carbon-carbon triple-bonds and having from 2 to about 30 carbon atoms, more preferably 2 to about 12 carbon atoms. The term also includes optionally substituted straight-chain or optionally substituted branched-chain hydrocarbon radicals having one or more carbon-carbon triple bonds and having from 2 to about 6 carbon atoms as well as those having from 2 to about 4 carbon atoms. Examples of alkynyl radicals include ethynyl, propynyl, butynyl and the like.

The terms heteroalkyl, heteroalkenyl and heteroalkynyl include optionally substituted alkyl, alkenyl and alkynyl structures, as described above, and which have one or more skeletal chain atoms selected from an atom other than carbon, e.g., oxygen, nitrogen, sulfur, phosphorus or combinations thereof.

The term "carbon chain" may embrace any alkyl, alkenyl, alkynyl, or heteroalkyl, heteroalkenyl, or heteroalkynyl group, and may be linear, cyclic, or any combination thereof. If part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining chain length. If the chain contains heteroatoms as part of the backbone, those atoms are not calculated as part of the carbon chain length.

The term "alkoxy," alone or in combination, refers to an alkyl ether radical, alkyl-O—, wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "aryloxy," alone or in combination, refers to an aryl ether radical wherein the term aryl is defined as below. Examples of aryloxy radicals include phenoxy, benzyloxy and the like.

The term "alkylthio," alone or in combination, refers to an alkyl thio radical, alkyl-S—, wherein the term alkyl is defined as above.

The term "arylthio," alone or in combination, refers to an aryl thio radical, aryl-S—, wherein the term aryl is defined as below.

The term "aryl," alone or in combination, refers to an optionally substituted aromatic ring system. The term aryl includes monocyclic aromatic rings, polyaromatic rings and polycyclic aromatic ring systems containing from six to about twenty carbon atoms. The term aryl also includes monocyclic aromatic rings, polyaromatic rings and polycyclic ring systems containing from 6 to about 12 carbon atoms, as well as those containing from 6 to about 10 carbon atoms. The polyaromatic and polycyclic aromatic rings systems may contain from two to four rings. Examples of aryl groups include, without limitation, phenyl, biphenyl, naphthyl and anthryl ring systems.

The term "heteroaryl" refers to optionally substituted aromatic ring systems containing from about five to about 20 skeletal ring atoms and having one or more heteroatoms such as, for example, oxygen, nitrogen, sulfur, selenium and phosphorus. The term heteroaryl also includes optionally substituted aromatic ring systems having from 5 to about 12 skeletal ring atoms, as well as those having from 5 to about 10 skeletal ring atoms. The term heteroaryl may include five- or six-membered heterocyclic rings, polycyclic heteroaromatic ring systems and polyheteroaromatic ring systems where the ring system has two, three or four rings. The terms heterocyclic, polycyclic heteroaromatic and polyheteroaromatic include ring systems containing optionally substituted heteroaromatic rings having more than one heteroatom as described above (e.g., a six membered ring with two nitrogens), including polyheterocyclic ring systems of from two to four rings. The term heteroaryl includes ring systems such as, for example, furanyl, benzofuranyl, chromenyl, pyridyl, pyrrolyl, indolyl, quinolinyl, N-alkyl pyrrolyl, pyridyl-N-oxide, pyrimidoyl, pyrazinyl, imidazolyl, pyrazolyl, oxazolyl, benzothiophenyl, purinyl, indolizinyl, thienyl and the like, all optionally substituted.

The term "heteroarylalkyl" refers to a C1-C4 alkyl group containing a heteroaryl group, each of which may be optionally substituted.

The term "heteroaryithio" refers to the group —S-heteroaryl.

The term "aralkyl" refers to an alkyl group substituted with an aryl group. Suitable aralkyl groups include benzyl, picolyl, and the like, and may be optionally substituted.

The term "alkylaryl" refers to an aryl group substituted with an alkyl group.

The term "amino" refers to —NRR' where R and R' are independently selected from hydrogen, alkyl, aryl, aralkyl, all except H are optionally substituted; and R and R' can form a cyclic ring system.

The term "aminoalkyl" refers to the group —N(R)-alk where "alk" is an alkyl group and R is selected from H, alkyl, aryl, and aralkyl.

The term "ureyl" or "urea" refers to the group $R^1R^2N$—C(O)—$NR^3R^4$ where $R^1$, $R^2$, $R^3$ and $R^4$ are independently selected from hydrogen, alkyl, aryl, aralkyl, all except H are optionally substituted; and $R^1$-$R^2$, $R^3$-$R^4$, $R^1$-$R^3$ or $R^2$-$R^4$ can form a cyclic ring system.

The term "carbamyl" or "carbamate" refers to the group R—O—C(O)—$NR^1R^2$ where R is alkyl, aryl, aralkyl, alkylaryl; and $R^1$ and $R^2$ are independently selected from hydrogen, alkyl, aryl, aralkyl, all except H are optionally substituted; and $R^1$ and $R^2$ can form a cyclic ring system.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "perhalo" refers to groups wherein every C—H bond has been replaced with a C-halo bond on an aliphatic or aryl group. Suitable perhaloalkyl groups include —$CF_3$ and —$CFCl_2$.

The term "carbocycle" includes optionally substituted, saturated or unsaturated, three- to eight-membered cyclic structures in which all of the skeletal atoms are carbon.

The term "heterocyclic" refers to cyclic group of 3 to 10 atoms, more preferably 3 to 6 atoms, containing at least one heteroatom, preferably 1 to 3 heteroatoms. Suitable heteroatoms include oxygen, sulfur, and nitrogen. Heterocyclic groups may be attached through a nitrogen or through a carbon atom in the ring. The heterocyclic groups include unsaturated cyclic, fused cyclic and spirocyclic groups. Suitable heterocyclic groups include pyrrolidinyl, morpholino, and morpholinoethyl. Heterocycles can be substituted or unsubstituted with one, two, three, four or five substituents independently selected from amino, alkylamino, halogen, alkylacylamino, alkyl, aryl or alkoxy.

The term "sulfonyl" refers to —$SO_2R$ where R is H, alkyl or aryl.

The term "sugar building block" refers to a saccharide group.

The term "saccharide group" refers to an oxidized, reduced or substituted saccharide monoradical covalently attached via any atom of the saccharide moiety, preferably via the aglycon carbon atom. A saccharide refers to a carbohydrate which is a polyhydroxy aldehyde or ketone, or derivative thereof, having the empirical formula $(CH_2O)_n$ wherein n is a whole integer, typically greater than 3. Monosaccharides, or simple sugars, consist of a single polyhydroxy aldehyde or ketone unit. Representative monosaccharides include, by way of illustration only, hexoses such as D-glucose, D-mannose, D-xylose, D-galactose, L-fucose, and the like; pentoses such as D-ribose or D-arabinose and ketoses such as D-ribulose or D-fructose. Disaccharides contain two monosaccharide units joined by a glycosidic linkage. Disaccharides include, for example, sucrose, lactose, maltose, cellobiose, and the like. Oligosaccharides typically contain from 2 to 10 monosaccharide units joined by glycosidic linkages. Polysaccharides (glycans) typically contain more than 10 such units and include, but are not limited to, molecules such as heparin, heparan sulfate, chondroitin sulfate, dermatan sulfate and polysaccharide derivatives thereof. The term "sugar" generally refers to mono-, di- or oligosaccharides. A saccharide may be substituted, for example, glucosamine, galactosamine, acetylglucose, acetylgalactose, N-acetylglucosamine, N-acetyl-galactosamine, galactosyl-N-acetylglucosamine, N-acetylneuraminic acid (sialic acid), etc., as well as sulfated and phosphorylated sugars. For the purposes of this definition, the saccharides can be either in their open or preferably in their pyranose form.

The term "amino-containing saccharide group" refers to a saccharide group having at least one amino substituent. Representative amino-containing saccharides include mycaminose, desosamine, L-vancosamine, 3-desmethyl-vancosamine, 3-epi-vancosamine, 4-epi-vancosamine, acosamine, 3-amino-glucose, 4-deoxy-3-amino-glucose, actinosamine, daunosamine, 3-epi-daunosamine, ristosamine, N-methyl-D-glucamine and the like.

The term "halosugar" refers to a saccharide group having at least one halogen substituent.

The term "acyloxy" refers to the ester group —OC(O)—R, where R is H, alkyl, alkenyl, alkynyl, aryl, or arylalkyl, wherein the alkyl, alkenyl, alkynyl and arylalkyl groups may be optionally substituted.

The term "carboxy esters" refers to —C(O)OR where R is alkyl, aryl or arylalkyl, wherein the alkyl, aryl and arylalkyl groups may be optionally substituted.

The term "carboxamido" refers to

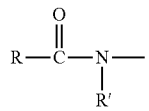

where each of R and R' are independently selected from the group consisting of H, alkyl, aryl and arylalkyl, wherein the alkyl, aryl and arylalkyl groups may be optionally substituted.

The term "arylalkyl," alone or in combination, refers to an alkyl radical as defined above in which one H atom is replaced by an aryl radical as defined above, such as, for example, benzyl, 2-phenylethyl and the like.

The terms haloalkyl, haloalkenyl, haloalkynyl and haloalkoxy include alkyl, alkenyl, alkynyl and alkoxy structures, as described above, that are substituted with one or more fluorines, chlorines, bromines or iodines, or with combinations thereof.

The terms cycloalkyl, aryl, arylalkyl, heteroaryl, alkyl, alkynyl, alkenyl, haloalkyl and heteroalkyl include optionally substituted cycloalkyl, aryl, arylalkyl, heteroaryl, alkyl, alkynyl, alkenyl, haloalkyl and heteroalkyl groups.

The term "carbocycle" includes optionally substituted, saturated or unsaturated, three- to eight-membered cyclic structures in which all of the skeletal atoms are carbon.

The term "membered ring" can embrace any cyclic structure, including carbocycles and heterocycles as described above. The term "membered" is meant to denote the number of skeletal atoms that constitute the ring. Thus, for example, pyridine, pyran, and thiopyran are 6 membered rings and pyrrole, furan, and thiophene are 5 membered rings.

The term "acyl" includes alkyl, aryl, heteroaryl, arylalkyl or heteroarylalkyl substituents attached to a compound via a carbonyl functionality (e.g., —CO-alkyl, —CO-aryl, —CO-arylalkyl or —CO-heteroarylalkyl, etc.).

The term "alkylacylamino" as used herein refers to an alkyl radical appended to an acylamino group.

The term "acylamino" as used herein refers to an acyl radical appended to an amino group.

The term "substituted heterocycle" or heterocyclic group" as used herein refers to any 3, or 4-membered ring containing a heteroatom selected from nitrogen, oxygen, phosphorus and sulfur or a 5- or 6-membered ring containing from one to three heteroatoms selected from the group consisting of nitrogen, oxygen, phosphorus and sulfur; wherein the 5-membered ring has 0-2 double bounds and the 6-membered ring has 0-3 double bounds; wherein the nitrogen and sulfur atom maybe optionally oxidized; wherein the nitrogen and sulfur heteroatoms maybe optionally quarternized; and including any bicyclic group in which any of the above heterocyclic rings is fused to a benzene ring or another 5- or 6-membered heterocyclic ring independently defined above. Heterocyclics can be unsubstituted or monosubstituted or disubstituted with substituents independently selected from hydroxy, halo, oxo (C=O), alkylimino (RN=wherein R is a alkyl group), amino, alkylamino, dialkylamino, acylaminoalkyl, alkoxy, thioalkoxy, polyalkoxy, alkyl, cycloalkyl or haloalkyl. Examples of heterocyclics include: imidazolyl, pyridyl, piperazinyl, azetidinyl, thiazolyl and triazolyl.

"Optionally substituted" groups may be substituted or unsubstituted. The substituents of an "optionally substituted" group may include, without limitation, one or more substituents, more typically one to four, independently selected from the following groups or designated subsets thereof: alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, carboxyesters, carboxamido, acyloxy, H, F, Cl, Br, I, CN, $NO_2$, $NH_2$, $N_3$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$, $C(O)NH_2$, pyridinyl, thiophene, furanyl, indole, indazole, esters, amides, phosphonates, phosphates, phosphoramides, sulfonates, sulfates, sulfonamides, carbamates, ureas, thioureas, thioamides, thioalkyls. "Substituted aryl" and "substituted heteroaryl" preferably refers to aryl and heteroaryl groups substituted with 1-3 substituents. Preferably these substituents are selected from the group consisting of lower alkyl, lower alkoxy, lower perhaloalkyl, halo, hydroxy, and amino. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$).

The term "halogen" includes F, Cl, Br and I.

The term "isomeric mixture" means a mixture of two or more configurationally distinct chemical species having the same chemical formula. An isomeric mixture is genus comprising individual isomeric species. Examples of isomeric mixtures include stereoisomers (enantiomers, diastereomers), regioisomers, as might result for example from a pericyclic reaction. The compounds of the present invention comprise asymmetrically substituted carbon atoms. Such asymmetrically substituted carbon atoms can result in mixtures of stereoisomers at a particular asymmetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 Recommendations for Section E, Fundamental Stereochemistry, *Pure Appl. Chem.* (1976) 45, 13-30.

The methods disclosed in the present invention may result in the preparation of different regioisomers and or stereoisomers. This event is not intended to lessen the usefulness of the presently disclosed methods, rather isomeric mixtures may be more readily tested than separated isomeric species. Easily prepared mixtures of two or more stereoisomers or regioisomers may be separated if testing of isomeric mixtures indicates that one or more active species is present.

Prodrugs

The term "prodrug" as used herein refers to any compound that when administered to a biological system generates a biologically active compound as a result of spontaneous chemical reaction(s), enzyme-catalyzed chemical reaction(s), and/or metabolic chemical reaction(s), or a combination of each. Standard prodrugs are formed using groups attached to functionality, e.g. HO—, HS—, HOOC—, $R_2N$—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of Formula 1 and Formula 2 fall within the scope of the present invention. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. The biologically active compounds include, but are not limited to antibiotic agents, anticancer agents, antiviral agents, and agents for treating gastric motility disorders.

Prodrugs contain a chemical moiety, e.g., an amide or phosphorus group whose function is to endow enhanced solubility and/or stability to the attached drug so that it can be effectively preserved/delivered to a host. Once in the body, the prodrug is typically acted upon by an enzyme in vivo, e.g., an esterase, amidase, or phosphatase, to liberate/generate the more pharmacologically active drug. This activation may occur through the action of an endogenous host enzyme or a non-endogenous enzyme that is administered to the host preceding, following, or during administration of the prodrug. Prodrug use in general is further discussed, e.g., in U.S. Pat. No. 5,627,165, as well as in Pathak et al., *Enzymic protecting group techniques in organic synthesis*, Stereosel. Biocatal. 775-797 (2000), and is otherwise well known in the art, although not to Applicants' knowledge using the specific compounds and compositions claimed herein.

Ideally, the prodrug should be converted to the original drug as soon as the goal is achieved, followed by the subsequent rapid elimination of the released derivatizing group. The term can also mean a nonspecific chemical approach to mask undesirable drug properties or improve drug delivery. For example, many therapeutic drugs have undesirable properties that may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, etc.). The prodrug approach, a chemical approach using reversible derivatives, can be useful in the optimization of the clinical application of a drug.

Pharmaceutical Compositions/Formulations, Dosaging, and Modes of Administration

Those of ordinary skill in the art are familiar with formulation and administration techniques, e.g., as discussed in Goodman and Gilman's The Pharmacological Basis of Therapeutics, current edition; Pergamon Press; and Remington's Pharmaceutical Sciences (current edition.) Mack Publishing Co., Easton, Pa. These techniques can be employed in appropriate aspects and embodiments of the invention.

The compounds utilized in the methods of the instant invention may be administered either alone or in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

For example, the therapeutic or pharmaceutical compositions of the invention can be administered locally to the area in need of treatment. This may be achieved by, for example, but not limited to, local infusion during surgery, topical application, e.g., cream, ointment, injection, catheter, or implant, said implant made, e.g., out of a porous, non-porous, or gelatinous material, including membranes, such as sialastic membranes, or fibers. The administration can also be by direct injection at the site (or former site) of a tumor or neoplastic or pre-neoplastic tissue.

Still further, the therapeutic or pharmaceutical composition can be delivered in a vesicle, e.g., a liposome (see, for example, Langer, 1990, Science, 249:1527-1533; Treat et al., 1989, Liposomes in the Therapy of Infectious Disease and Cancer, Lopez-Bernstein and Fidler (eds.), Liss, N.Y., pp. 353-365).

The pharmaceutical compositions used in the methods of the present invention can be delivered in a controlled release system. In one embodiment, a pump may be used (see, Sefton, 1987, CRC Crit. Ref. Biomed. Eng. 14:201; Buchwald et al., 1980, Surgery, 88:507; Saudek et al., 1989, N. Engl. J. Med., 321:574). Additionally, a controlled release system can be placed in proximity of the therapeutic target (see, Goodson, 1984, Medical Applications of Controlled Release, Vol. 2, pp. 115-138).

The pharmaceutical compositions used in the methods of the instant invention can contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the taste of the drug or delay disintegration and absorption in the gastrointestinal tract and thereby provide a sustained action over a longer period. For example, a water soluble taste masking material such as hydroxypropylmethyl cellulose or hydroxypropyl cellulose, or a time delay material such as ethyl cellulose, or cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions can contain the active material in admixture with excipients suitable for the manufacture of aqueous suspensions. Such excipients can act as suspending agents and include, e.g., sodium carboxymethyl cellulose, methyl cellulose, hydroxypropylmethyl cellulose, sodium alginate, polyvinyl pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant, e.g., butylated hydroxyanisol, alpha-tocopherol, or ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of antioxidant(s).

The pharmaceutical compositions used in the methods of the instant invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of composition suitable for use as an inhalant.

The pharmaceutical compositions may be in the form of a sterile injectable aqueous solution. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane-diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The macrolides used in the methods of the present invention may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing a macrolide can be used. As used herein, topical application can include mouthwashes and gargles.

The compounds used in the methods of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The methods and compounds of the instant invention may also be used in conjunction with other well known therapeutic agents that are selected for their particular usefulness against the condition that is being treated. For example, the instant compounds may be useful in combination with known anticancer and cytotoxic agents.

Preferably the pharmaceutical preparation is in unit dosage form. In such form, the preparation is subdivided into unit doses containing appropriate quantities of the active component, e.g., an amount that is effective to achieve the desired purpose.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the compounds used in the methods of the present invention and, if applicable, other chemotherapeutic agents will be regulated according to the judgment of the attending clinician (physician) considering such factors as age, condition and size of the patient as well as severity of the disease being treated.

In general, compounds of the invention and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician. The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the proliferative disease, the condition of the patient, and the actual choice of compounds used.

The determination of the order of administration, and the number of repetitions of administration of each therapeutic agent during a treatment protocol, is well within the knowledge of the skilled physician after evaluation of the disease being treated and the condition of the patient.

Representative compounds of the present invention of Formula 1 include, but are not limited to:

11-N-[4-(4-Pyridin-3-yl-imidazol-1-yl)-butyl]-6-O-methyl-5-O-(3-dimethylamino-2-hydroxy-propoxy)-3-oxo-erythronolide A, 11,12-carbamate;

11-N-[4-(4-Pyridin-3-yl-imidazol-1-yl)-butyl]-6-O-methyl-5-O-(3-dimethylamino-2-hydroxy-propionyl ester)-3-oxo-erythronolide A, 11,12-carbamate;

11-N-[4-(4-Pyridin-3-yl-imidazol-1-yl)-butyl]-6-O-methyl-5-O-mycaminosyl-3-oxo-erythronolide A, 11,12-carbamate;

11-N-[4-(4-Pyridin-3-yl-imidazol-1-yl)-butyl]-6-O-methyl-5-O-garosaminyl-3-oxo-erythronolide A, 11,12-carbamate;

11-N-[4-(4-Pyridin-3-yl-imidazol-1-yl)-butyl]-6-O-methyl-5-O-vancosaminyl-3-oxo-erythronolide A, 11,12-carbamate;

11-N-[4-(4-Pyridin-3-yl-imidazol-1-yl)-butyl]-6-O-methyl-5-O-(3-amino-erythrosyl)-3-oxo-erythronolide A, 11,12-carbamate 11-N-[4-(4-Pyridin-3-yl-imidazol-1-yl)-butyl]-6-O-methyl-5-O-(3-dimethylamino-ribofuranosyl)-3-oxo-erythronolide A, 11,12-carbamate;

11-N-[4-(4-Pyridin-3-yl-imidazol-1-yl)-butyl]-6-O-methyl-5-O-(3-dimethylamino-arabinofuranosyl)-3-oxo-erythronolide A, 11,12-carbamate;

11-N-[4-(4-Pyridin-3-yl-imidazol-1-yl)-butyl]-6-O-methyl-5-O-(3-dimethylamino-ribopyranosyl)-3-oxo-erythronolide A, 11,12-carbamate;

11-N-[4-(4-Pyridin-3-yl-imidazol-1-yl)-butyl]-6-O-methyl-5-O-(3-dimethylamino-arabinopyranosyl)-3-oxo-erythronolide A, 11,12-carbamate;

11-N-[4-(4-Pyridin-3-yl-imidazol-1-yl)-butyl]-6-O-methyl-5-O-(3-dimethylamino-allofuranosyl)-3-oxo-erythronolide A, 11,12-carbamate 11-N-[4-(4-Pyridin-3-yl-imidazol-1-yl)-butyl]-6-O-methyl-5-O-(3-dimethylamino-altrofuranosyl)-3-oxo-erythronolide A, 11,12-carbamate;

11-N-[4-(4-Pyridin-3-yl-imidazol-1-yl)-butyl]-6-O-methyl-5-O-(3-dimethylamino-glucofuranosyl)-3-oxo-erythronolide A, 11,12-carbamate;

11-N-[4-(4-Pyridin-3-yl-imidazol-1-yl)-butyl]-6-O-methyl-5-O-(3-dimethylamino-mannofuranosyl)-3-oxo-erythronolide A, 11,12-carbamate;

11-N-[4-(4-Pyridin-3-yl-imidazol-1-yl)-butyl]-6-O-methyl-5-O-(3-dimethylamino-allopyrannosyl)-3-oxo-erythronolide A, 11,12-carbamate;

11-N-[4-(4-Pyridin-3-yl-imidazol-1-yl)-butyl]-6-O-methyl-5-O-(3-dimethylamino-altropyranosyl)-3-oxo-erythronolide A, 11,12-carbamate;

11-N-[4-(4-Pyridin-3-yl-imidazol-1-yl)-butyl]-6-O-methyl-5-O-(3-dimethylamino-glucopyranosyl)-3-oxo-erythronolide A, 11,12-carbamate;

11-N-[4-(4-Pyridin-3-yl-imidazol-1-yl)-butyl]-6-O-methyl-5-O-(4-deoxy-3-dimethylamino-glucopyranosyl)-3-oxo-erythronolide A, 11,12-carbamate;

11-N-[4-(4-Pyridin-3-yl-imidazol-1-yl)-butyl]-6-O-methyl-5-O-(3-dimethylamino-glucopyranosyl)-3-oxo-2-fluoro-erythronolide A, 11,12-carbamate;

11-N-[4-(4-Pyridin-3-yl-imidazol-1-yl)-butyl]-6-O-methyl-5-O-(4-deoxy-3-dimethylamino-glucopyranosyl)-3-oxo-2-fluoro-erythronolide A, 11,12-carbamate;

11-N-[4-(4-Pyridin-3-yl-imidazol-1-yl)-butyl]-6-O-methyl-5-O-(3-dimethylamino-6-O-phenylester-glucopyranosyl)-3-oxo-2-fluoro-erythronolide A, 11,12-carbamate;

11-N-[4-(4-Pyridin-3-yl-imidazol-1-yl)-butyl]-6-O-methyl-5-O-(3-dimethylamino-6-O-methylester-glucopyranosyl)-3-oxo-erythronolide A, 11,12-carbamate;

11-N-[4-(4-Pyridin-3-yl-imidazol-1-yl)-butyl]-6-O-methyl-5-O-(3-dimethylamino-6-O-methylether-glucopyranosyl)-3-oxo-2-fluoro-erythronolide A, 11,12-carbamate;

11-N-[4-(4-Pyridin-3-yl-imidazol-1-yl)-butyl]-6-O-methyl-5-O-(3-dimethylamino-4-deoxy-6-O-acetyl-glucopyranosyl)-3-oxo-erythronolide A, 11,12-carbamate;

11-N-[4-(4-Pyridin-3-yl-imidazol-1-yl)-butyl]-6-O-methyl-5-O-(3-dimethylamino-4-deoxy-6-O-acetyl-glucopyranosyl)-3-oxo-2-fluoro-erythronolide A, 11,12-carbamate;

11-N-[4-(4-Pyridin-3-yl-imidazol-1-yl)-butyl]-6-O-methyl-5-O-(3-dimethylamino-4-deoxy-6-methylester-galactopyranosyl)-3-oxo-2-fluoro-erythronolide A, 11,12-carbamate;

11-N-[4-(4-Pyridin-3-yl-imidazo-1-yl)-butyl]-6-O-methyl-5-O-(3-dimethylamino-4-deoxy-6-phenylester-galactopyranosyl)-3-oxo-2-fluoro-erythronolide A, 11,12-carbamate;

11-N-[4-(4-Pyridin-3-yl-imidazol-1-yl)-butyl]-6-O-methyl-5-O-(3-dimethylamino-mannopyranosyl)-3-oxo-erythronolide A, 11,12-carbamate;

11-N-[4-(4-Pyridin-3-yl-imidazol-1-yl)-butyl]-6-O-methyl-5-O-(3-dimethylamino-threosyl)-3-oxo-erythronolide A, 11,12-carbamate 11-N-[4-(4-Pyridin-3-yl-imidazol-1-yl)-butyl]-6-O-methyl-5-O-(3-amino-xylofuranosyl)-3-oxo-erythronolide A, 11,12-carbamate;

11-N-[4-(4-Pyridin-3-yl-imidazol-1)-yl-butyl]-6-O-methyl-5-O-(3-dimethylamino-lyxofuranosyl)-3-oxo-erythronolide A, 11,12-carbamate;

11-N-[4-(4-Pyridin-3-yl-imidazol-1-yl)-butyl]-6-O-methyl-5-(3-dimethylamino-xylopyranosyl)-3-oxo-erythronolide A, 11,12-carbamate;

11-N-[4-(4-Pyridin-3-yl-imidazol-1-yl)-butyl]-6-O-methyl-5-O-(3-dimethylamino-lyxopyranosyl)-3-oxo-erythronolide A, 11,12-carbamate;

11-N-[4-(4-Pyridin-3-yl-imidazol-1-yl)-butyl]-6-O-methyl-5-O-(3-dimethylamino-gulofuranosyl)-3-oxo-erythronolide A, 11,12-carbamate 11-N-[4-(4-Pyridin-3-yl-imidazol-1-yl)-butyl]-6-O-methyl-5-O-(3-dimethylamino-idofuranosyl)-3-oxo-erythronolide A, 11,12-carbamate;

11-N-[4-(4-Pyridin-3-yl-imidazo-1-yl)-butyl]-6-O-methyl-5-O-(3-dimethylamino-galactofuranosyl)-3-oxo-erythronolide A, 11,12-carbamate;

11-N-[4-(4-Pyridin-3-yl-imidazol-1-yl)-butyl]-6-O-methyl-5-O-(3-dimethylamino-talofuranosyl)-3-oxo-erythronolide A, 11,12-carbamate;

11-N-[4-(4-Pyridin-3-yl-imidazol-1-yl)-butyl]-6-O-methyl-5-O-(3-dimethylamino-guloyrannosyl)-3-oxo-erythronolide A, 11,12-carbamate;

11-N-[4-(4-Pyridin-3-yl-imidazol-1-yl)-butyl]-6-O-methyl-5-O-(3-dimethylamino-idopyranosyl)-3-oxo-erythronolide A, 11,12-carbamate;

11-N-[4-(4-Pyridin-3-yl-imidazol-1-yl)-butyl]-6-O-methyl-5-O-(3-dimethylamino-galactopyranosyl)-3-oxo-erythronolide A, 11,12-carbamate;

11-N-[4-(4-Pyridin-3-yl-imidazol-1-yl)-butyl]-6-O-methyl-5-O-(3-dimethylamino-talopyranosyl)-3-oxo-erythronolide A, 11,12-carbamate;

11-N-[4-[4-(6-Amino-pyridin-2-yl)-[1,2,3]triazol-1-yl]-butyl]-6-O-methyl-5-O-(3-dimethylamino-6-O-acetylester-glucopyranosyl)-3-oxo-2-fluoro-erythronolide A, 11,12-carbamate;

11-N-[4-[4-(6-Amino-pyridin-2-yl)-[1,2,3]triazol-1-yl]-butyl]-6-O-methyl-5-O-(3-dimethylamino-6-O-methyl-ether-glucopyranosyl)-3-oxo-2-fluoro-erythronolide A, 11,12-carbamate;

11-N-[4-[4-(6-Amino-pyridin-2-yl)-[1,2,3]triazol-1-yl]-butyl]-6-O-methyl-5-O-(3-dimethylamino-6-O-phenylester-glucopyranosyl)-3-oxo-2-fluoro-erythronolide A, 11,12-carbamate;

11-N-[4-[4-(6-Amino-pyridin-2-yl)-[1,2,3]triazol-1-yl]-butyl]-6-O-methyl-5-O-(3-dimethylamino-glucopyranosyl)-3-oxo-2-fluoro-erythronolide A, 11,12-carbamate;

11-N-[4-[4-(6-Amino-pyridin-2-yl)-[1,2,3]triazol-1-yl]-butyl]-6-O-methyl-5-O-(3-dimethylamino-4-deoxy-6-O-acetylester-glucopyranosyl-3-oxo-2-fluoro-erythronolide A, 11,12-carbamate;

11-N-[4-[4-(6-Amino-pyridin-2-yl)-[1,2,3]triazol-1-yl]-butyl]-6-O-methyl-5-O-(3-dimethylamino-4-deoxy-6-O-methylether-glucopyranosyl)-3-oxo-2-fluoro-erythronolide A, 11,12-carbamate;

11-N-[4-[4-(6-Amino-pyridin-2-yl)-[1,2,3]triazol-1-yl]-butyl]-6-O-methyl-5-O-(3-dimethylamino-4-deoxy-6-O-phenylester-glucopyranosyl)-3-oxo-2-fluoro-erythronolide A, 11,12-carbamate;

11-N-[4-[4-(6-Amino-pyridin-2-yl)-[1,2,3]triazol-1-yl]-butyl]-6-O-methyl-5-O-(3-dimethylamino-4-deoxy-glucopyranosyl)-3-oxo-2-fluoro-erythronolide A, 11,12-carbamate;

11-N-[4-[4-(6-Amino-pyridin-2-yl)-[1,2,3]triazol-1-yl]-butyl]-6-O-methyl-5-O-mycaminosyl-3-oxo-2-fluoro-erythronolide A, 11,12-carbamate;

11-N-[4-(4-Benzothiazol-1-ylmethyl-[1,2,3]triazol-1-yl)-butyl]-6-O-methyl-5-O-mycaminosyl-3-oxo-erythronolide A, 11,12-carbamate;

11-N-[4-(4-Benzotriazol-1-ylmethyl-[1,2,3]triazol-1-yl)-butyl]-6-O-methyl-5-O-garosaminyl-3-oxo-erythronolide A, 11,12-carbamate;

11-N-[4-(4-Benzotriazol-1-ylmethyl-[1,2,3]triazol-1-yl)-butyl]-6-O-methyl-5-O-vancosaminyl-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-erythrosyl)-3-oxo-erythronolide A, 11,12-carbamate 11-N-[4-(4-Benzotriazol-1-ylmethyl-[1,2,3]triazol-1-yl)-butyl]-6-O-methyl-5-O-(3-dimethylamino-ribofuranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-arabinofuranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-ribopyranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-arabinopyranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-allofuranosyl)-3-oxo-erythronolide A, 11,12-carbamate 11-N-[4-(4-Benzotriazol-1-ylmethyl-[1,2,3]triazol-1-yl)-butyl]-6-O-methyl-5-O-(3-dimethylamino-altrofuranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-glucofuranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-mannofuranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-allopyrannosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-altropyranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-glucopyranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-mannopyranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-threosyl)-3-oxo-erythronolide A, 11,12-carbamate 11-N-[4-(4-Benzotriazol-1-ylmethyl-[1,2,3]triazol-1-yl)-butyl]-6-O-methyl-5-O-(3-dimethylamino-xylofuranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-lyxofuranosyl)-3-oxo-erythronolide A, 11,12-carbamate;

11-N-[4-(4-Benzotriazol-1-ylmethyl-[1,2,3]triazol-1-yl-butyl]-6-O-methyl-5-O-(3-dimethylamino-xylopyranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-lyxopyranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-gulofuranosyl)-3-oxo-erythronolide A, 11,12-carbamate 11-N-[4-(4-Benzotriazol-1-ylmethyl-[1,2,3]triazol-1-yl)-butyl]-6-O-methyl-5-O-(3-dimethylamino-idofuranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-galactofuranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-talofuranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-guloyrannosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-idopyranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-galactopyranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-talopyranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-galactopyranosyl)-3-oxo-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-glucopyransyl)-3-oxo-2-fluoro-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-4-deoxy-glucopyransyl)-3-oxo-2-fluoro-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-4-deoxy-6-methylester-glucopyransyl)-3-oxo-2-fluoro-erythronolide A, 11,12-carbamate;

11-N-[4-(4-Benzotriazol-1-ylmethyl-[1,2,3]triazol-1-yl-butyl]-6-O-methyl-5-O-(3-dimethylamino-4-deoxy-6-O-methylether-glucopyransyl)-3-oxo-2-fluoro-erythronolide A, 11,12-carbamate;

11-N-[4-(4-Benzotriazol-1-ylmethyl-[1,2,3]triazol-1-yl)-butyl]-6-O-methyl-5-O-(3-dimethylamino-4-deoxy-6-O-phenylester-glucopyransyl)-3-oxo-2-fluoro-erythronolide A, 11,12-carbamate;

11-N-[4-(2-pyridyl-1-ylmethyl-[1,2,3]triazol-1-yl)-butyl]-6-O-methyl-5-O-(3-dimethylamino-glucopyransyl)-3-oxo-erythronolide A, 11,12-carbamate;

11-N-[4-(2-pyridyl-1-ylmethyl-[1,2,3]triazol-1-yl)-butyl]-6-O-methyl-5-O-(3-dimethylamino-glucopyransyl)-3-oxo-2-fluoro-erythronolide A, 11,12-carbamate;

11-N-[4-(2-pyridyl-1-ylmethyl-[1,2,3]triazol-1-yl)-butyl]-6-O-methyl-5-O-(3-dimethylamino-4-deoxy-glucopyransyl)-3-oxo-erythronolide A, 11,12-carbamate;

11-N-[4-(2-pyridyl-1-ylmethyl-[1,2,3]triazol-1-yl)-butyl]-6-O-methyl-5-O-(3-dimethylamino-4-deoxy-glucopyransyl)-3-oxo-2-fluoro-erythronolide A, 11,12-carbamate;

11-N-[4-(2-pyridyl-1-ylmethyl-[1,2,3]triazol-1-yl)-butyl]-6-O-methyl-5-O-(3-dimethylamino-4-deoxy-6-O-phenylester-glucopyransyl)-3-oxo-2-fluoro-erythronolide A, 11,12-carbamate;

11-N-[4-(2-pyridyl-1-ylmethyl-[1,2,3]triazol-1-yl)-butyl]-6-O-methyl-5-O-(3-dimethylamino-4-deoxy-6-O-methylester-glucopyransyl)-3-oxo-2-fluoro-erythronolide A, 11,12-carbamate;

11-N-[4-(2-pyridyl-1-ylmethyl-[1,2,3]triazol-1-yl)-butyl]-6-O-methyl-5-O-(3-dimethylamino-4-deoxy-6-O-methylether-glucopyransyl)-3-oxo-2-fluoro-erythronolide A, 11,12-carbamate;

11-N-[4-(2-pyridyl-1-ylmethyl-[1,2,3]triazol-1-yl)-butyl]-6-O-methyl-5-O-mycaminosyl-3-oxo-erythronolide A, 11,12-carbamate;

11-N-[4-(2-pyridyl-1-ylmethyl-[1,2,3]triazol-1-yl)-butyl]-6-O-methyl-5-O-mycaminosyl-3-oxo-2-fluoro-erythronolide A, 11,12-carbamate;

11-N-[4-(3-amino-phenyl-1-ylmethyl-[1,2,3]triazol-1-yl)-butyl]-6-O-methyl-5-O-(3-dimethylamino-glucopyransyl)-3-oxo-erythronolide A, 11,12-carbamate;

11-N-[4-(3-amino-phenyl-1-ylmethyl-[1,2,3]triazol-1-yl)-butyl]-6-O-methyl-5-O-(3-dimethylamino-glucopyransyl)-3-oxo-2-fluoro-erythronolide A, 11,12-carbamate;

11-N-[4-(3-amino-phenyl-1-ylmethyl-[1,2,3]triazol-1-yl)-butyl]-6-O-methyl-5-O-(3-dimethylamino-4-deoxy-glucopyransyl)-3-oxo-2-fluoro-erythronolide A, 11,12-carbamate;

11-N-[4-(3-amino-phenyl-1-ylmethyl-[1,2,3]triazol-1-yl)-butyl]-6-O-methyl-5-O-(3-dimethylamino-4-deoxy-6-O-methylester-glucopyransyl)-3-oxo-2-fluoro-erythronolide A, 11,12-carbamate;

11-N-[4-(3-amino-phenyl-1-ylmethyl-[1,2,3]triazol-1-yl)-butyl]-6-O-methyl-5-O-(3-dimethylamino-4-deoxy-6-O-phenylester-glucopyransyl)-3-oxo-2-fluoro-erythronolide A, 111,12-carbamate;

11-N-[4-(3-amino-phenyl-1-ylmethyl-[1,2,3]triazol-1-yl)-butyl]-6-O-methyl-5-O-(3-dimethylamino-4-deoxy-6-O-methylether-glucopyransyl)-3-oxo-2-fluoro-erythronolide A, 11,12-carbamate;

11-N-[4-(3-acetimido-phenyl-1-ylmethyl-[1,2,3]triazol-1-yl)-butyl]-6-O-methyl-5-O-(3-dimethylamino-glucopyransyl)-3-oxo-2-fluoro-erythronolide A, 11,12-carbamate;

11-N-[4-(3-acetimido-phenyl-1-ylmethyl-[1,2,3]triazol-1-yl)-butyl]-6-O-methyl-5-O-(3-dimethylamino-4-deoxy-glucopyransyl)-3-oxo-2-fluoro-erythronolide A, 11,12-carbamate;

11-N-[4-(3-acetimido-phenyl-1-ylmethyl-[1,2,3]triazol-1-yl)-butyl]-6-O-methyl-5-O-(3-dimethylamino-4-deoxy-6-O-methylester-glucopyransyl)-3-oxo-2-fluoro-erythronolide A, 11,12-carbamate;

11-N-[4-(4-Benzoimidazol-1-ylmethyl-[1,2,3]triazol-1-yl)-butyl]-6-O-methyl-5-O-mycaminosyl-3-oxo-erythronolide A, 11,12-carbamate;

11-N-[4-(4-Benzoimidazol-1-ylmethyl-[1,2,3]triazol-1-yl)-butyl]-6-O-methyl-5-O-garosaminyl-3-oxo-erythronolide A, 11,12-carbamate;

11-N-[4-(4-Benzoimidazol-1-ylmethyl-[1,2,3]triazol-1-yl)-butyl]-6-O-methyl-5-O-vancosaminyl-3-oxo-erythronolide A, 11,12-carbamate;

11-N-[4-(4-Benzoimidazol-1-ylmethyl-[1,2,3]triazol-1-yl)-butyl]-6-O-methyl-5-O-dimethylamino-erythrosyl)-3-oxo-erythronolide A, 11,12-carbamate 11-N-[4-(4-Benzoimidazol-1-ylmethyl-[1,2,3]triazol-1-yl)-butyl]-6-O-methyl-5-O-(3-dimethylamino-ribofuranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-arabinofuranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-ribopyranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-arabinopyranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-allofuranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-altrofuranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-glucofuranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-mannofuranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-allopyrannosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-altropyranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-glucopyranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-mannopyranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-threosyl)-3-oxo-erythronolide A, 11,12-carbamate 11-N-[4-(4-Benzoimidazol-1-ylmethyl-[1,2,3]triazol-1-yl)-butyl]-6-O-methyl-5-O-(3-dimethylamino-xylofuranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-lyxofuranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-xylopyranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-lyxopyranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-gulofuranosyl)-3-oxo-erythronolide A, 11,12-carbamate 11-N-[4-(4-Benzoimidazol-1-ylmethyl-[1,2,3]triazol-1-yl)-butyl]-6-O-methyl-5-O-(3-dimethylamino-idofuranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-galactofuranosyl)-3-oxo-erythronolide A, 111,12-carbamate;

11-N-[4-(4-Benzoimidazol-1-ylmethyl-[1,2,3]triazol-1-yl)-butyl]-6-O-methyl-5-O-(3-dimethylamino-talofuranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-guloyrannosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-idopyranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-galactopyranosyl)-3-oxo-erythronolide A, 11,12-carbamate;

11-N-[4-(4-Benzoimidazol-1-ylmethyl-[1,2,3]triazol-1-yl)-butyl]-6-O-methyl-5-O-(3-dimethylamino-talopyranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-mycaminosyl-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-garosaminyl-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-vancosaminyl-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-erythrosyl)-3-oxo-erythronolide A, 11,12-carbamate;

11-N-[4-(4-imidazo[4,5-b]pyridin-3-ylmethyl-[1,2,3]triazol-1-yl)-butyl]-6-O-methyl-5-O-(3-dimethylamino-ribofuranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-arabinofuranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-ribopyranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-arabinopyranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-allofuranosyl)-3-oxo-erythronolide A, 11,12-carbamate 11-N-[4-(4-Imidazo[4,5-b]pyridin-3-ylmethyl-[1,2,3]triazol-1-yl)-butyl]-6-O-methyl-5-O-(3-dimethylamino-altrofuranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-glucofuranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-mannofuranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-allopyrannosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-altropyranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-glucopyranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-mannopyranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-threosyl)-3-oxo-erythronolide A, 11,12-carbamate 11-N-[4-(4-Imidazo[4,5-b]pyridin-3-ylmethyl-[1,2,3]triazol-1-yl)-butyl]-6-O-methyl-5-O-(3-dimethylamino-xylofuranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-lyxofuranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-xylopyranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-lyxopyranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-gulofuranosyl)-3-oxo-erythronolide A, 11,12-carbamate 11-N-[4-(4-Imidazo[4,5-b]pyridin-3-ylmethyl-[1,2,3]triazol-1-yl)-butyl]-6-O-methyl-5-O-(3-dimethylamino-idofuranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-galactofuranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-talofuranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-guloyrannosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-idopyranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-galactopyranosyl)-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-(3-dimethylamino-talopyranosyl)-3-oxo-erythronolide A, 11,12-carbamate;

and their pharmaceutically acceptable salts, hydrates, solvates, esters and prodrugs thereof.

Representative compounds of the present invention of Formula 2 include, but are not limited to:

11-N-[4-(4-Imidazo[4,5-b]pyridin-3-ylmethyl-[1,2,3]triazol-1-yl)-butyl]-6-O-methyl-5-O-dasosaminyl-3-oxo-erythronolide A, 11,12-carbamate;

11-N-[4-(4-Imidazo[4,5-b]pyridin-3-ylmethyl-[1,2,3]triazol-1-yl)-butyl]-6-O-methyl-5-O-dasosaminyl-2-fluoro-3-oxo-erythronolide A, 11,12-carbamate;

11-N-[4-(4-Benzoimidazol-1-ylmethyl-[1,2,3]triazol-1-yl)-butyl]-6-O-methyl-5-O-dasosaminyl-3-oxo-erythronolide A, 11,12-carbamate;

11-N-[4-(4-Benzoimidazol-1-ylmethyl-[1,2,3]triazol-1-yl)-butyl]-6-O-methyl-5-O-dasosaminyl-2-fluoro-3-oxo-erythronolide A, 11,12-carbamate;

11-N-{2-[4-(4-n-Pentylphenyl)-[1,2,3]triazol-1-yl]-6-O-methyl-5-O-dasosamnyl 3-oxo-erythronolide A, 11,12-cyclic carbonate.

11-N-{2-[4-(4-n-Pentylphenyl)-[1,2,3]triazol-1-yl]-6-O-methyl-5-O-dasosamnyl 2-fluoro-3-oxo-erythronolide A, 11,12-cyclic carbonate.

11-N-{4-[4-(2,6-Dichlorophenoxyoxymethyl)-[1,2,3]triazol-1-yl]-butyl}-6-O-methyl-5-O-dasosaminyl-3-oxo-erythronolide A, 11,12-cyclic carbamate.

11-N-{4-[4-(2,6-Dichlorophenoxyoxymethyl)-[1,2,3]triazol-1-yl]-butyl}-6-O-methyl-5-O-dasosaminyl-2-fluoro-3-oxo-erythronolide A, 11,12-cyclic carbamate.

11-N-(3-amino-phenyl-1-ylmethyl-[1,2,3]triazol-1-yl]-butyl}-5-O-desosaminyl-3-oxo-erythronolide A,-11,12-cyclic carbamate.

11-N-(3-amino-phenyl-1-ylmethyl-[1,2,3]triazol-1-yl]-butyl}-5-O-desosaminyl-2-fluoro-3-oxo-erythronolide A,-11,12-cyclic carbamate.

11-N-[4-(2-pyridyl-1-ylmethyl-[1,2,3]triazol-1-yl)-butyl]-6-O-methyl-5-O-desosaminyl-3-oxo-erythronolide A, 11,12-carbamate;

11-N-[4-(2-pyridyl-1-ylmethyl-[1,2,3]triazol-1-yl)-butyl]-6-O-methyl-5-O-desosaminyl-2-fluoro-3-oxo-erythronolide A, 11,12-carbamate;

11-N-{4-[4-(6-Amino-pyridin-2-yl)-[1,2,3]triazol-1-yl]-butyl}-5-O-desosaminyl-3-oxo-erythronolide A,-11,12-cyclic carbamate.

11-N-{4-[4-(6-Amino-pyridin-2-yl)-[1,2,3]triazol-1-yl]-butyl}-5-O-desosaminyl-2-fluoro-3-oxo-erythronolide A,-11,12-cyclic carbamate.

and their pharmaceutically acceptable salts, hydrates, solvates, esters and prodrugs thereof.

Preparation of Compounds

The compounds of Formula 1 may be prepared according to Schemes 1 below and the description that follows. All other substituents, including X, Y, $R_1$, $R_2$, $R_3$, V and W are as defined in the Summary of the Invention unless otherwise indicated.

The compounds of the invention are readily prepared. Referring to Scheme 1, the starting compounds of Formulas 5 may be prepared from Erythromycin A, according to one or more methods familiar to those skilled in the art including the synthetic methods described by U.S. Pat. Nos. 5,635,485 and 6,028,181, both of which are hereby incorporated by reference.

Scheme 1

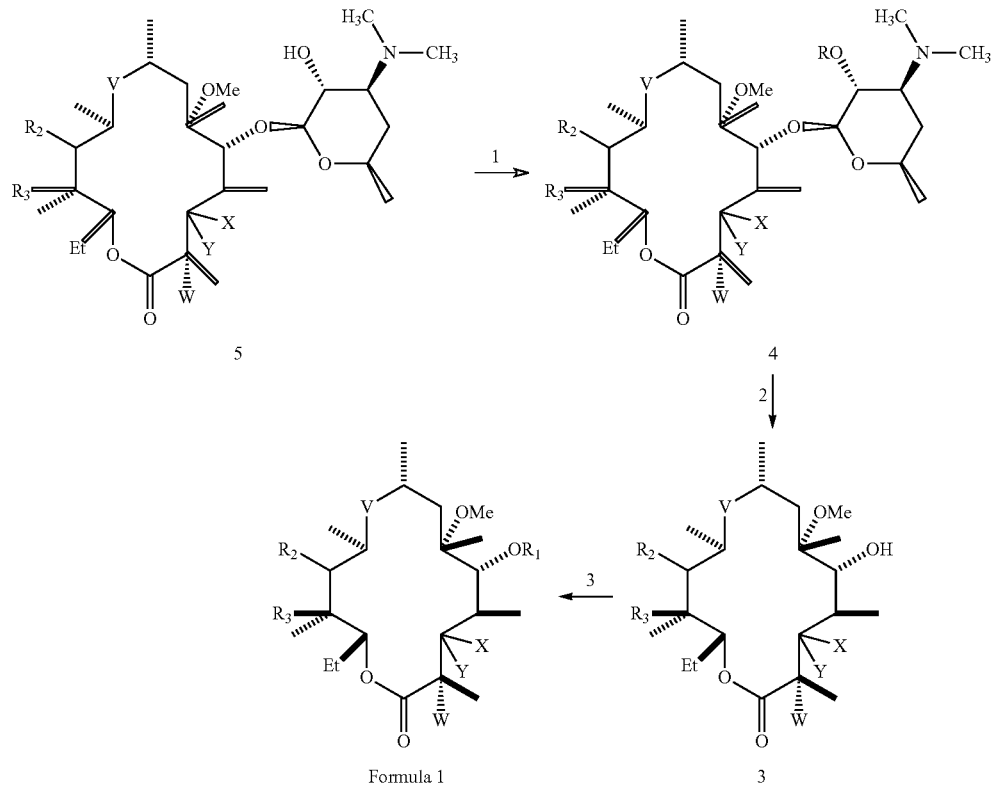

Formula 1

In step 1 of Scheme 1, the desosamine of Formula 5 is protected using methods know to those skilled in the art to provide a compound of Formula 4; R can be ester protecting group but not limited to ester protecting group. The cleavage of the desosamine sugar forms an aglycone compound of Formula 3. In step 2 of Scheme 1, the compound of Formula 3 is functionalized to form a compound of Formula 1. Wherein $R_1$ is selected from cyclic and acyclic alkyl, cyclic and acyclic alkyl-hydroxyamine, aryl, aryl-hydroxyamine, cyclic and acyclic acyl, cyclic and acyclic acyl-hydroxyamine, heteroalkyl, heteroalkyl-hydroxyamine, heteroaryl, heteroaryl-hydroxyamine, acylaryl, acylaryl-hydroxyamine, acylheteroaryl, acylheteroaryl-hydroxyamine, alkylaryl, alkylaryl-hydroxyamine, alkylheteroaryl, alkylheteroaryl-hydroxyamine, sulfonylalkyl, sulfonylalkyl-hydroxyamine, acylalkoxylsulfonylalkyl, acylalkoxylsulfonylalkyl-hydroxyamine;

or $R_1$ can be —C(O)—$NR_4R_5$, where $R_4$ and $R_5$ can be independently or taken together as hydrogen, hydroxy, alkyl, aralkyl, alkylaryl, alkoxy, heteroalkyl, aryl, heteroaryl, dimethylaminoalkyl, acyl, sulfonyl, urea or carbamate and acceptable salts thereof;

or $R_1$ can also be a monosaccharide (including amino sugars and their derivatives, particularly, a mycaminose derivatized at the C-4' position or a 4-deoxy-3-amino-glucose derivatized at the C-6' position), a disaccharide (including a mycaminose derivatized at the C-4' position with another sugar or a 4-deoxy-3-amino-glucose derivatized at the C-6' position with another sugar), a trisaccharide (including aminosugars and halosugars), chloramphenicol, clindamycin or their analogs; provided that $R_1$ can not be desosamine.

Synthesis of the compounds of Formula 1 may comprise other steps in addition to those shown in Scheme 1. For example, groups bonded to $R_2$ may be modified following derivatization of C5 hydroxy group of formula 3.

Compounds of Formula 2 comprise a heteroaromatic ring linked via a spacer to nitrogen at position 11 around a 14-membered macrolide core. The heteroaromatic ring and spacer are abbreviated "A-B-C":

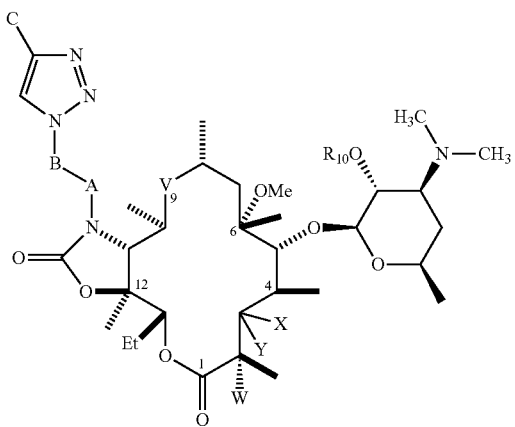

An "A-B-C" moiety may be appended to a macrolide scaffold using a variety of methods. Commercially available macrolides bear a number of reactive functional groups, which may be further functionalized after suitable protection of other possible reactive sites. Macrolides that bear nucleophilic functional groups (for example amines and hydroxyl groups) may be treated with an "E-B-T-C" fragment bearing at least one complimentary electrophilic group, E, that T represent 1,4-substituted 1,2,3-triazole moiety. The terms "nucleophilic", "nucleophile," "electrophilic" and "electrophile" have their usual meanings familiar to synthetic and/or physical organic chemistry.

Preferred electrophiles of the present invention are carbon electrophiles. Examples of preferred carbon electrophiles include but are not limited to carbonyls (especially aldehydes and ketones), oximes, hydrazones, epoxides, aziridines, alkyl-, alkenyl-, and aryl halides, acyls, sulfonates (aryl, alkyl and the like). Other examples of carbon electrophiles include unsaturated carbons electronically conjugated with electron-withdrawing groups, examples being the β-carbon in α,β-unsaturated ketones or carbon atoms in fluorine substituted aryl groups. In general, carbon electrophiles are susceptible to attack by complementary nucleophiles wherein an attacking nucleophile brings an electron pair to the carbon electrophile in order to form a new bond between the nucleophile and the electrophile.

Preferred nucleophiles suitable for coupling to carbon electrophiles include but are not limited to primary and secondary amines, thiols, thiolates, and thioethers, alcohols, alkoxides. These preferred nucleophiles, when used in conjunction with preferred carbon electrophiles, typically generate heteroatom linkages (C—X—C) between a scaffold and a linker group. Nucleophilic attack by the macrolide nucleophile on a suitably substituted heteroaromatic substrate "B-T-C" bearing a functional group "E", which contains an electrophilic carbon or sulfur atom, can thus unite the two through the formation of linker "A" (Scheme 2).

Scheme 2

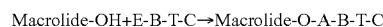

Alternatively, the fragment "A-B-T-C" can be attached to a macrolide scaffold in a stepwise manner such as described below in examples 1-5. Here the heterocyclic ring "T" is a 1,4-substituted 1,2,3-triazole prepared using a Huisgen cyclization, which constitutes the final step of each synthesis. The copper catalyzed Huisgen cyclization has been shown to unite azides and terminal acetylenes regiospecifically to give exclusively 1,4-disubstituted [1,2,3]-triazoles (Tornøe et al., *J. Org. Chem.,* 2002, 67, 3057) and this observation was confirmed using NOE experiments carried out on model compounds. Commercially available macrolides were suitably protected and then modified by the attachment of either an azide or an alkyne functional group through a linker or spacer "A-B". The activated macrolides were then coupled with the fragment "C" which bears the complimentary functional group. The reactions were carried out either solvent-free, in water or in an organic solvent such as acetonitrile or toluene. The reactions were carried out at temperatures ranging from 20 to 80° C. The reaction could be promoted with the use of a catalyst, including but not limited to a transition metal halide ($MX_n$) (Scheme 3).

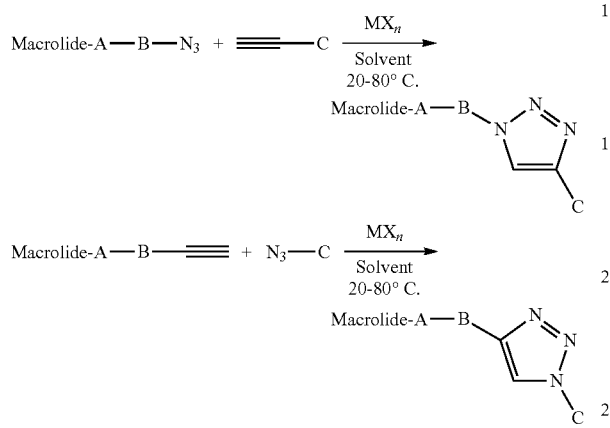

The term "scaffold" refers to a molecule that provides a molecular framework on which to append another chemical moiety or functional group. An antibiotic scaffold is a scaffold having recognized usefulness as an antibiotic. Appending chemical moieties to an antibiotic scaffold may beneficially alter a number of properties of an antibiotic including, but not limited to, absorption, distribution, metabolism, excretion and toxicity, and efficacy.

The term "unsaturated moiety" refers in general to a moiety comprising one or more π-bonds. Examples of such moieties are optionally substituted alkenes, alkynes, and nitriles. Unsaturated moieties undergo pericyclic reactions with complimentary dienes, heterodienes, and 1,3-dipoles resulting in the formation of 5 and 6-membered ring compounds. 1,3-Dipoles and dienes may themselves be part of an open-chain framework, or part of a ring system, with the exception that they may not be frozen into a transoid configuration.

The term "pericyclic reaction" refers to a family of chemical reactions characterized by bonding changes taking place through reorganization of electron pairs within a closed loop of interacting orbitals. Bonding changes in pericyclic reactions are typically, but not necessarily concerted, that is, bonds break and form simultaneously rather than in two or more steps. Preferred types of pericyclic reactions include but are not limited to cycloaddition reactions. A cycloaddition reaction is a reaction in which two or more molecules condense to form a ring by transferring electrons from π-bonds to new σ-bonds. Examples of such reactions are Huisgen cycloadditions, Diels-Alder and hetero Diels-Alder cycloadditions. A preferred type of cycloaddition reaction according to one embodiment of the invention is a Huisgen cyclization. A Huisgen cycloaddition involves the addition of an unsaturated moiety to a 1,3 dipole, as for example shown schematically below:

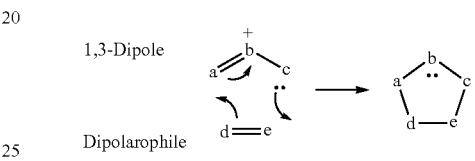

Triazoles result when azides add to triple bonds in a Huisgen cycloaddition. A Huisgen cycloaddition is one example of a group of reactions in which five-membered heterocyclic compounds are prepared by addition of 1,3-dipolar compounds to an unsaturated (usually double or triple) bond, the latter also known as a 1,3-dipolaraphile.

When two molecules react to form a cycloadduct, mixtures may result. Obtaining one or more desired cycloadduct when several are theoretically possible is known as stereocontrol. When an unsymmetrical 1,3-dipole adds to an unsymmetrical dipolarophile, there are two possible products (not counting stereoisomers). Although mixtures are often obtained, one may predominate. This regioselectivity may often be explained via theoretical and or calculational considerations.

The invention will be further illustrated by reference to the following non-limiting Examples.

Example 1

11-N-(4-Azido-butyl)-6-O-methyl-5-OH-3-oxo-erythronolide A, 11,12-carbamate

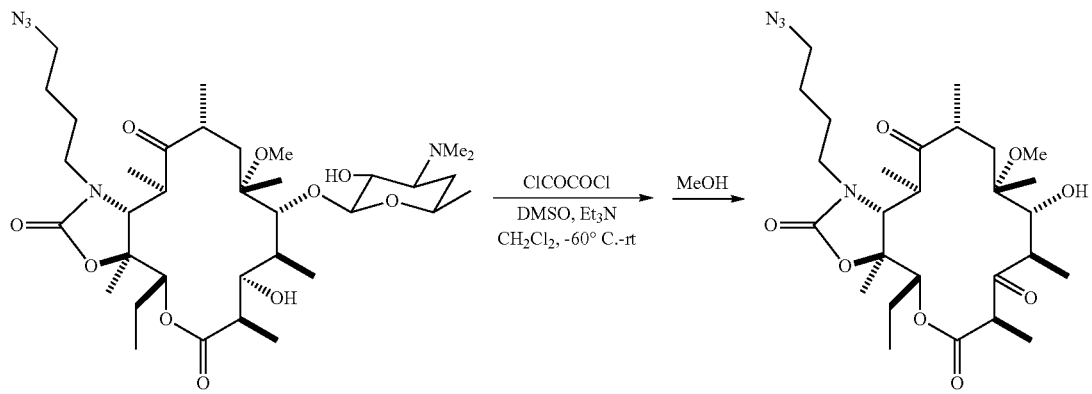

DMSO (0.313 mL, 4.4 mmol) was added dropwise to a solution of oxalyl chloride (2M solution in $CH_2Cl_2$, 1.47 mL, 2.94 mmol) and $CH_2Cl_2$ (10 mL) at −65° C. After 10 min, a solution of 11-N-(4-Azido-butyl)-6-O-methyl-5-desosaminyl-3-hydroxyl-erythronolide A, 11,12-carbamate (0.6 g, 0.84 mmol) and $CH_2Cl_2$ (10 mL) was slowly added and the reaction mixture was gradually allowed to warm to −50° C. After 30 min, $Et_3N$ (1.03 mL, 7.35 mmol) was added and the reaction mixture was slowly allowed to warm to rt. Saturated aqueous $NaHCO_3$ solution (10 mL) was added and the resulting layers were separated. The aqueous layer was extracted with $CH_2Cl_2$ (50 mL) and the combined organic layers were dried with $Na_2SO_4$ and concentrated. The resulting yellow solid was dissolved in MeOH (50 mL) and solution was allowed to stand at 45° C. under nitrogen protection for 24 h. Concentration followed by silica gel chromatography (5:1, Tol:Acetone) afforded 271 mg (57%) of 11-N-(4-azido-butyl)-6-O-methyl-5-OH-3-oxo-erythronolide A, 11,12-carbamate as a white solid. MS: $C_{27}H_{44}N_4O_8$ calculated $M^+$=552.3. Found: $M+H^+$=553.3.

Example 2

11-N-(4-Azido-butyl)-2-Fluoro-6-O-methyl-5-OH-3-oxo-erythronolide A, 11,12-carbamate

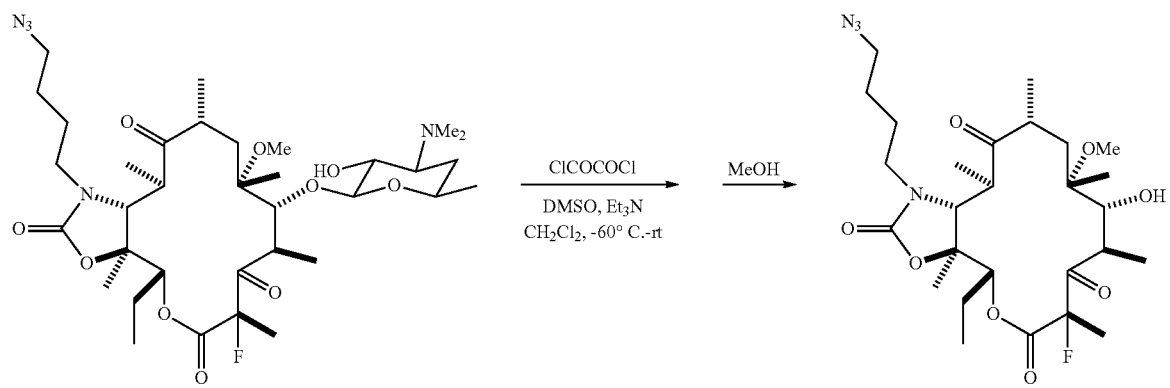

DMSO (0.110 mL, 1.54 mmol) was added dropwise to a solution of oxalyl chloride (2M solution in $CH_2Cl_2$, 0.51 mL, 1.026 mmol) and $CH_2Cl_2$ (5 mL) at −65° C. After 10 min, a solution of 11-N-(4-Azido-butyl)-2-fluoro-6-O-methyl-5-desosaminyl-3-hydroxyl-erythronolide A, 11,12-carbamate (0.37 g, 0.51 mmol) and $CH_2Cl_2$ (3 mL) was slowly added and the reaction mixture was gradually allowed to warm to −50° C. After 30 min, $Et_3N$ (0.36 mL, 2.56 mmol) was added and the reaction mixture was slowly allowed to warm to rt. Saturated aqueous $NaHCO_3$ solution (10 mL) was added and the resulting layers were separated.

The aqueous layer was extracted with $CH_2Cl_2$ (50 mL) and the combined organic layers were dried with $Na_2SO_4$ and concentrated. The resulting yellow solid was dissolved in MeOH (50 mL) and solution was allowed to stand at 45° C. under nitrogen protection for 24 h. Concentration followed by silica gel chromatography (5:1, Tol:Acetone) afforded 157 mg (54%) of 11-N-(4-azido-butyl)-2-fluoro-6-O-methyl-5-OH-3-oxo-erythronolide A, 11,12-carbamate as a white solid. MS: $C_{27}H_{43}N_4FO_8$ calculated $M^+$=570.3. Found: $M+Na^+$=593.3.

Example 3

11-N-(4-Azido-butyl)-6-O-methyl-5-(2,6-dibenzoyl-3N-Fmoc-4-deoxy-glucopyranosyl)-3-oxo-erythronolide A, 11,12-carbamate

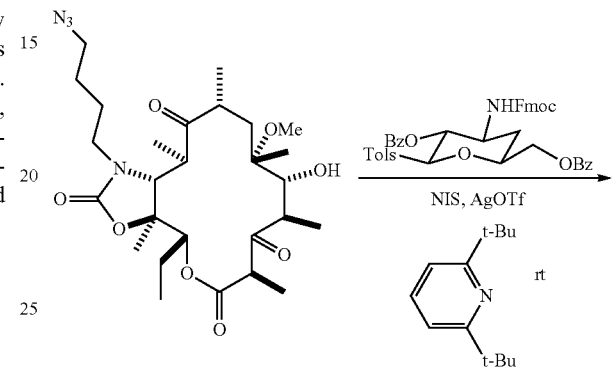

-continued

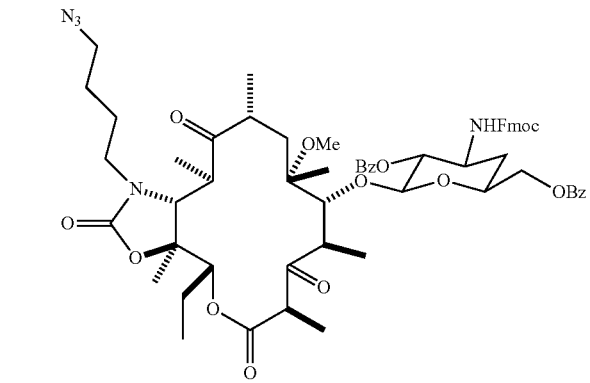

N-Iodosuccinimide (0.630 g, 2.8 mmol) was added to a mixture of 11-N-(4-Azido-butyl)-6-O-methyl-5-OH-3-oxo-erythronolide A, 11,12-carbamate (1 g, 1.8 mmol), 2,6-dibenzoyl-3-N-Fmoc-4-deoxy-1-thio-D-glucopyranoside (1.64 mg, 2.35 mmol), molecular sieves (0.5 g), and CH$_2$Cl$_2$ (24 mL) at −78° C. After 10 min, AgOTf (0.84 g, 3.24 mmol) and 2,6-Di-tert-butyl-pyridine (0.68 g, 3.56 mmol) were added and the mixture was gradually allowed to warm to rt. After 6 h, a 1:1 mixture of saturated aqueous NaHCO$_3$ and Na$_2$SO$_3$ (100 mL) was added and the mixture was diluted with CH$_2$Cl$_2$ (250 mL) and the resulting layers were separated. The organic layer was dried with Na$_2$SO$_4$ and concentrated. Purification by silica gel chromatography (10:1, Toluene:Acetone) afforded 1.35 g of compound 3 as a white film. MS: C$_{62}$H$_{73}$N$_5$O$_{15}$ calculated M$^+$=1127.51. Found: M+Na$^+$=1150.5.

Example 4

11-N-(4-Azido-butyl)-6-O-methyl-5-(3-dimethylamine-4-deoxy-6-benzoyl-glucopyranosyl)-2-fluoro-3-oxo-erythronolide A, 11,12-carbamate

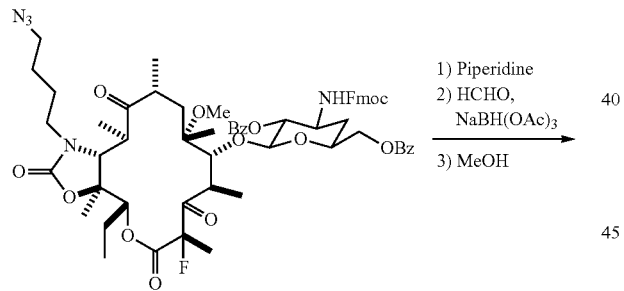

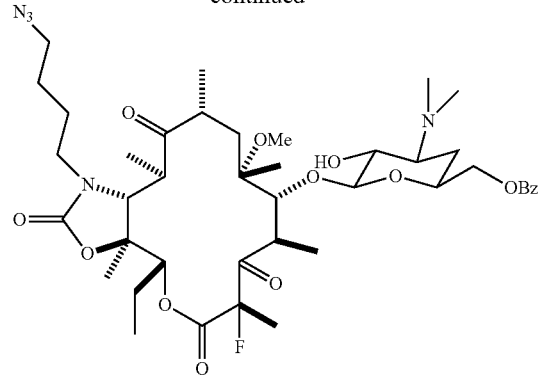

Piperidine (0.2 mL, 10% in DMF) was added to 11-N-(4-Azido-butyl)-6-O-methyl-5-(2,6-dibenzoyl-3N-Fmoc-4-deoxy-glucopyranosyl)-2-fluoro-3-oxo-erythronolide A, 11,12-carbamate (27 mg, 0.024 mmol), at room temperature. After 10 min, the reaction mixture were concentrated in vacuum and re-constituted with THF (1 mL). To the above solution, formaldehyde (37% aqueous solution, 0.05 mL, 0.67 mmol) and Sodium triacetoxyborohydride (50 mg, 0.22 mmol) were added at room temperature. After 2 hour of stirring, the reaction mixture was diluted with 1:1 ratio of saturated aqueous ammonium chloride and dichloromethane (20 mL). The organic layer was separated and dried with Na$_2$SO$_4$ and concentrated to give a while film. The intermediate was dissolved in methanol and stirred for 18 hour at rt. Concentration of the above reaction mixture follows by purification with silica gel chromatography (10:1, Toluene:Acetone) afforded 10 mg of title compound as a white film. MS: C$_{42}$H$_{62}$FN$_5$O$_{12}$, calculated M$^+$=847.44. Found: M+H$^+$=848.5

Example 5

OP-1356: 11-N-{4-[4-(6-Amino-pyridin-2-yl)-[1,2,3]triazol-1-yl]-butyl}-5-(3-dimethylamine-4-deoxy-6-O-acetyl-glucopyranosyl)-3-oxo-2-fluoro-erythronolide A,-11,12-cyclic carbamate

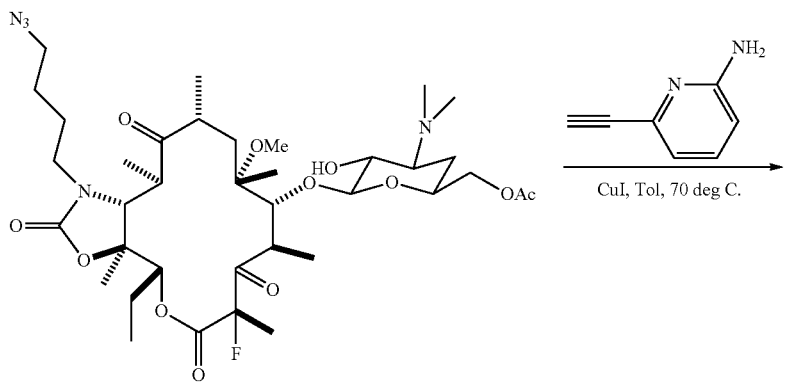

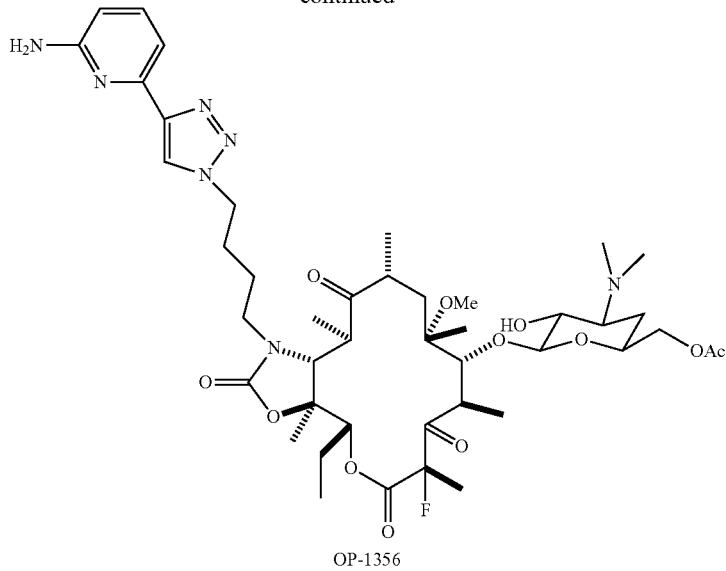

OP-1356

A mixture of 11-N-(4-Azido-butyl)-6-O-methyl-5-(3-dimethylamine-4-deoxy-6-O-acetyl-glucopyranosyl)-2-fluoro-3-oxo-erythronolide A, 11,12-carbamate (15 mg, 0.019 mmol), 6-Ethynyl-pyridin-2-ylamine (4.7 mg, 0.4 mmol), CuI (1 mg, 0.005 mmol), and toluene (0.2 mL) was heated to 70° C. After 16 h, the mixture was concentrated and directly subjected to silica gel chromatography (9:1, Chloroform:Methanol plus 1% ammonium hydroxide) to give 14 mg of the desired compound OP-1356. MS: $C_{44}H_{66}FN_7O_{12}$ calculated $M^+$=903.5. Found: $M+H^+$=904.5.

Example 6

11-N-(4-Azido-butyl)-6-O-methyl-5-(2-acetyl-desosamynyl)-3-oxo-2-fluoro-erythronolide A, 11,12-carbamate

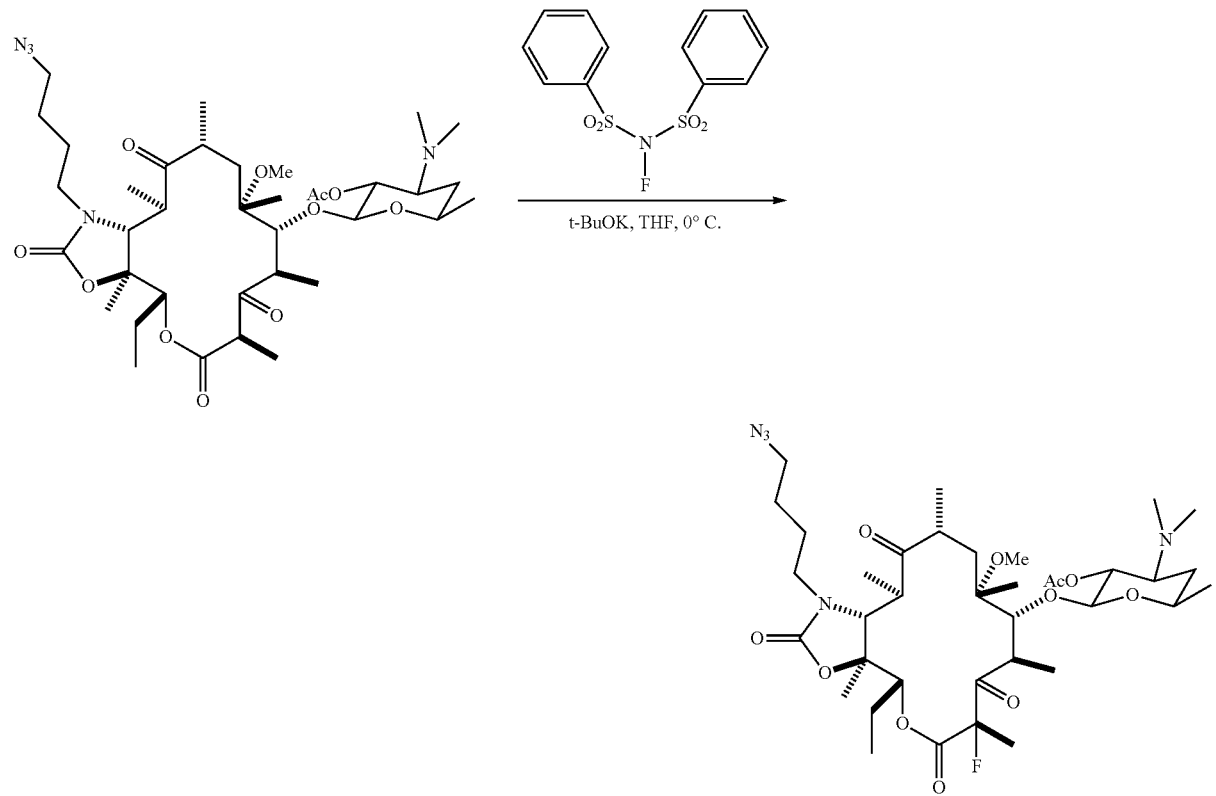

To a solution of 11-N-(4-Azido-butyl)-6-O-methyl-5-(2-acetyl-desosaminyl)-3-oxo-erythronolide A, 11,12-carbamate (500 mg, 0.66 mmol) in THF (8 mL), t-BuOK (0.73 mL, 1.0 M, 0.73 mmol) followed by N-Fluorobenzene-sulfonimide (211 mg, 0.66 mmol) were added dropwise at 0° C. After 40 min., the mixture was quenched with water (2 mL) follow by dilution of dichloromethane (200 mL). The organic layer were separated and washed with water (20 mL×2). Upon concentration of the organic layer gave 482 mg of product. MS: $C_{37}H_{60}FN_5O_{11}$ calculated $M^+$=769.43. Found: $M+H^+$=770.5.

Example 7

OP-1068: 11-N-(3-amino-phenyl-1-ylmethyl-[1,2,3]triazol-1-yl]-butyl}-5-desosaminyl-3-oxo-2-fluoro-erythronolide A,-11,12-cyclic carbamate

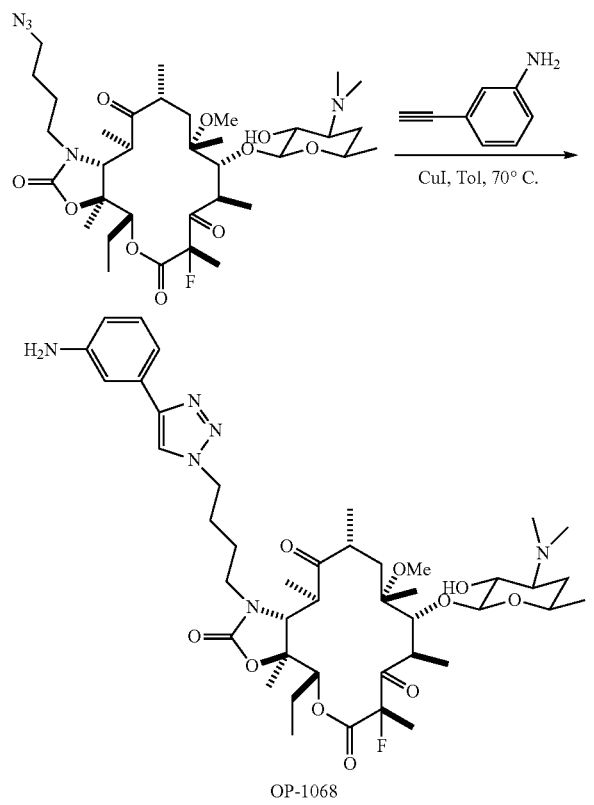

OP-1068

A mixture of 11-N-(4-Azido-butyl)-6-O-methyl-5-desosamynyl-3-oxo-2-fluoro-erythronolide A, 11,12-carbamate (17 mg, 0.023 mmol), 3-Ethynyl-phenylamine (5.4 mg, 0.046 mmol), CuI (1 mg, 0.005 mmol), and toluene (0.2 mL) was heated to 70° C. After 16 h, the mixture was concentrated and directly subjected to silica gel chromatography (9:1, Chloroform:Methanol plus 1% ammonium hydroxide) to give 17 mg of the desired compound, OP1068. MS $C_{43}H_{65}FN_6O_{10}$ calculated $M^+$=844.47. Found: $M+H^+$=845.5

Example 8

OP-1357: 11-N-{4-[4-(6-Amino-pyridin-2-yl)-[1,2,3]triazol-1-yl]-butyl}-5-desosaminyl-3-oxo-2-fluoro-erythronolide A,-11,12-cyclic carbamate

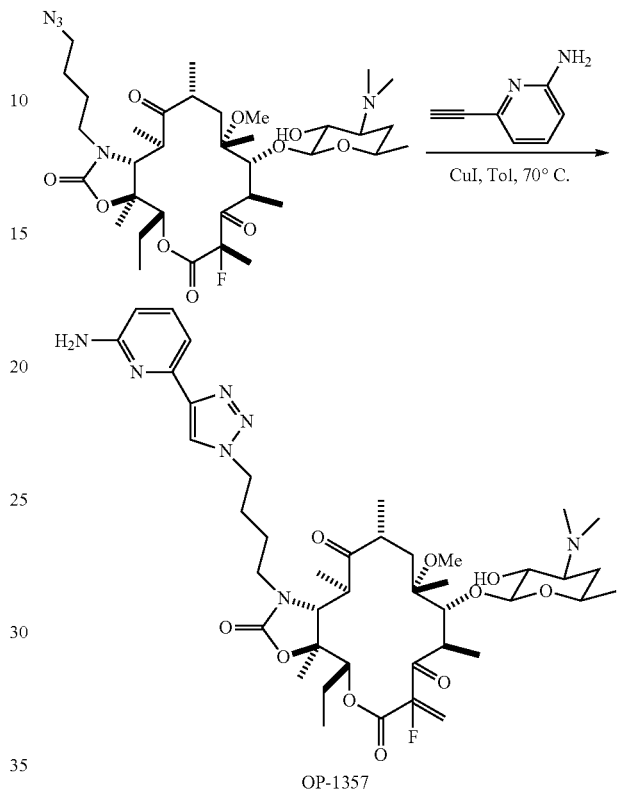

OP-1357

A mixture of 11-N-(4-Azido-butyl)-6-O-methyl-5-desosamynyl-3-oxo-2-fluoro-erythronolide A, 11,12-carbamate (15 mg, 0.02 mmol), 6-Ethynyl-pyridin-2-ylamine (4.7 mg, 0.4 mmol), CuI (1 mg, 0.005 mmol), and toluene (0.2 mL) was heated to 70° C. After 16 h, the mixture was concentrated and directly subjected to silica gel chromatography (9:1, Chloroform:Methanol plus 1% ammonium hydroxide) to give 14 mg of the desired compound OP1357. MS: $C_{42}H_{64}FN_7O_{10}$ calculated $M^+$=845.5. Found: $M+H^+$=846.5.

Example 9

11-N-(4-Azido-butyl)-6-O-methyl-5-(2,4-dibenzoyl-3N-Fmoc-mycaminosyl)-3-oxo-erythronolide A, 11,12-carbamate

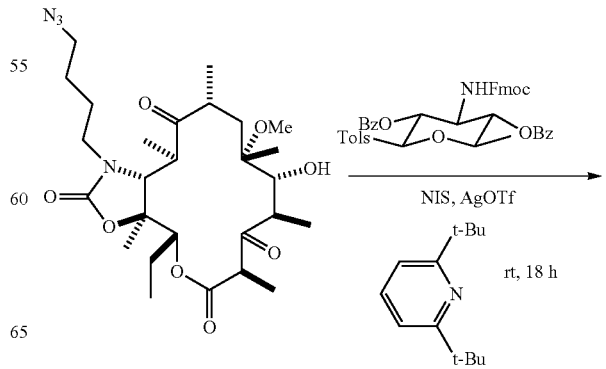

-continued

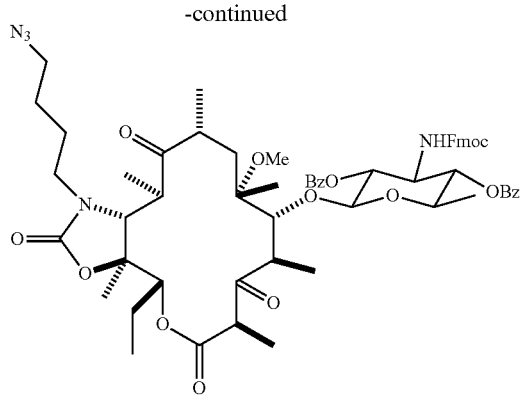

N-Iodosuccinimide (162 mg, 0.72 mmol) was added to a mixture of 11-N-(4-Azido-butyl)-6-O-methyl-5-OH-3-oxo-erythronolide A, 11,12-carbamate (200 mg, 0.36 mmol), 2,6-dibenzoyl-3-N-Fmoc-1-thiomycaminoside (378 mg, 0.54 mmol), molecular sieves (0.2 g), and $CH_2Cl_2$ (2.5 mL) at −78° C. After 10 min, AgOTf (224 mg, 0.86 mmol) and 2,6-Di-tert-butyl-pyridine (0.21 mL, 0.95 mmol) were added and the mixture was gradually allowed to warm to rt. After 18 h, a 1:1 mixture of saturated aqueous $NaHCO_3$ and $Na_2SO_3$ (100 mL) was added and the mixture was diluted with $CH_2Cl_2$ (250 mL) and the resulting layers were separated. The organic layer was dried with $Na_2SO_4$ and concentrated. Purification by silica gel chromatography (10:1, Toluene:Acetone) afforded 293 mg of title compound as a white film. MS: $C_{62}H_{73}N_5O_{15}$ calculated $M^+=1127.51$. Found: $M+Na^+=1150.5$.

Example 10

11-N-(4-Azido-butyl)-6-O-methyl-5-mycaminosyl-3-oxo-erythronolide A, 11,12-carbamate

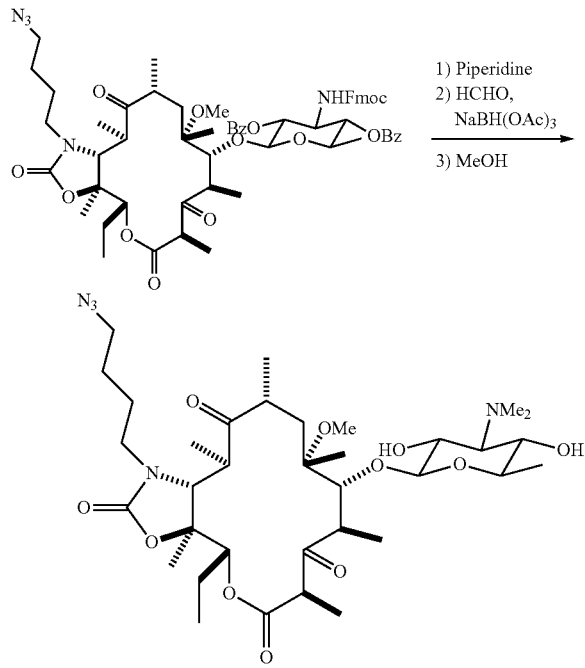

Piperidine (0.2 mL, 10% in DMF) was added to 11-N-(4-Azido-butyl)-6-O-methyl-5-(2,4-dibenzoyl-3N-Fmoc-mycaminosyl)-3-oxo-erythronolide A, 11,12-carbamate (30 mg, 0.026 mmol), at room temperature. After 10 min, the reaction mixture were concentrated in vacuum and re-constituted with THF (1 mL). To the above solution, formaldehyde (37% aqueous solution, 0.05 mL, 0.67 mmol) and Sodium triacetoxyborohydride (50 mg, 0.22 mmol) were added at room temperature. After 2 hour of stirring, the reaction mixture was diluted with 1:1 ratio of saturated aqueous ammonium chloride and dichloromethane (20 mL). The organic layer was separated and dried with $Na_2SO_4$ and concentrated to give a while film. The intermediate was dissolved in methanol and stirred for 18 hour at rt. Concentration of the above reaction mixture follows by purification with silica gel chromatography (10:1, Toluene:Acetone) afforded 9 mg of title compound as a white film. MS: $C_{35}H_{59}N_5O_{11}$, calculated $M^+=725.4$. Found: $M+H^+=726.5$ Example 11

OP-1007: 11-N-[4-(4-Benzotriazol-1-ylmethyl-[1,2,3]triazol-1-yl)-butyl]-6-O-methyl-5-O-dasosaminyl-3-oxo-erythronolide A, 11,12-carbamate

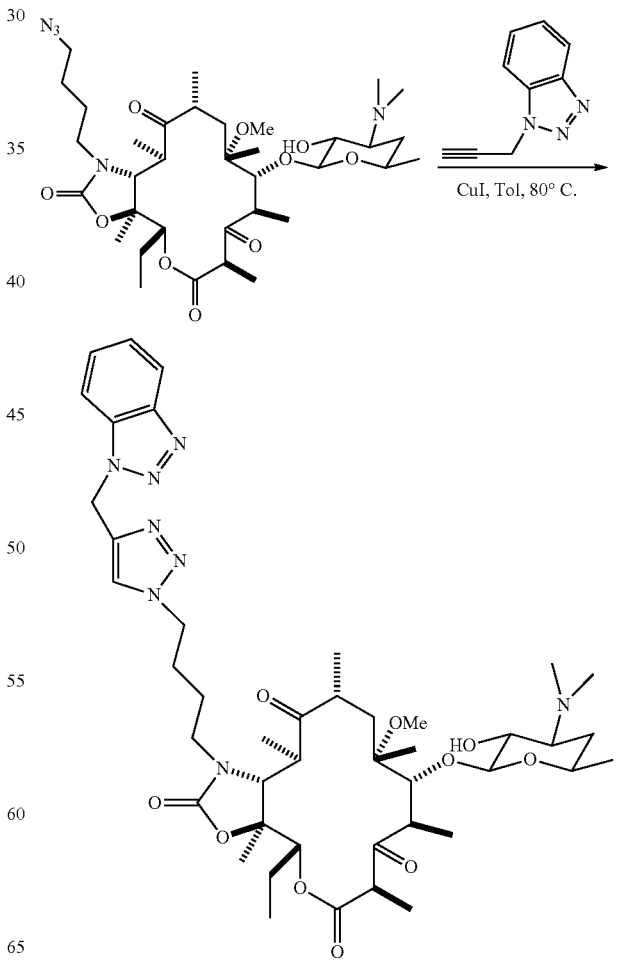

A mixture of 11-N-(4-Azido-butyl)-6-O-methyl-5-O-desosaminyl-3-oxo-erythronolide A, 11,12-carbamate (3 mg, 0.0039 mmol), 1-Prop-2-ynyl-1H-benzotriazole (3 mg, 0.4 mmol), CuI (1 mg, 0.005 mmol), and toluene (0.2 mL) was heated to 80° C. After 16 h, the mixture was concentrated and directly subjected to silica gel chromatography (9:1, Chloroform:Methanol plus 1% ammonium hydroxide) to give 3 mg of the desired compound OP-1007. MS: $C_{44}H_{66}N_8O_{10}$ calculated $M^+$=866.5. Found: $M+H^+$ 867.5.

Example 12

OP-1071: 11-N-[4-(4-Benzotriazol-1-ylmethyl-[1,2,3]triazol-1-yl)-butyl]-6-O-methyl-5-mycaminosyl-3-oxo-erythronolide A, 11,12-carbamate

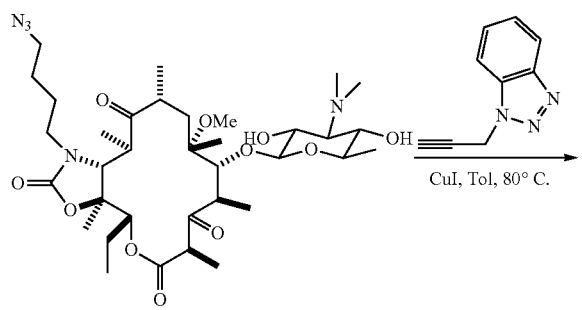

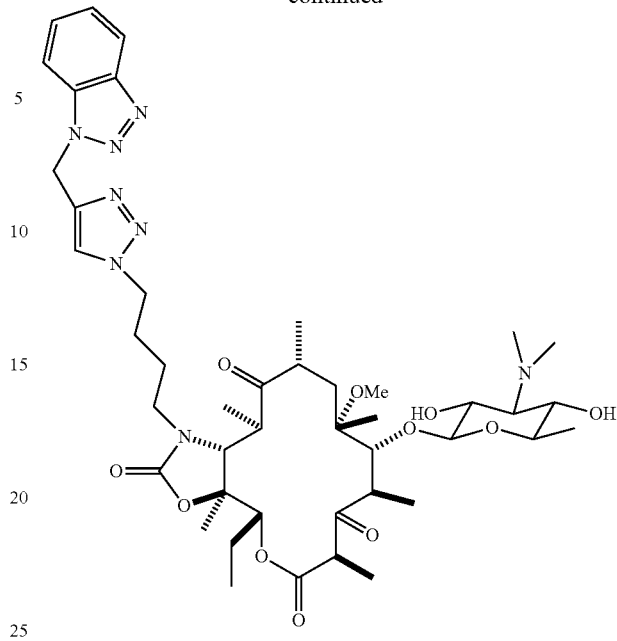

A mixture of 11-N-(4-Azido-butyl)-6-O-methyl-5-mycaminosyl-3-oxo-erythronolide A, 11,12-carbamate (3 mg, 0.004 mmol), 1-Prop-2-ynyl-1H-benzotriazole (3 mg, 0.4 mmol), CuI (1 mg, 0.005 mmol), and toluene (0.2 mL) was heated to 80° C. After 16 h, the mixture was concentrated and directly subjected to silica gel chromatography (9:1, Chloroform:Methanol plus 1% ammonium hydroxide) to give 3 mg of the desired compound OP-1071. MS: $C_{44}H_{66}N_8O_{11}$ calculated $M^+$=882.5. Found: $M+H^+$=883.5.

Example 13

11-N-[4-(4-Pyridin-3-yl-imidazol-1-yl-butyl]-6-O-methyl-5-OH-3-oxo-erythronolide A, 11,12-carbamate

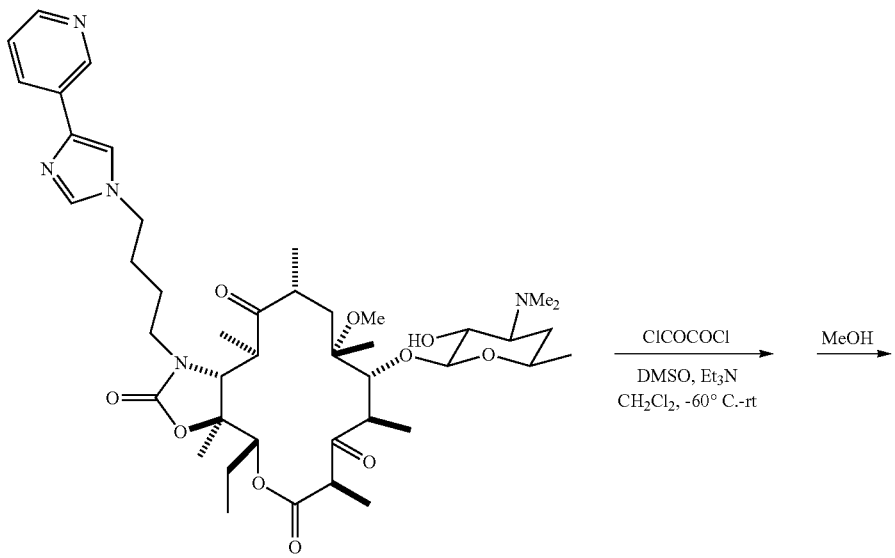

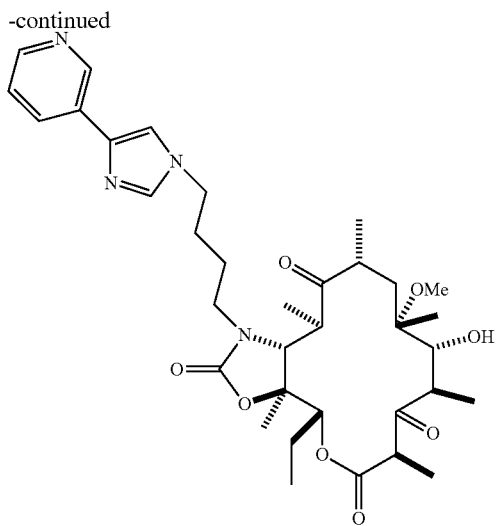

DMSO (0.22 mL, 3.0 mmol) was added dropwise to a solution of oxalyl chloride (2M solution in $CH_2Cl_2$, 1.4 mL, 2.7 mmol) and $CH_2Cl_2$ (6 mL) at −70° C. After 10 min, a solution of Telithromycin (1.0 g, 1.2 mmol) and $CH_2Cl_2$ (6 mL) was slowly added and the reaction mixture was gradually allowed to warm to −50° C. After 30 min, $Et_3N$ (0.9 mL, 6 mmol) was added and the reaction mixture was slowly allowed to warm to rt. Saturated aqueous $NaHCO_3$ solution (10 mL) was added and the resulting layers were separated. The aqueous layer was extracted with $CH_2Cl_2$ (50 mL) and the combined organic layers were dried with $Na_2SO_4$ and concentrated. The resulting yellow solid was dissolved in MeOH (50 mL) and solution was allowed to stand at rt overnight. Concentration followed by silica gel chromatography (5:5:0.5:0.1, Tol:Acetone:MeOH:$Et_3N$) afforded 350 mg (44%) of 11-[4-(4-Pyridin-3-yl-imidazol-1-yl-butyl]-6-O-methyl-5-OH-3-oxo-erythronolide A, 11,12-carbamate as a white solid. MS: $C_{35}H_{50}N_4O_8$ calculated $M^+=654.8$. Found: $M+H^+=655.4$.

Example 14

OP-1086:11-N-[4-(4-Pyridin-3-yl-imidazol-1-yl-butyl]-6-O-methyl-5-O—(N-t-butylcarbonate-N,O-isopropylidene isoserinate)-3-oxo-erythronolide A, 11,12-carbamate

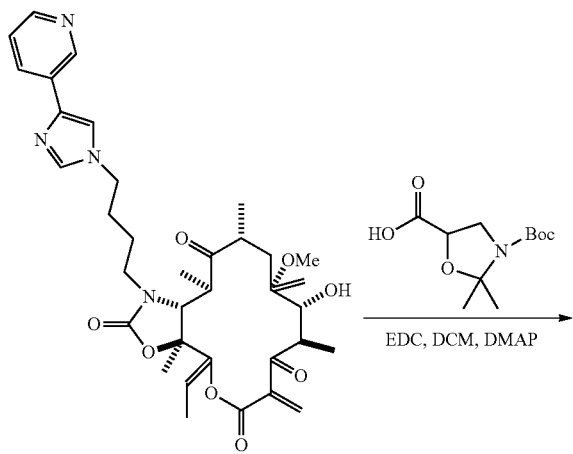

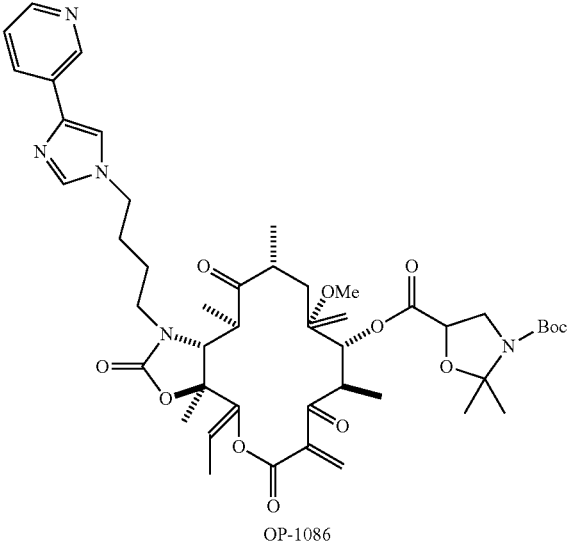

OP-1086

11-N-[4-(4-Pyridin-3-yl-imidazol-1-yl-butyl]-6-O-methyl-5-OH-3-erythronolide A, 11,12-carbamate (56.7 mg, 86.6 mmol) was taken up in 1 mL of dichloromethane. To the solution was added 60 mg of N-t-butylcarbonate-N,O-isopropylidene isoserine triethylamine salt (173 mmol) followed by 33.1 mg of 1-[3-(dimethylamino)propyl]-3-ethylcarbodiimide hydrochloride (173 mmol) and 42.2 mg of 4-(dimethylamino)pyridine (346 mmol). The reaction was allowed to stir overnight and was incomplete mass spectroscopy. An additionally 8 equivalents of N-t-butylcarbonate-N,O-isopropylidene isoserine triethylamine salt and 1-[3-(dimethylamino)propyl]-3-ethylcarbodiimide hydrochloride were added and the reaction was complete within 1 hour. The solution was quenched with saturated sodium bicarbonate solution and extracted with three 10 mL-portions of dichloromethane. The organic layers were combined and dried ($MgSO_4$). The solution was concentrated under diminished pressure and purified by flash column chromatography on silica (10 g). The column was eluted with 97.5:2.5 (dichloromethane-methanol) to afford the compound as a colorless foam and a 1:1 mixture of diastereomers: yield 45 mg (59%); silica gel TLC $R_f$ 0.78

(9:1:0.1 chloroform-methanol-ammonium hydroxide); $^1$H NMR (400 MHz, CDCl$_3$) δ 0.81-1.99 (m, 47H), 2.55-3.24 (m, 5H), 3.39-4.08 (m, 7H), 4.60 (m, 1H) 4.92 (m, ½H), 5.03 (m, ½H), 5.15 (m, ½H), 5.74 (½H, dd, J=10, 4.5 Hz), 7.30 (m, 1H), 7.34 (s, ½H), 7.39 (s, ½H), 7.55 (s, ½H), 7.60 (s, ½H), 8.45 (m, 1H), 8.10 (s, 1H), 8.96 (s, 1H); $^{13}$C NMR (100 MHz, CDCl$_3$) δ 10.51, 10.69, 13.81, 13.85, 14.20, 14.79, 15.89, 16.58, 18.35, 19.12, 19.40, 22.17, 24.22, 28.35, 28.40, 28.57, 28.76, 38.51, 38.82, 39.11, 39.47, 42.43, 42.51, 44.57, 45.43, 46.80, 46.87, 48.02, 50.19, 50.62, 51.45, 58.69, 60.08, 58.69, 60.08, 75.78, 77.36, 77.58, 82.06, 82.18, 115.56, 123.54, 131.91, 131.99, 137.55, 138.78, 143.47, 145.39, 147.58, 157.20, 169.03, 169.42, 200.90, 215.45; MS: C$_{46}$H$_{67}$N$_5$O$_{12}$ calculated M$^+$=881.5. Found: M+H$^+$=882.4.

Example 15

11-N-[4-(4-Pyridin-3-yl-imidazol-1-yl-butyl]-6-O-methyl-5-O—N-dimethylisoserinate)-3-oxo-erythronolide A, 11,12-carbamate Part I, 11-N-[4-(4-Pyridin-3-yl-imidazol-1-yl-butyl]-6-O-methyl-5-O—(N-t-butyl-carbonate-N,O-isopropylidene isoserinate)-3-erythronolide A, 11,12-carbamate (25.0 mg, 28.3 mmol) was taken up in 200 mL of ice cold 65% aqueous trifluoroacetic acid. The solution was stirred 1 hour at 0° C. and concentrated to dryness; MS: C$_{43}$H$_{63}$N$_5$O$_{12}$ calculated M$^+$=841.5. Found: M+H$^+$=842.4.

Part II, the vacuum dried crude from part I, in the same flask was taken up in 200 mL of cold 1:1 dimethylsulfide-trifluoroacetic acid. The solution was stirred at stirred 1 hour at 0° C. and concentrated to dryness; MS: C$_{38}$H$_{55}$N$_5$O$_{10}$ calculated M$^+$=741.4. Found: M+H$^+$=742.4.

Part III, 17 mg of 11-N-[4-(4-Pyridin-3-yl-imidazol-1-yl-butyl]-6-O-methyl-5-O-isoserinate-3-erythronolide A, 11,12-carbamate (19.8 mmol) from part II, was taken up in 300 mL of tetrahydrofuran. To the solution was added 15.4 mL of 37% aqueous formaldehyde (198 mmol) and 12.6 mg

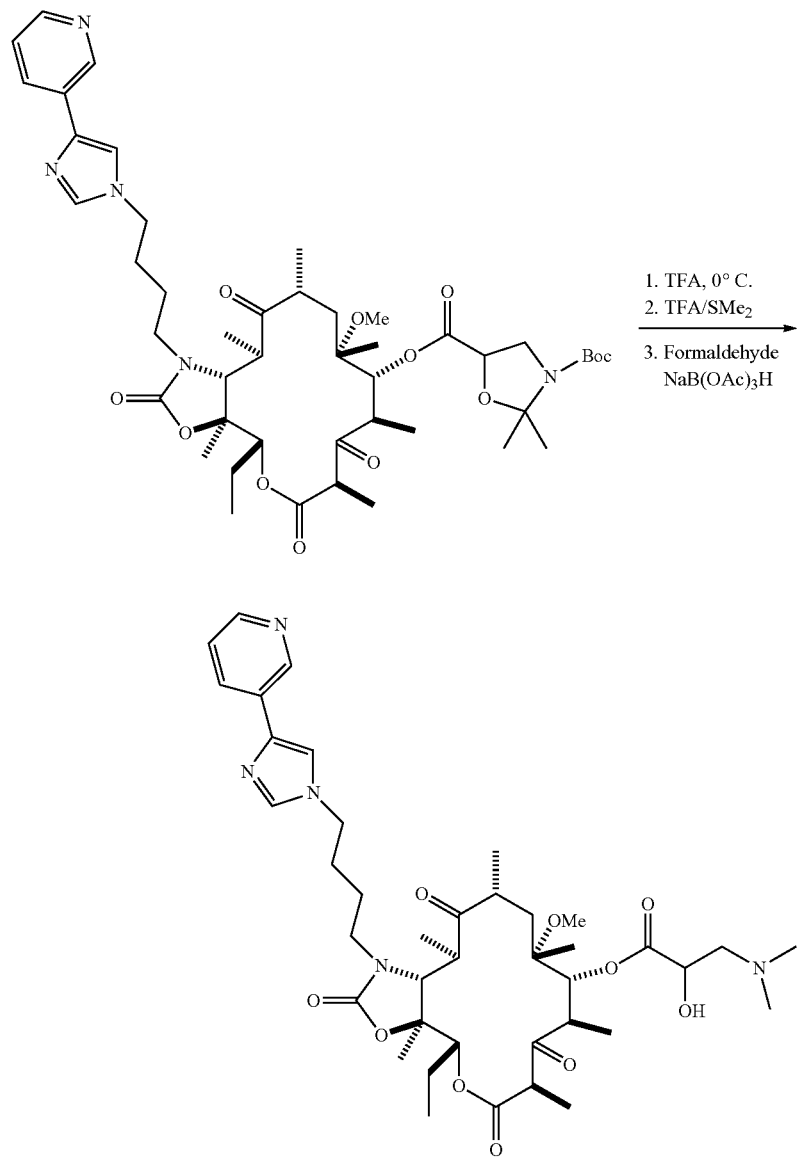

sodium triacetoxyborohydride (59.6 mmol). The solution was allowed to stir 1 hour and was concentrated to dryness. The residue was purified by flash column chromatography on silica (4 g). The column was eluted with 95:5:0.1 (dichloromethane-methanol-ammonium hydroxide) to afford the compound as a colorless foam and a 1:1 mixture of diastereomers: yield 7.5 mg (49%); silica gel TLC $R_f$ 0.52 (4:1 hexanes-ethyl acetate); $^1$H NMR (400 MHz, CDCl$_3$) δ 0.82-0.88 (m, 4H), 1.01 (m, 4H), 1.22 (m, 10H), 1.40 (m, 3H), 1.49 (s, 3H), 1.62-1.68 (m, 4H), 1.88-1.99 (m, 4H), 2.57-2.65 (m, 4H), 2.91 (m, 3H), 2.93 (m, 3H), 3.36 (m, 2H), 3.50 (m, 1H), 3.65-3.82 (m, 4H), 4.03 (t, 2H, J=7.0 Hz), 4.68 (m, 1H), 4.90 (d, 1H, J=10.5 Hz), 5.68 (d, 1H, J=10 Hz), 7.27 (m, 1H), 7.39 (s, 1H), 7.61 (s, 1H), 8.18 (m, 1H), 8.49 (bs, 1H), 8.99 (bs, 1H); MS: $C_{40}H_{59}N_5O_{10}$ calculated M$^+$=769.4. Found: M+H$^+$=770.4.

Example 16

11-N-[4-(4-Pyridin-3-yl-imidazol-1-yl-butyl]-6-O-methyl-5-O-allyl-3-oxo-erythronolide A, 11,12-carbamate

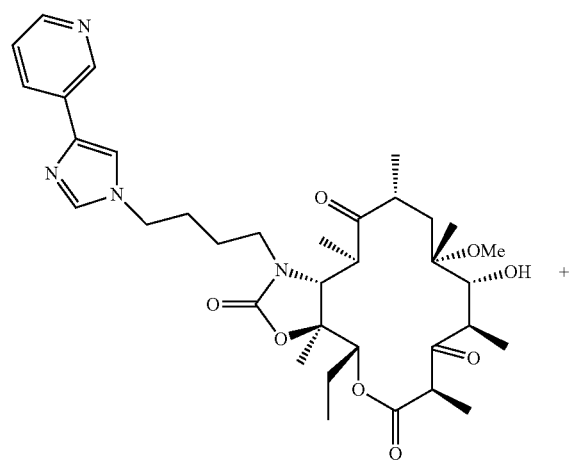

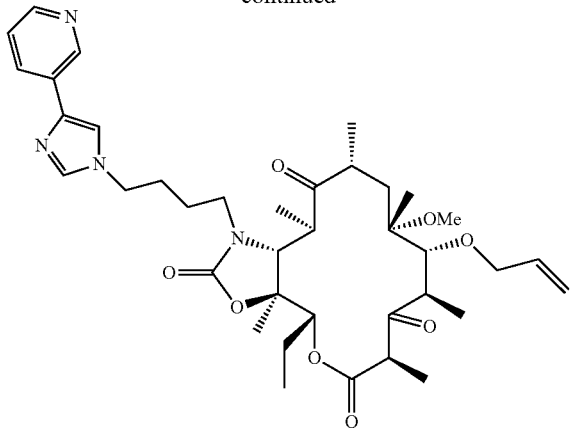

11-N-[4-(4-Pyridin-3-yl-imidazol-1-yl-butyl]-6-O-methyl-5-OH-3-erythronolide A, 11,12-carbamate (1 eq.), allyl t-butyl carbonate (1.5 eq.), palladium acetate (0.005 eq.), and triphenylphosphine (0.043 eq.) were taken up in dry THF. The reaction mixture was purged with N$_2$ before the reaction mixture was heated to reflux. The reaction was allowed to reflux until complete by TLC (95:0.5:0.05 of CHCl$_3$:MeOH:NH$_4$OH), approximately 24 hours. The mixture was concentrated to dryness and purified by column chromatography (15% 9:1:0.1 of CHCl$_3$:MeOH:NH$_4$OH, 85% CHCl$_3$). MS: $C_{35}H_{54}N_4O_8$ calculated M$^+$=694.4. Found: M+H$^+$=695.4.

Example 17

Antibacterial activity of the novel Formula 1 and Formula 2 compounds and their pharmaceutically acceptable addition salts with organic and inorganic acids was determined against a series of microorganisms from the American Type Culture Collection (ATCC) and clinical *Streptococcus* sp isolates. The ATCC strains included: *Staphylococcus aureus*, *Enterococcus faecium*, *Klebsiella pneumoniae*, *Escherichia coli*, *Salmonella typhimurium*, *Streptococcus pneumoniae*, *Streptococcus pyogenes*, and *Haemophilus influenzae*. The clinical strains included macrolide resistant *Streptococcus* sp. with either Erm or MefA resistance mechanisms. The clinical isolates were identified using the API biochemical identification system (BioMerieux).

Antimicrobial susceptibility testing was performed according to recommendations by the National Committee for Clinical Laboratory Standards (NCCLS M100-S12, M7-A5). Briefly, two fold dilutions of compounds were made in microtiter plates. Each well of the microtiter plate was inoculated with test microorganisms at a final density 5×10$^5$ colony forming units (cfu)/mL. The microtiter plates were incubated at 35° C. under aerobic conditions, except for *H. influenzae* and *S. pyogenes* which were incubated at 5% CO$_2$. The minimal inhibitory concentration (MIC) was defined as the lowest concentration of compound that inhibited growth. The results of represented examples of this invention on standard test microorganisms and clinical isolates in comparison with azithromycin and telithromycin are shown in Table 1 and Table 2.

TABLE 1

Antibacterial in vitro activity of OP1007 (Example 11), OP1071 (Example 12) and OP1086 (Example 14) in comparison to Azithromycin and Telithromycin (nd = not determined).

| ID OP- | S. aureus ATCC 29213 (MSSA) MLS-S | E. faecium ATCC 19434 | K. Pneumonia 13883 | E. Coli ATCC 25922 | S. Typhimurium ATCC 14028 | S. pneumoniae ATCC 49619 | S. pyogenes ATCC 19615 | S. pneumoniae 163(MefA) | S. pneumoniae 303(ErmB) | S. areus MRSA 33591 | H. influenzae ATCC 49247 |
|---|---|---|---|---|---|---|---|---|---|---|---|
| | | | | | MIC (mcg/mL) | | | | | | |
| 1007 | <=0.125 | <=0.125 | 32 | 64 | 8 | <=0.125 | <=0.125 | <=0.125 | >64 | >64 | 0.5 |
| 1071 | 0.25 | <=0.125 | >64 | >64 | >64 | <=0.125 | <=0.125 | 0.5 | >64 | >64 | 2 |
| 1086 | 4 | 4 | >64 | >64 | >64 | Nd | 32 | <=0.125 | 0.25 | >64 | >64 |
| Azithromycin | 1 | 4 | 8 | 8 | 4 | <=0.125 | 1 | <=0.125 | 0.5 | >64 | 2 |
| Telithromycin | <=0.125 | <=0.125 | 16 | 16 | 4 | <=0.125 | <=0.125 | <=0.125 | <=0.125 | >64 | 2 |

It is noteworthy that compounds of the present invention show significant improvement in inhibitory activity against telithromycin resistant isolates pathogens, *Streptococcus pyogenes* while they still maintains their similar activity against other pathogens (See Table 2).

TABLE 2

Antibacterial in vitro activity of novel ketolides in comparison to Telithromycin (nd = not determined).

| ID OP- | S. pneumoniae ATCC 49619 | S. pneumoniae ErmB 303 | S. pneumoniae 163(MefA) | S. pneumoniae 3773(ErmB) | S. pneumoniae 5032 | S. pyogenes 1721 | S. pyogenes 1850 | S. pyogenes 3029 | S. pyogenes 3262 | H. influenzae ATCC 49247 |
|---|---|---|---|---|---|---|---|---|---|---|
| | | | | MIC (mcg/mL) | | | | | | |
| 1068 | <=0.125 | <=0.125 | <=0.125 | 0.5, 1 | 0.5 | 0.5 | <=0.125 | <=0.125 | 0.5 | 2, 4 |
| 1274 | <=0.125 | <=0.125 | <=0.125 | 4 | 0.25 | 16 | 0.25 | <=0.125 | 0.5 | 8 |
| 1313 | <=0.125 | <=0.125 | <=0.125 | 1 | 0.5 | 2 | 0.25 | 0.25 | 2 | 2 |
| 1318 | <=0.125 | <=0.125 | <=0.125 | 2 | 2 | 1 | 0.25 | nd | 1 | 8 |
| 1356 | <=0.125 | <=0.125 | <=0.125 | 0.5 | 1 | 4 | 0.25 | 1 | 4 | 1 |
| 1357 | <=0.125 | <=0.125 | <=0.125 | 1 | 1 | 2 | 0.25 | 1 | 1 | 4 |
| Teli | <=0.125 | <=0.125 | <=0.125 | 1 | 1 | 64 | 8 | 16 | 32 | 4 |

It is to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

We claim:

1. A compound of Formula 1 or Formula 2

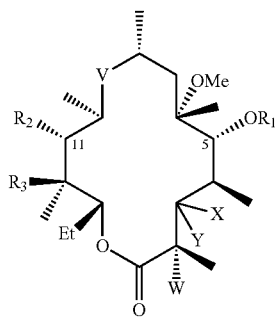

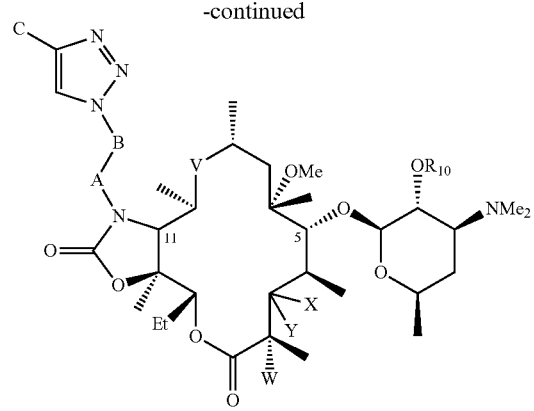

or a pharmaceutically acceptable salt thereof, wherein:

$R_1$ is H, cyclic or acyclic alkyl, cyclic or acyclic alkyl-hydroxyamine, aryl, aryl-hydroxyamine, cyclic or acyclic acyl, cyclic or acyclic acyl-hydroxyamine, heteroalkyl, heteroalkyl-hydroxyamine, heteroaryl, heteroaryl-hydroxyamine, acylaryl, acylaryl-hydroxyamine, acylheteroaryl, acylheteroaryl-hydroxyamine, alkylaryl, alkylaryl-hydroxyamine, alkylheteroaryl, alkylheteroaryl-hydroxyamine, sulfonylalkyl, sulfonylalkyl-hydroxyamine, acyalkoxylsulfonylalkyl, or acylalkoxylsulfonylalkyl-hydroxyamine;

or $R_1$ is C(O)—$NR_4R_5$, where $R_4$ and $R_5$ are each independently selected from the group consisting of hydrogen, hydroxy, alkyl, aralkyl, alkylaryl, alkoxy, heteroalkyl, aryl, heteroaryl, dimethylaminoalkyl, acyl, sulfonyl, urea, and carbamate;

or $R_1$ is a D-glucose, D-mannose, D-xylose, D-galactose, L-fucose, D-ribose, D-arabinose, D-ribulose, D-fructose, sucrose, lactose, maltose, cellobiose, glucosamine, galactosamine, acetylglucose, acetylgalactose, N-acetylglucosamine, N-acetyl-galactosamine, galactosyl-N-acetylglucosamine, N-acetylneuraminic acid, mycaminose, L-vancosamine, 3-desmethyl-vancosamine, 3-epi-vancosamine, 4-epi-vancosamine, acosamine, 3-amino-glucose, 4-deoxy-3-amino-glucose, actinosamine, daunosamine, 3-epi-daunosamine, ristosamine, or N-methyl-D-glucamine, or clindamycin, each of which is optionally oxidized, reduced, or substituted;

$R_2$ and $R_3$ are OH, or $R_2$ and $R_3$ are taken together to form a carbonate or carbamate of the formula:

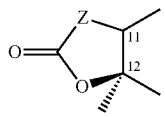

where Z is O, or —N($R_6$); where $R_6$ is hydrogen, hydroxy, optionally substituted alkyl, optionally substituted alkoxy, heteroalkyl, optionally substituted aryl, optionally substituted heteroaryl, dimethylaminoalkyl, acyl, or sulfonyl, or a group of the formula A-B-T-C, where T is a triazole;

X is H; and Y is $OR_7$; where $R_7$ is a pentose, hexose, alkyl, aryl, heteroaryl, acyl or —C(O)—$NR_8R_9$, where $R_8$ and $R_9$ are each independently selected from the group consisting of hydrogen, hydroxy, alkyl, aralkyl, alkylaryl, heteroalkyl, aryl, heteroaryl, alkoxy, dimethylaminoalkyl, acyl, sulfonyl, ureyl and carbamyl;

or X and Y are taken together with the attached carbon to form carbonyl;

V is —C(O)—, —C(=$NR_{11}$)—, —C($NR_{12}R_{13}$)—, or —N($R_{14}$)$CH_2$—, wherein the first dash of each of the foregoing V groups is attached to the C-10 carbon and the last dash of each group is attached to the C-8 carbon; and $R_{11}$ is hydroxy or alkoxy, $R_{12}$ and $R_{13}$ are each independently selected from the group consisting of hydrogen, hydroxy, alkyl, aralkyl, alkylaryl, alkoxy, heteroalkyl, aryl, heteroaryl, dimethylaminoalkyl, acyl, sulfonyl, ureyl, and carbamoyl; and $R_{14}$ is hydrogen, hydroxy, alkyl, aralkyl, alkylaryl, alkoxy, heteroalkyl, aryl, heteroaryl, dimethylaminoalkyl, acyl, sulfonyl, ureyl or carbamoyl;

W is H, F, Cl, Br, I, or OH;

A is —$CH_2$—, —C(O)—, —C(O)O—, —C(O)NH—, —S(O)$_2$—, —S(O)$_2$NH—, or —C(O)NHS(O)$_2$—;

B is —($CH_2$)$_n$— where n is an integer ranging from 0-10, or B is an unsaturated carbon chain of 2-10 carbons, which may contain any alkenyl or alkynyl group;

C is alkyl, aralkyl, alkylaryl, heteroalkyl, aryl, heteroaryl, aminoaryl, or alkylaminoaryl and $R_{10}$ is hydrogen or acyl.

2. The compound of claim 1 of Formula 1, or a pharmaceutically acceptable salt thereof, wherein $R_1$ is a D-glucose, D-mannose, D-xylose, D-galactose, L-fucose, D-ribose, D-arabinose, D-ribulose, D-fructose, sucrose, lactose, maltose, cellobiose, glucosamine, galactosamine, acetylglucose, acetylgalactose, N-acetylglucosamine, N-acetyl-galactosamine, galactosyl-N-acetylglucosamine, N-acetylneuraminic acid, mycaminose, L-vancosamine, 3-desmethyl-vancosamine, 3-epi-vancosamine, 4-epi-vancosamine, acosamine, 3-amino-glucose, 4-deoxy-3-amino-glucose, actinosamine, daunosamine, 3-epi-daunosamine, ristosamine, or N-methyl-D-glucamine, or clindamycin, each of which is optionally oxidized, reduced, or substituted.

3. The compound of claim 2 wherein $R_1$ is mycaminose or 4-deoxy-3-amino-glucose.

4. The compound of claim 2 wherein $R_1$ is clindamycin.

5. The compound of claim 1 of Formula 1, wherein $R_6$ is a group of the formula A-B-T-C, where T is a triazole.

6. The compound of claim 1 of Formula 2, or a pharmaceutically acceptable salt thereof.

7. The compound of claim 6 wherein X and Y are taken together with the attached carbon to form carbonyl.

8. The compound of claim 6 wherein V is —C(O)—.

9. The compound of claim 6 wherein W is H or F.

10. The compound of claim 9 wherein W is F.

11. The compound of claim 6 wherein A is —$CH_2$—, B is —($CH_2$)$_n$—, and n is an integer from 2-4.

12. The compound of claim 11 wherein n is 3.

13. The compound of claim 6 wherein C is optionally substituted aryl or optionally substituted heteroaryl.

14. The compound of claim 13 wherein C is 3-aminophenyl.

15. The compound of claim 6 wherein $R_{10}$ is hydrogen.

16. A pharmaceutical composition comprising a compound of claim 6 and one or more carriers, diluents, or excipients, or a combination thereof.

17. A unit dosage form comprising a therapeutically effective amount of a compound of claim 6.

18. A method for treating a disease comprising a bacterial infection in a host animal, the method comprising the step of administering a therapeutically effective amount of a compound of claim 6 to the host animal.

19. The method of claim 18 wherein the bacterial infection is a respiratory tract infection.

20. The method of claim 18 wherein the disease is pneumonia.

* * * * *

UNITED STATES PATENT AND TRADEMARK OFFICE
CERTIFICATE OF CORRECTION

PATENT NO. : 9,200,026 B2
APPLICATION NO. : 13/722058
DATED : December 1, 2015
INVENTOR(S) : Chang-Hsing Liang et al.

It is certified that error appears in the above-identified patent and that said Letters Patent is hereby corrected as shown below:

In the claims

In claim 1, column 61, line 54,

" 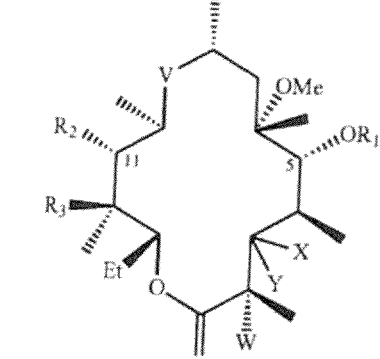 " should read -- 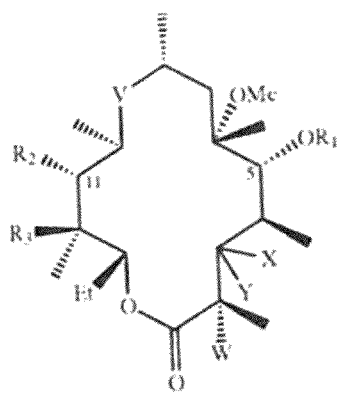 (1) --

In claim 1, column 62, line 43,

" 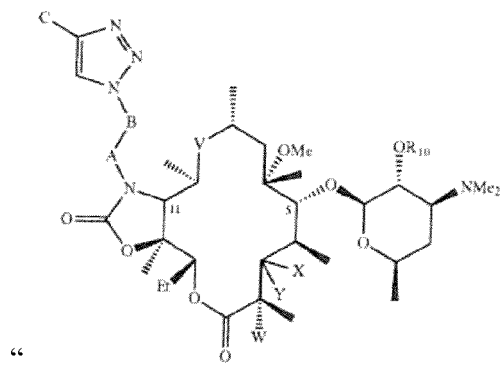 " should read -- 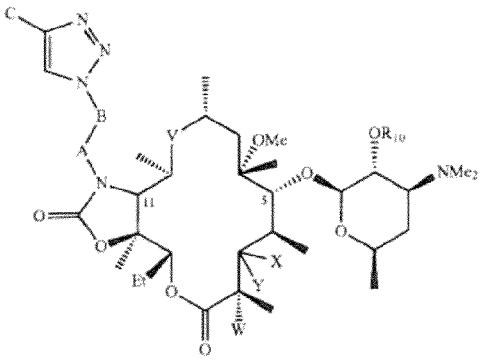 (2) --

Signed and Sealed this
Tenth Day of May, 2016

Michelle K. Lee
*Director of the United States Patent and Trademark Office*